(12) United States Patent
Jewett et al.

(10) Patent No.: US 12,157,908 B2
(45) Date of Patent: Dec. 3, 2024

(54) CELL-FREE PROTEIN SYNTHESIS PLATFORMS DERIVED FROM CLOSTRIDIA EXTRACTS

(71) Applicants: Northwestern University, Evanston, IL (US); LanzaTech, Inc., Skokie, IL (US)

(72) Inventors: Michael Christopher Jewett, Evanston, IL (US); Antje Kruger-Gericke, Evanston, IL (US); Alexander Paul Mueller, Skokie, IL (US); Michael Koepke, Chicago, IL (US)

(73) Assignees: Northwestern University, Evanston, IL (US); LanzaTech, Inc., Skokie, IL (US)

( * ) Notice: Subject to any disclaimer, the term of this patent is extended or adjusted under 35 U.S.C. 154(b) by 1319 days.

(21) Appl. No.: 16/800,844

(22) Filed: Feb. 25, 2020

(65) Prior Publication Data

US 2020/0270665 A1    Aug. 27, 2020

Related U.S. Application Data

(60) Provisional application No. 62/810,014, filed on Feb. 25, 2019.

(51) Int. Cl.
| | |
|---|---|
| *C12P 21/00* | (2006.01) |
| *C12N 1/20* | (2006.01) |
| *C12N 9/12* | (2006.01) |
| *C12N 15/10* | (2006.01) |

(52) U.S. Cl.
CPC ............. *C12P 21/00* (2013.01); *C12N 1/20* (2013.01); *C12N 9/1247* (2013.01); *C12N 15/1072* (2013.01); *C12Y 207/07006* (2013.01)

(58) Field of Classification Search
CPC .... C12N 1/20; C12N 9/1247; C12N 15/1051; C12N 15/1072; C12N 15/52; C12P 21/00; C12P 21/02; C12Y 207/07006
See application file for complete search history.

(56) References Cited

U.S. PATENT DOCUMENTS

| | | | |
|---|---|---|---|
| 4,458,066 A | 7/1984 | Caruthers | |
| 4,683,195 A | 7/1987 | Mullis | |
| 4,683,202 A | 7/1987 | Mullis | |
| 5,494,810 A | 2/1996 | Barany | |
| 6,994,986 B2 | 2/2006 | Swartz | |
| 7,008,651 B2 | 3/2006 | Ambuel | |
| 7,041,479 B2 | 5/2006 | Swartz | |
| 7,189,525 B2 | 3/2007 | Deleersnijder | |
| 7,235,382 B2 | 6/2007 | Endo | |
| 7,273,615 B2 | 9/2007 | Endo | |
| 7,312,049 B2 | 12/2007 | Calhoun | |
| 7,338,789 B2 | 3/2008 | Swartz | |
| 7,396,664 B2 | 7/2008 | Daly | |
| 8,298,759 B2 | 10/2012 | Voloshin | |
| 8,357,529 B2 | 1/2013 | Swartz | |
| 8,519,122 B2 | 8/2013 | Jewett | |
| 8,703,936 B2 | 4/2014 | Jewett | |
| 8,734,856 B2 | 5/2014 | Endo | |
| 9,005,920 B2 | 4/2015 | Kusumegi | |
| 9,057,071 B2 * | 6/2015 | Koepke | C12N 15/52 |
| 9,410,170 B2 | 8/2016 | Calhoun | |
| 9,528,137 B2 | 12/2016 | Jewett | |
| 10,118,950 B2 | 11/2018 | Jewett | |
| 10,465,221 B2 | 11/2019 | Jewett | |
| 10,494,600 B2 | 12/2019 | Heijstra | |
| 2004/0038332 A1 | 2/2004 | Swartz | |
| 2004/0209321 A1 | 10/2004 | Swartz | |
| 2005/0032086 A1 | 2/2005 | Sakanyan | |
| 2005/0054044 A1 | 3/2005 | Swartz | |
| 2005/0064592 A1 | 3/2005 | Endo | |
| 2005/0148046 A1 | 7/2005 | Endo | |
| 2005/0186655 A1 | 8/2005 | Endo | |
| 2007/0141661 A1 | 6/2007 | Endo | |
| 2007/0154983 A1 | 7/2007 | Calhoun | |
| 2008/0024821 A1 | 1/2008 | Silverbrook | |
| 2008/0138857 A1 | 6/2008 | Swartz | |
| 2008/0248521 A1 | 10/2008 | Knapp | |
| 2009/0042244 A1 | 2/2009 | Voloshin | |
| 2011/0207147 A1 | 8/2011 | Jewett | |
| 2012/0088269 A1 | 4/2012 | Kusumegi | |
| 2014/0045207 A1 | 2/2014 | Jewett | |
| 2014/0295492 A1 | 10/2014 | Jewett | |
| 2015/0259757 A1 | 9/2015 | Jewett | |
| 2016/0017276 A1 | 1/2016 | Heijstra | |
| 2016/0060301 A1 | 3/2016 | Jewett | |
| 2016/0362708 A1 | 12/2016 | Jewett | |
| 2017/0073381 A1 | 3/2017 | Jewett | |

(Continued)

FOREIGN PATENT DOCUMENTS

| | | |
|---|---|---|
| WO | 2018165159 A1 | 9/2018 |
| WO | 2019164558 A2 | 8/2019 |

OTHER PUBLICATIONS

Martin et al. (Biotechnology and Bioengineering, 2016, 113:531-539) (Year: 2016).*
Tomas et al. (Applied and Environmental Microbiology, 2003, pp. 4951-4965) (Year: 2003).*
Anderson-Beckh, B., et al. In Vitro Transcription and Translation in a Cell-Free System from Clostridium tetani. "Methods in Molecular Biology, vol. 37: In Vitro Transcription and Translation Protocols", Jan. 19, 1995 (Jan. 19, 1995), Humana Press Inc., XP009530904, ISBN: 978-0-89603-288-0, pp. 253-263.
Supplementary Partial European Search Report for corresponding application No. EP 20762883, Nov. 21, 2022 (13 pages).
Carlson, E. D., et al. "Cell-free protein synthesis: applications come of age." Biotechnology advances 30.5 (2012):1185-1194.

(Continued)

*Primary Examiner* — Jeremy C Flinders
(74) *Attorney, Agent, or Firm* — Quarles & Brady LLP

(57) ABSTRACT

Disclosed are compositions, methods, and kits for performing cell-free RNA transcription and/or cell-free protein synthesis (CFPS). The disclosed compositions, methods, and kits include or utilize components prepared from a species of Clostridia such as cellular extracts from *Clostridium autoethanogenum*.

19 Claims, 25 Drawing Sheets
Specification includes a Sequence Listing.

(56) References Cited

U.S. PATENT DOCUMENTS

| | | | |
|---|---|---|---|
| 2017/0292138 A1* | 10/2017 | Blake | C12N 1/06 |
| 2017/0306320 A1 | 10/2017 | Jewett | |
| 2017/0349928 A1 | 12/2017 | Jewett | |
| 2018/0016612 A1 | 1/2018 | Jewett | |
| 2018/0016614 A1 | 1/2018 | Jewett | |
| 2018/0298416 A1 | 10/2018 | Jewett | |
| 2019/0284600 A1 | 9/2019 | Jewett | |
| 2020/0270665 A1 | 8/2020 | Jewett | |

OTHER PUBLICATIONS

Caschera, F., et al., 2014. Synthesis of 2.3 mg/ml of protein with an all *Escherichia coli* cell-free transcription—translation system. Biochimie 99, 162-168. https://doi.org/10.1016/J.BIOCHI.2013.11.025.

Chappell, J., et al, 2013. Validation of an entirely in vitro approach for rapid prototyping of DNA regulatory elements for synthetic biology. Nucleic Acids Res. 41, 3471-3481. https://doi.org/10.1093/nar/gkt052.

Des Soye, B.J., et al., 2018. Establishing a High-Yielding Cell-Free Protein Synthesis Platform Derived from Vibrio natriegens. ACS Synth. Biol. 7, 2245-2255. https://doi.org/10.1021/acssynbio.8b00252.

Dudley, Q.M., et al., 2019. Cell-free biosynthesis of limonene using enzyme-enriched *Escherichia coli* lysates. Synth. Biol. (Oxford, England) 4. https://doi.org/10.1093/SYNBIO/YSZ003.

Endoh, T., et al., 2006. Cell-free protein synthesis at high temperatures using the lysate of a hyperthermophile. J. Biotechnol. 126, 186-195. https://doi.org/10.1016/J.JBIOTEC.2006.04.010.

Endoh, T., et al., 2007. A highly productive system for cell-free protein synthesis using a lysate of the hyperthermophilic archaeon, Thermococcus kodakaraensis. Appl. Microbiol. Biotechnol. 74, 1153-1161. https://doi.org/10.1007/s00253-006-0753-3.

Endoh, T., et al., 2008. Effective approaches for the production of heterologous proteins using the Thermococcus kodakaraensis-based translation system. J. Biotechnol. 133, 177-182. https://doi.org/10.1016/J.JBIOTEC.2007.08.036.

Failmezger, J., et al., 2018. Cell-Free Protein Synthesis From Fast-Growing Vibrio natriegens. Front. Microbiol. 9, 1146. https://doi.org/10.3389/fmicb.2018.01146.

Ferrer-Miralles, N., et al., 2009. Microbial factories for recombinant pharmaceuticals. Microb. Cell Fact. 8, 17. https://doi.org/10.1186/1475-2859-8-17.

Feustel, L., et al., 2004. Characterization and Development of Two Reporter Gene Systems for Clostridium acetobutylicum. Appl. Environ. Microbiol. 70, 798-803. https://doi.org/10.1128/AEM.70.2.798-803.2004.

Garamella, J., et al., 2016. The All *E. coli* TX-TL Toolbox 2.0: A Platform for Cell-Free Synthetic Biology. ACS Synth. Biol 5, 355. https://doi.org/10.1021/acssynbio.5b00296.

Ghaffar, T., et al., 2014. Recent trends in lactic acid biotechnology: A brief review on production to purification. J. Radiat. Res. Appl. Sci. 7, 222-229. https://doi.org/10.1016/J.JRRAS.2014.03.002.

Gregorio, N. E., et al. "A user's guide to cell-free protein synthesis." Methods and protocols 2.1 (2019): 24.

Harris, D. C., et al. "Cell-free biology: exploiting the interface between synthetic biology and synthetic chemistry." Current opinion in biotechnology 23.5 (2012): 672-678.

Heijstra, B.D., et al., 2017. Gas fermentation: cellular engineering possibilities and scale up. Microb. Cell Fact. 16, 60. https://doi.org/10.1186/s12934-017-0676-y.

Hodgman, C.E., et al., 2012. Cell-free synthetic biology: Thinking outside the cell. Metab. Eng. 14, 261-269. https://doi.org/10.1016/J.YMBEN.2011.09.002.

International Searching Authority. International Search Report and Written Opinion for application PCT/US2020/019719. Mailed on Jun. 18, 2020.

Jaroentomeechai, T., et al., 2018. Single-pot glycoprotein biosynthesis using a cell-free transcription-translation system enriched with glycosylation machinery. Nat. Commun. 9, 2686. https://doi.org/10.1038/s41467-018-05110-x.

Jermutus, L., et al., 1998. Recent advances in producing and selecting functional proteins by using cell-free translation. Curr. Opin. Biotechnol. 9, 534-548. https://doi.org/10.1016/S0958-1669(98)80042-6.

Jewett, M.C., et al, 2004. Mimicking the *Escherichia coli* cytoplasmic environment activates long-lived and efficient cell-free protein synthesis. Biotechnol. Bioeng. 86, 19-26. https://doi.org/10.1002/bit.20026.

Jewett, M.C., et al. "An integrated cell-free metabolic platform for protein production and synthetic biology." Molecular systems biology 4.1 (2008): 220.

Jones, D.T., 2005. Applied Acetone-Butanol Fermentation, in: Clostridia. Wiley-VCH Verlag GmbH, Weinheim, FRG, pp. 125-168. https://doi.org/10.1002/3527600108.ch5.

Joseph, R.C., et al., 2018. Recent Developments of the Synthetic Biology Toolkit for Clostridium. Front. Microbiol. 9, 154. https://doi.org/10.3389/fmicb.2018.00154.

Karig, D.K., et al., 2017. Preservation of protein expression systems at elevated temperatures for portable therapeutic production. J. R. Soc. Interface 14, 20161039. https://doi.org/10.1098/rsif.2016.1039.

Karim, A.S., et al., 2016. A cell-free framework for rapid biosynthetic pathway prototyping and enzyme discovery. Metab. Eng. 36, 116-126. https://doi.org/10.1016/J.YMBEN.2016.03.002.

Karim, A.S., et al., 2018. Controlling cell-free metabolism through physiochemical perturbations. Metab. Eng. 45, 86-94. https://doi.org/10.1016/J.YMBEN.2017.11.005.

Karim, A.S., et al., 2019. In vitro prototyping and rapid optimization of biosynthetic enzymes for cellular design. bioRxiv. https://doi.org/10.1101/685768.

Kelwick, R., et al., 2016. Development of a Bacillus subtilis cell-free transcription-translation system for prototyping regulatory elements. Metab. Eng. 38, 370-381. https://doi.org/10.1016/J.YMBEN.2016.09.008.

Kelwick, R., et al., 2017. Cell-free prototyping strategies for enhancing the sustainable production of polyhydroxyalkanoates bioplastics. bioRxiv. https://doi.org/10.1101/225144.

Kopke, M., et al. Clostridium ljungdahlii represents a microbial production platform based on syngas. Proceedings of the National Academy of Sciences 107, 13087-13092, (2010).

Kovtun, O., et al., 2010. Towards the Construction of Expressed Proteomes Using a Leishmania tarentolae Based Cell-Free Expression System. PLoS One 5, e14388. https://doi.org/10.1371/journal.pone.0014388.

Kracke, F., et al., 2016. Redox dependent metabolic shift in Clostridium autoethanogenum by extracellular electron supply. Biotechnol. Biofuels 9, 249. https://doi.org/10.1186/s13068-016-0663-2.

Kwon, Y.-C., et al., 2015. High-throughput preparation methods of crude extract for robust cell-free protein synthesis. Sci. Rep. 5, 8663.

Li, J., et al, 2018. Expanding the palette of Streptomyces-based cell-free protein synthesis systems with enhanced yields. Biochem. Eng. J. 130, 29-33. https://doi.org/10.1016/J.BEJ.2017.11.013.

Li, J., et al., 2017. Establishing a high yielding streptomyces-based cell-free protein synthesis system. Biotechnol. Bioeng. 114, 1343-1353. https://doi.org/10.1002/bit.26253.

Liew, F., et al., 2016. Gas Fermentation—A Flexible Platform for Commercial Scale Production of Low-Carbon-Fuels and Chemicals from Waste and Renewable Feedstocks. Front. Microbiol. | www.frontiersin.org 7. https://doi.org/10.3389/fmicb.2016.00694.

Liew, F., et al., 2017. Metabolic engineering of Clostridium autoethanogenum for selective alcohol production. Metab. Eng. 40, 104-114. https://doi.org/10.1016/J.YMBEN.2017.01.007.

Marshall, R., et al., 2018. Rapid and Scalable Characterization of CRISPR Technologies Using an *E. coli* Cell-Free Transcription-Translation System. Mol. Cell 69, 146-157.e3. https://doi.org/10.1016/J.MOLCEL.2017.12.007.

Martin, R.W., et al., 2018. Cell-free protein synthesis from genomically recoded bacteria enables multisite incorporation of noncanonical amino acids. Nat. Commun. 9, 1-9. https://doi.org/10.1038/s41467-018-03469-5.

(56) References Cited

OTHER PUBLICATIONS

Michel-Reydellet, N. et al. "Increasing PCR fragment stability and protein yields in a cell-free system with genetically modified *Escherichia coli* extracts." Journal of molecular microbiology and biotechnology 9.1 (2005): 26-34.
Mock, J., et al., 2015. Energy Conservation Associated with Ethanol Formation from H2 and CO2 in Clostridium autoethanogenum Involving Electron Bifurcation. J. Bacteriol. 197, 2965-80. https://doi.org/10.1128/JB.00399-15.
Moore, S. J.; et al., 2018. Rapid acquisition and model-based analysis of cell-free transcription-translation reactions from nonmodel bacteria. Proc. Natl. Acad. Sci. 115, E4340-E4349. https://doi.org/10.1073/pnas.1715806115.
Morgado, G., et al., 2018. Synthetic biology for cell-free biosynthesis: Fundamentals of designing novel in vitro multi-enzyme reaction networks, in: Advances in Biochemical Engineering/Biotechnology. Springer, Cham, pp. 117-146. https://doi.org/10.1007/10_2016_13.
Nagaraju, S., et al., 2016. Genome editing of Clostridium autoethanogenum using CRISPR/Cas9. Biotechnol Biofuels 9, 219. https://doi.org/10.1186/s13068-016-0638-3.
Nielsen, J., et al., 2014. Engineering synergy in biotechnology. Nat. Chem. Biol. 10, 319-322. https://doi.org/10.1038/nchembio.1519.
Nielsen, J., et al., 2016. Engineering Cellular Metabolism. Cell 164, 1185-1197. https://doi.org/10.1016/J.CELL.2016.02.004.
Pardee, K., et al., 2016. Portable, On-Demand Biomolecular Manufacturing. Cell 167, 248-259.e12. https://doi.org/10.1016/J.CELL.2016.09.013.
Pidot et al., "Discovery of clostrubin, and exceptional polyphenolic polyketide antibiotic from a strictly anaerobic bacterium," Angew. Chem. Int. Ed. Engl. Jul. 21, 2014; 53(30): 7856-9.
Siegal-Gaskins, D., et al., 2014. Gene Circuit Performance Characterization and Resource Usage in a Cell-Free "Breadboard." ACS Synth. Biol. 3, 416-425. https://doi.org/10.1021/sb400203p.
Silverman, A.D., et al., 2019. Deconstructing Cell-Free Extract Preparation for in Vitro Activation of Transcriptional Genetic Circuitry. ACS Synth. Biol. 8, 403-414. Published online Dec. 31, 2018. https://doi.org/10.1021/acssynbio.8b00430.
Sullivan, C.J., et al., 2016. A cell-free expression and purification process for rapid production of protein biologics. Biotechnol. J. 11, 238-248. https://doi.org/10.1002/biot.201500214.
Takahashi, M. K, et al., 2015. Characterizing and prototyping genetic networks with cell-free transcription-translation reactions. Methods. https://doi.org/10.1016/j.ymeth.2015.05.020.
Takahashi, M. K., et al., 2015. Rapidly Characterizing the Fast Dynamics of RNA Genetic Circuitry with Cell-Free Transcription-Translation (TX-TL) Systems. ACS Synth. Biol. 4, 503-515. https://doi.org/10.1021/sb400206c.
Tracy, B.P., et al., 2012. Clostridia: the importance of their exceptional substrate and metabolite diversity for biofuel and biorefinery applications. Curr. Opin. Biotechnol. 23, 364-381. https://doi.org/10.1016/J.COPBIO.2011.10.008.
Batista AC et al., Optimising protein synthesis in cell-free systems, a review, Engineering biology, 2021, 5(1): 10-19.
Xiaoge Jia et al., Progress of cell-free protein synthesis system and its applications in pharmaceutical engineering—A review, Acta Microbiologica Sinica, 2016, 56(3): 530-542.
Andersen-Beckh B. et al., "Expression of Tetanus Toxin Subfragments In Vitro and Characterization of Epitopes", Infect. Immun., 57(11), pp. 3498-3505, Nov. 1989 (Nov. 1989).
Canadian Office Action, corresponding to CA 3131243, dated Nov. 17, 2023.
Chinese Office Action, corresponding to CN 202080016173.6, dated Oct. 31, 2023.

\* cited by examiner

Figure 2
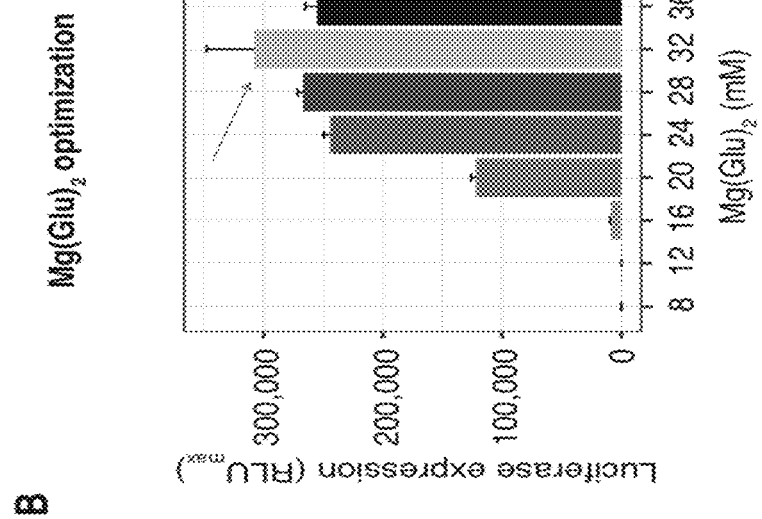
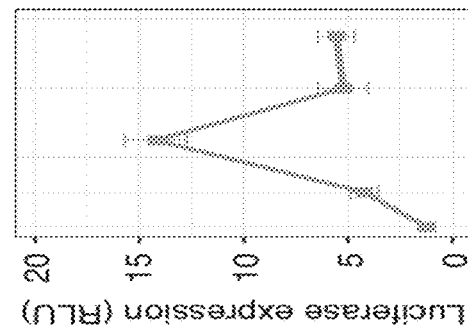
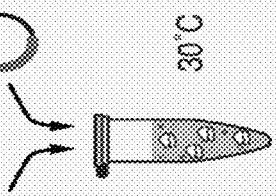

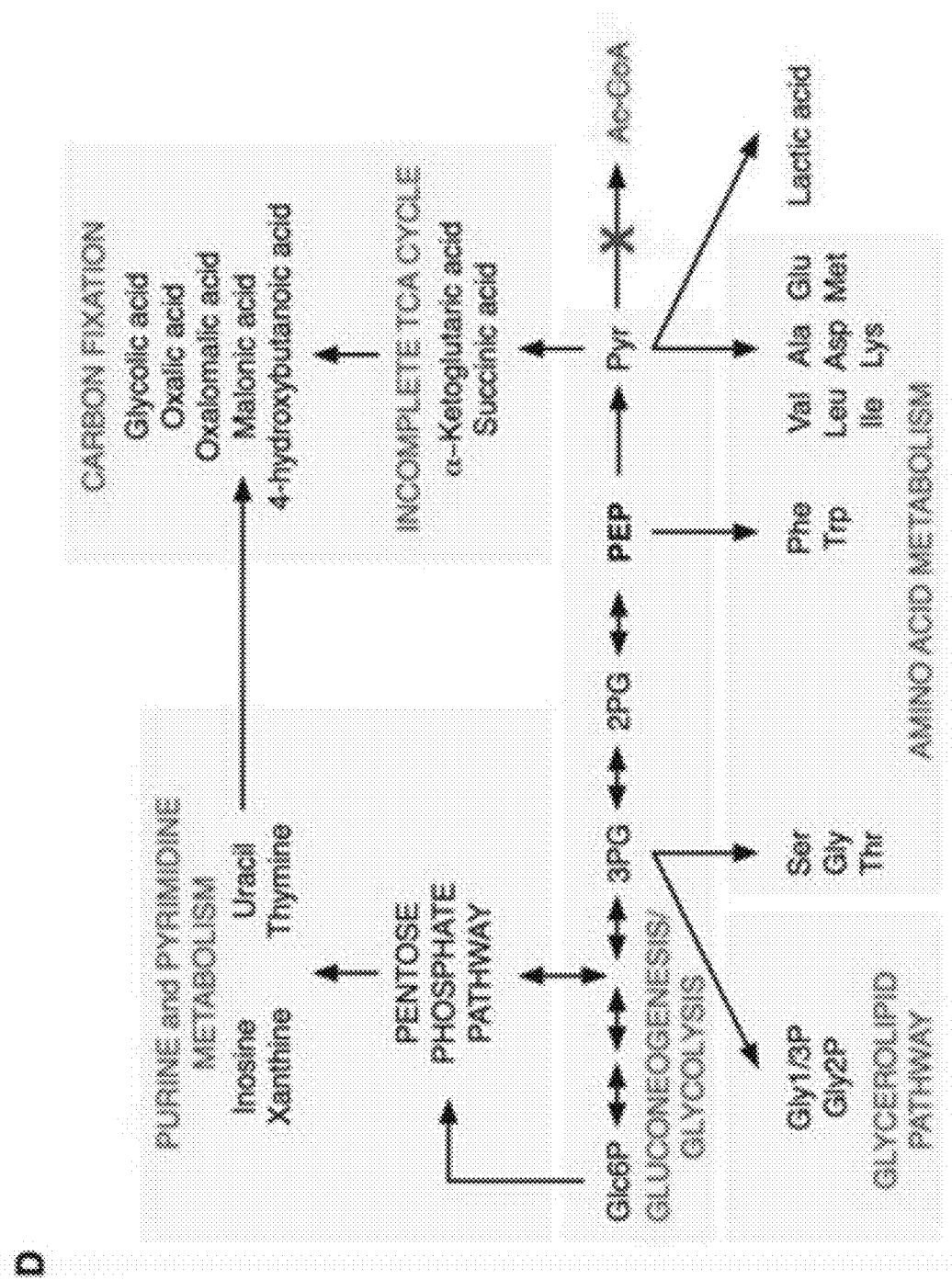
Figure 5, con't.

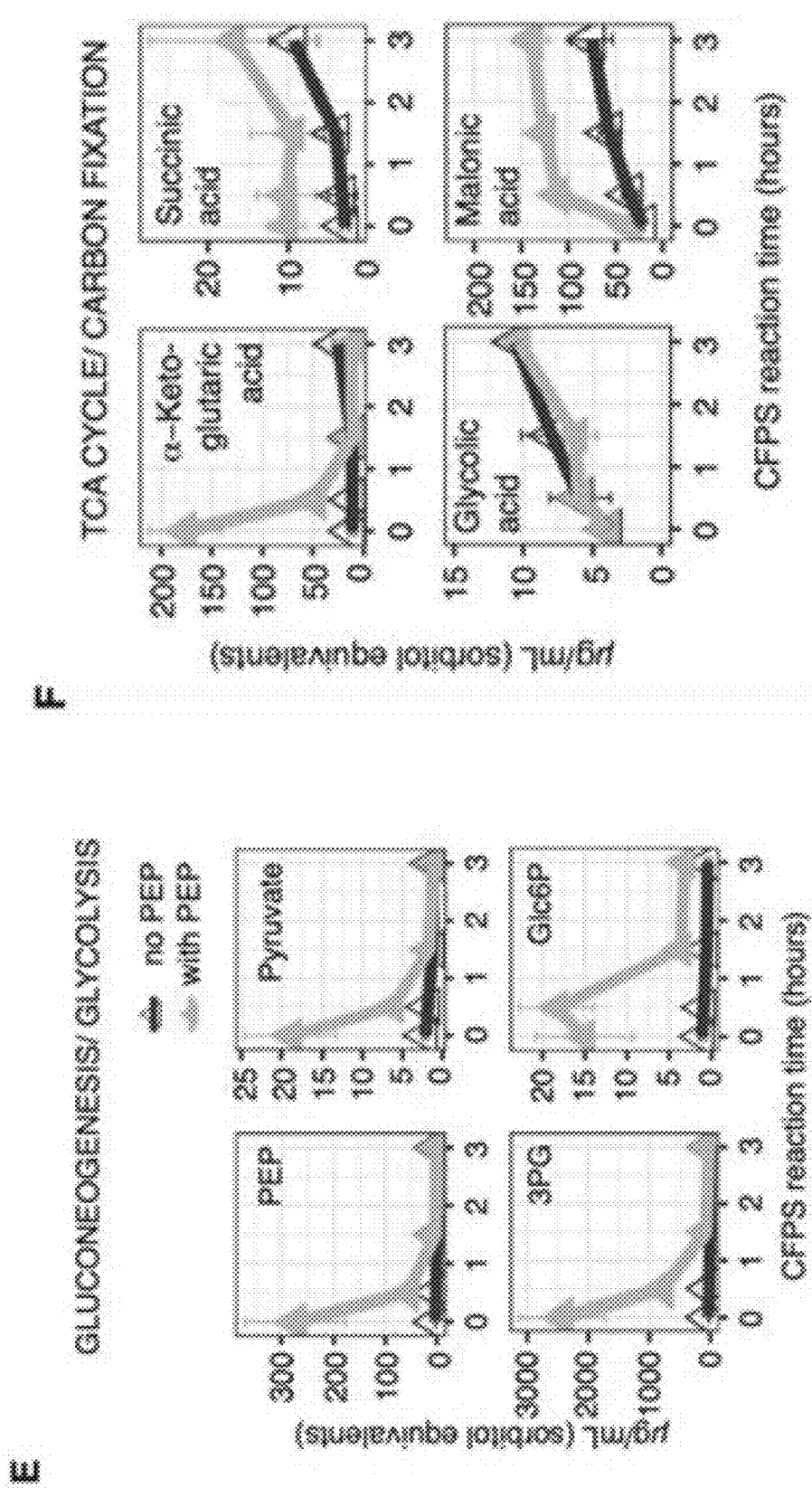
Figure 5, con't.

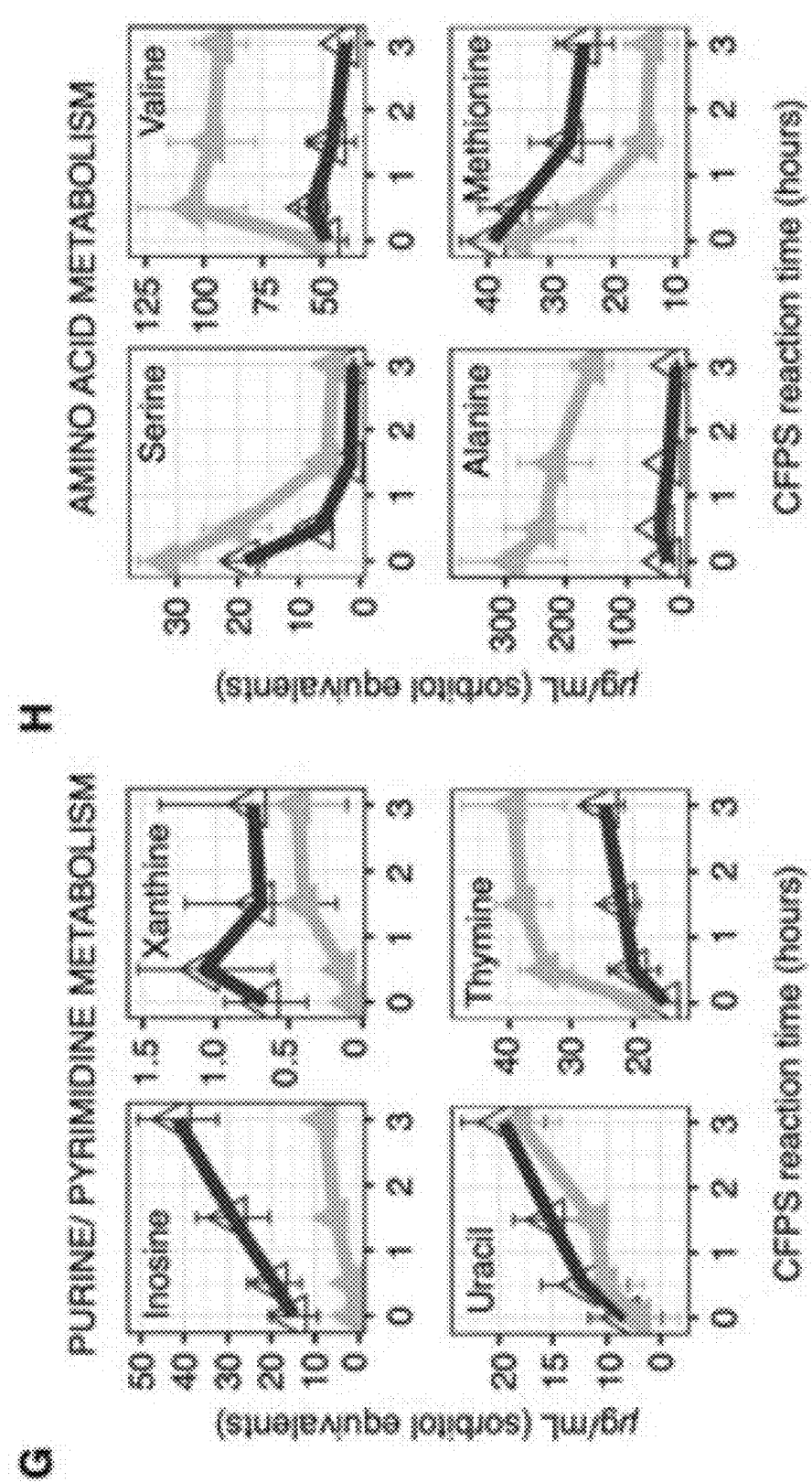
Figure 5, con't.

| Name | Sequence |
|---|---|
| pJL1 linear F | CTGAGATACCTACAGCGTGAGC |
| pJL1 linear R | CGTCACTCATGGTGATTTCTCACTTG |
| PS_pJL1 linear F | C*C*G*A*A*CTGAGATACCTACAGCGTGAGC |
| PS_pJL1 linear R | T*C*A*G*T*CGTCACTCATGGTGATTTCTCACTTG |

B.

| Reagent | Final concentration/ volume |
|---|---|
| Mg(Glu)$_2$ | 24 mM |
| Amino acids (all 20) | 1 mM |
| PEP | 45 mM |
| NAD$^+$ | 0 mM |
| CoA | 0 mM |
| Plasmid DNA | 15 nM |
| C. auto extract | 5 µL |

Figure 14

Promoter + 5'UTRs:

phosphotransacetylase-acetate kinase operon (pPta-Ack; CAETHG_RS16490) promoter
GGCCGCAATATGATATTTATGTCCATTGTGAAAGGATTATATTCAACTATTATTCCAGTTAC
GTTCATAGAAATTTCCTTTCTAAAATATTTTATTCCATGTCAAGAACTCTGTTATTCATTA
AAGAACTATAAGTACAAAGTATAAGGCATTTGAAAAAATAGGCTAGTATATTGATTGATTATT
TATTTTAAATGCCTAAGTGAAATATCTATTTCAGATTAAATTTTATTGATTTGTAAAGTTATATGTAGG
ATTTTTAAATAGAGTATCTATTTCAGATTAAATTTTGATACTTTAATTTGTGAAATTCTATCAAAGT
TGAGTAAAGTATTGACTAGCAAAATTTTTGAATAACAACTAAAAAGGATTATAGTATAAGTGTGTA
TATATTTTGAATAATTTATTGAAAATACAACTAAAAAGGATTATAGTATAAGTGTGTA
ATTTGTGTTAAATTTAAAGGGGAGGAAATGAACATGAAACAT pyruvate:formate oxidoreductase (pPFOR; CAETHG_RS14890) promoter
GCAAAATAGTTGATAATGCAGAGTTATAAACAAAGGTGAAAAGCATTACTTGTATTCTTT
TTTATATATTATTATAAATTAAAATGAAGCTGTATTAGAAAAAATACACACCTGTAATATAAAA
TTTTAAATTTAATTTAATTTTTCAAATGTATTTTACATGTTTAGAATTTTGATGTATATAA
AATAGTAGAATACATAAGATACTTAATTAATTAAGATAGTAAGTACTTTTCAATGTCTTT
TTTAGATGTTAATACAAATCTTTAATTGTAAAAAAATGCTACAGTGTTTAAATTATATTTGT
ACGGGATTAAACTGTATTAATTAAATAAAAAAATAAGTACAGTGTTTAAATTATATTTGT
ATTAAATCTAATAGTACGATGTAAGTTATTTTATACTATTGCTAGTTTAATAAAAGATTTAAT
TATATACTTGAAAGGAGGAGGAATCCAT

Figure 14, con't.

Promoter + 5'UTRs:

Wood-Ljungdahl cluster (pWL; CAETHG_RS07860) promoter
AGATAGTCATAATAGTTCCAGAATAGTTCAATTAGAAATTAGACTAAACTTCAAATGTTTG
TAAATATACCAAACTAGTAGATATTTTTAAATACTGGACTTAAACAGTAGTAATTTGC
CTAAAAATTTTTCAATTTTTTAAAAATCCTTTTCAAGTTGTACATTGTTATGGTAATAT
GTAATTGAAGAAGTTATGTAGTAATATTGTAAACGTTTCTTGATTTTTTACATCCATGTAGT
GCTAAAAAACCAAATAATTTATTTCACATGCAATTGTATATTTCAAATAACAATATTTATTTCTCG
TAAATTCACAAATAATTAATAATATCAATAACCAAGATTATACTTAAATGGATGTTTAT
TTTTAACACTTTTAATTAAAATAAAAATAAAAATAGGGTTTAGGTAAAATTAAGTATATAATTGTA
TTATTACAATTAATTAAAAATAAAAATTAAGGTAAAATTAAGTTATTTTAAGAAGTA
ATTACAATAAAAATTGAAGTTATTCTTTAAGGAGGGAATTATTCAT

Figure 14, con't.

C. acetobutylicum codon-optimized

ATGGAGGATGCAAAGAATATTAAGAAAGGTCCAGCTCCTTTCTACCCTTTAGAAGACGGAA
CTGCTGGTGAGCAATTACACAAGGCAATGAAGAGGTATGCATTAGTACCAGGAACTATAGC
TTTACTGATGCTCATATTGAAGTAACATATGCAGAATACTTTGAGATGTCTGTGAG
GCTTGCAGAAGCAATGAAAAGATATGGATTAAATACTAACCAGGATAGTGGTTGTCTG
AAAACAGCTTACAATTCTTCATGCCAGTCTCTTGGAGCATTATTCATTGGAGTGCTGGCT
CCAGCAAATGACATTTACAACGAGAGGGAGTGTTAAATTCAATGAATATTAGTCAACCTAC
TGTAGTGTTCGTTTCTAAGAAGGGACTTCAGAAAATTCTAAACGTGCAAAAAAGCTACCAA
TTATTCAAAAGATAATAATTATGACTCAAAACTGATTACCAAGGATTCCAGAGCATGTATA
CTTTTGTTACATCTCATCTACCACCAGGTTTAATGAGTATGATTTCGTGCCAGAAAGCTTT
GACAGAGATAAGACAATAGCTTTGATTATGAACAGCTCAGGATCTACAGGACTACCTAAGG
GTGTGGCTCTACCTCATAGGACTGCTTGCGTTAGTTTAGTCATGCAAGGGACCCTATATT
TGGAAATCAAATATTCCTGATACTGCAATACTCAGTGTACCATTCATCACGGATTCG
GTATGTTCACACAGAACTTTTTAGGAGTCTAAAGCACACACTTATCAGTGGTACTTATGTAGGTC
GAGGAGAACATTTTTAGGAGTCTAAAGCACACACTTATCTATAGATGGGAGAAGCTTAGTGCC
AACATTATTAGTTTTCGCTAAAGCACACACTTATCTAAAGAGGTAGGAGAAGCTGTTGCAAAAGA
CGAAATAGCAAGCGGTGGAGCTGGAGAAACCAACATCAGCAATTTGAT
TTCCACTTACCTGGTATAAGAGGTGATTGACAGAAACAACATCAGCATTCTTTGAAGC
TACTCCAGAGGGAGATGACAAGCCAGGTGCTGTAGGAAAGGTGGTACCATTCTTTGAAGC
TAAAGTAGTAGACTTGGACACAGACTGATAATGTCAGTTCAGGTTATGTAAATAATCCAGAGCAACAAATGCACTTA
GTAAGGGGACCAATGATGATAATGTCAGTTCAGGTTATGTAAATAATCCAGAGCAACAAATGCACTTA
TAGATAAAGATGGTGGTTGCACAGCGGAGATATAGCTTACTGGGATGAGGAGCAACATTT
TTTATTGTGGACAGGCTTAAAAGTTTGATTAAATACAAAGGTTACCAGGTGGCACCAGCTG
AGCTTGAATCTATATTGCTTCAACACCCAAATATTTGATGCTGGTGTAGCAGGTCTTCCT
GATGATGATGCAGGAGAGCTTCCAGTGCTCGTTGCATCTCAGTTACACTCCAAGGATCTTCAAAGAAGCAAGG
ACAGAAAAGGAAATAGTGGACTACGTTGCATCTCAGGTATTAGAGCACGGAAAGAAGCAAGG
GAGGTGTGTTTTGTAGACGAAGTTCCTAAAGGATTGACAGGAAGTTGGACGCTAGGAA
GATTAGAGAGATTCTAATAAAGCTAAGAAGGGTGGTAAAAGTAAGTTATAG

Figure 14, con't.

C. autoethanogenum codon-optimized

ATGGAAGATGCAAAAATATAAAGAAGGACCAGCACCATTCTATCCACTTGAAGACGGAA
CAGCAGGAGAACAGCTACATAGAAGCAATGAAAAGATGCACTTGTACCGGAACAATAGC
TTTACTGATGCTCACATAGAAGTAAACATAACCTATGCGGAATATTTGAAATGTCAGTAA
GATTGGCGAGAGGCAATGAAAAGATAATGGATTAATACAAATCATAGAATAGTGTGTAGT
GAAAACAGCTTGCAGTTTTTATGCCTGTTGGTGCTTTATTCATAGGTGTAGCAGTAGC
ACCAGCTAATGATATATTTATAGAACGTGAGCTTTAAATTCTATGAATAAGTCAGCCAAC
TGTAGTATTTGTTCAAAGAAAGTTTGCAGAAGATTTGAATGTTCAAAAGAAATTGCCTAT
AATTCAAAAATAATAATTATGGATTCTAAGACAGATTATCAGGGATTCCAGTCTATGTATAC
ATTCGTAACATCTCATCTCCCCGGGATTTAATGAATATGACTTCGTACCTGAATCCTTTG
ATAGAGATAAGACAATAGCTTTAATCATGAATAGTTCAGGAAGCACAGGACTTCCTAAAGGT
GTGGCACTTCCACATAGAAATGCTTGTGTAGATTCTCTCATGCTAGAGATCCAATTTTTGG
AAATCAAATAATTCCAGATACAGCAATACAAGTGTAGTACCATTCCATCATGGATTGGGA
TGTTTACAACTCTTGGATATTTAATTTGTGGTTTTAGAGTGTATTAATGTATAGATTTGAGG
AAGAACTCTTCCTTGCTAAGGTACTCTTACTAAGAGACTATAAGATAAGATATATGATTTAAGCAACCTGTAAA
TATTTTCATTTTTGCTAAGGCGGCTCCACTATCTAAGGAAGTTGGAGAAGCTGTGCTAAAGATTCCA
TAGCATCAGGCGGCGGCTCCACTATCTAAGGAAGTTGGAGAAGCTGTGCTAAAGATTCCA
CTTACCAGGAATCAGGCAGGCAGGATATGGACTTACAGAGAAACAACTTCAGCAATTCTTATTACAC
CTGAAGGAGATGACAAGCCTGGAGCAGTAGGTAAAGTGGTACCATTCTTTGAAGCTAAAGT
AGTAGATTTAGATACAGGAGAAAAACATTGGGAGTTAACCAGAGAGGAGCTGTGTGTAAGA
GGACCTATGATAATGAGTGGATGGTAAATAATCCAGAAGCCACTAATGCATTAATAGATAA
GGATGGATGGCTGCATTCTGTGATAATATAAGCATATTTGGGATGAAGATGAACATTTATTG
TAGATAGACTAAAATCCCTAATAAAACATAAGGATACCAGGAGATAGCTCCAGCAGAATTAGAA
TCAATACTTCTGCAGCATCCAAACATTTGATGCAGGAGTAGCTGGATTACCAGATGATGA
TGCAGGAGAACTTCCTGCTGCAGTAGTTGTTTAGAGCATGCAAAGAAATTGACTGAAAAA
GAGATAGTTGACTATGTTGCAAGTCAGGTTACTACAGGAAGTCTTACAGGAAAATTGAGAGGGGTAG
TATTCGTAGATGAGGTTCCAAAGGTCCAAAAGGTTCCAAAAGAATTGCAAGATGCAAGAAAAATACGTGA
AATACTTATAAAGGCAAGAAGGGCAAATCAAAATTATAA

Figure 14, con't.

E. coli codon-optimized

ATGGAAGACGCCAAAAACATAAAGAAGAAAGGCCCGGCTCCATTCTATCCGCTAGAGGATGGA
ACCGCTGGAGAGCAACTGCATAAGGCTATGAAGAGATACGCCCTGGTTCCTGGAACAATT
GCTTTTACAGATGCACATATCGAGGTGAACATCACGTACGCGGAATACTTCGAAATGTCCG
TTCGGTTGGCAGAGATGTATGAAACGATATGGGCTGAATACAAATCACAGAATCGTCGTATG
CAGTGAAAACTCTCTTCAATTCTTTATGCCGGTGTTGGGCGCGGTTATTTATCGGAGTTGCA
GTTGCGCCCGCGAACGACATTTATAATGAACGTGAATTGCTCAACAGTATGAACATTTCGC
AGCCTACCGTAGTGTTGTTTCCAAAAAGGGGTTGCAAAATTTGAACGTGCAAAAAAA
TTACCAATAATCCAGAAAATTATTATCATGGATTCTAAAACGGATTACCAGGGATTTCAGTC
GATGTACACGTTCGTCACATCTCATCTACCTCCCGGTTTAATGAATACGATTTTGTACCAG
AGTCCTTTGATCGTGACAAACAATTGCACTGATAATGAACTCCTCTGGATCTACTGGGTTA
CCTAAGGGTGTGGCCCTTCCGCATAGAACTGCCTCGGTCAGATTCTCGCATGCCAGAGAT
CCTATTTTTGGCAATCAAATCATTCCGACTCGGATACTGATTGTGTTCATTCCATCAC
GGTTTTTGGAATGTTACTACACTCGGATATTGATATGTGGATTCGAGTCGTCTTAATGTA
TAGATTTGAAGAGAGCTGTTTTCATTCTCGCCAAAAGCACTCTGATTGACAAATACGATTATCTA
TAGTACCAACCCTATTTCATTCTCGCCAAAAGCACTCTGATTGACAAATACGATTATCTA
ATTACGAAATTGCTTCTGGGGCGCACCTCTTTCGAAAGAAGTCGGGAAGCGGTTG
CAAACGCTTCCATCTTCCAGGATACGACAAGGATATGGGCTCACTGAGACTACATCAGC
TATTCTGATTACACCCGAGGGGATGTGGATCTGGATACCGGGCGTAAAGTTGTTCCATT
TTTGAAGCGAAGGTTGTGTGATCTGGATACCGGGCGTTAATCAGAGAGGC
GAATTATGTGTCAGAGGACCTATGATTATGTCCGGTTATGTAAACAATCCGAAGCGACCA
ACGCCCTTGATTGACAAGGATGATGGCTGCTTGAAGTCTTAATTAAATACAAGGATACCAGGTGG
CGAACACTTCTTCATAGTTGACCGCTTGAAGTCTTAATTAAATACAAGGATACCAGGTGG
CCCCGCTGAATTGGAGTCGATATTGTTACAACACCCAACATCTTCGACGCGCGGCGTGG
CAGGTCTTCCCGACGATGACGGGAACTTCCCGCCCGTTGTGTTTGGAGCACG
GAAAGACGATGACGGAGAAAAGAGATCGTGGATTACGTCGCCAGTCAAGTAACAACCGGA
AAAGTTGCGCGAAGAGAGTGTGTTTGTGACGAAGTACCGAAGGTCTTACCGAAAAC
TCGACGCAAGAAAATCAGAGAGATCCTCATAAAGGCCAAGAAGGGCGAAGTCCAAAT
TGTAA

Figure 14, con't.

C. autoethanogenum metabolic genes:

Acetolactate decarboxylase (CAETHG_RS14410)

MDDEVKVPNHYQMSTINALVSGLYDGCVSLSKLLKGNFGIGTFKGLDGELTLLNGTFYRTKP
DGSVYVCSKNVSVPFAVVTELENYTNYNIQNRTSYEDIRKELDSFIESKNIFYAFYMEGKFNYVK
TRTVVKQNMPYKPMAEVVKDQPMFEYNGVDGYVVGFRCPDYVEGLNVPGYHFHFINKDKKF
GGHISEFSIENAKVYVQNCSCFRMELPKNESFYNMEVQDRNDEITSVEK*

Acetolactate synthase (CAETHG_RS08420)

MNRDIKKEVQLNTAQMLVKCLEAEGVKYIFGIPGEENLEIMNAISDSTIEFITTRHEQGAAFMADV
YGRLTGKAGVCLSTLGPGATNLVTGVADADSDGAPVVAITGQVGTERMHITSHQFLDLCKMFE
PITKRSKQIVRPDTVSEIIRLVFKYAESEKPGACHIDLPVNIAKMPVGALEKPLEKKIPPKEHADLS
TIEEAASEIFKAKNPIILAGSGAIRGNSSKAVTEFATKLKIPVINTMMAKGIIPMDNKYSMWTIGIPQ
KDYVNKIIEEADLVITIGYDIVEYAPSKWNINGDIKIVHIDARPSHINKLYQPIVEVVGDISDALYNIL
RRTSSKDEPVKALEIKSEMLAEHESYANDNAFPMKPQRILNDVRKVMGPHDIVISDVGAHKMWI
ARHYNCYEPNTCIISNGFATMGIGVPGAIAAKLINPDKKVLAIVGDGGFMMNNQELETALRIKTPI
VVLIFNDSNYGLIKWKQEEHYGKSCYVDFTNPDFVKLAESMYAKGYRVEKAEDLIPTLEEAFKQ
NVPAVIDCQVDYGENIKLTKHLKEVYENM*

Primary:secondary alcohol dehydrogenase (CAETHG_RS02620)

MKGFAMLGINKLGWIEKKNPVPGPYDAIVHPLAVSPCTSDIHTVFEGALGNRENMILGHEAVGEI
AEVGSEVKDFKVGDRVIVPCTTPDWRSLEVQAGFQQHSNGMLAGWKFSNFKDGVFADYFHV
NDADMNLAILPDEIPLESAVMMTDMMTTGFHGAELADIKMGSSVVVIGIGAVGLMGIAGSKLRG
AGRIIGVGSRPVCVETAKFYGATDIVNYKNGDIVEQIMDLTHGKGVDRVIMAGGAETLAQAVT
MVKPGGVISNINYHGSGDTLPIPRVQWGCGMAHKTIRGGLCPGGRLRMEMLRDLVLYKRVDL
SKLVTHVFDGAENIEKALLLMKNKPKDLIKSVVTF*

A.

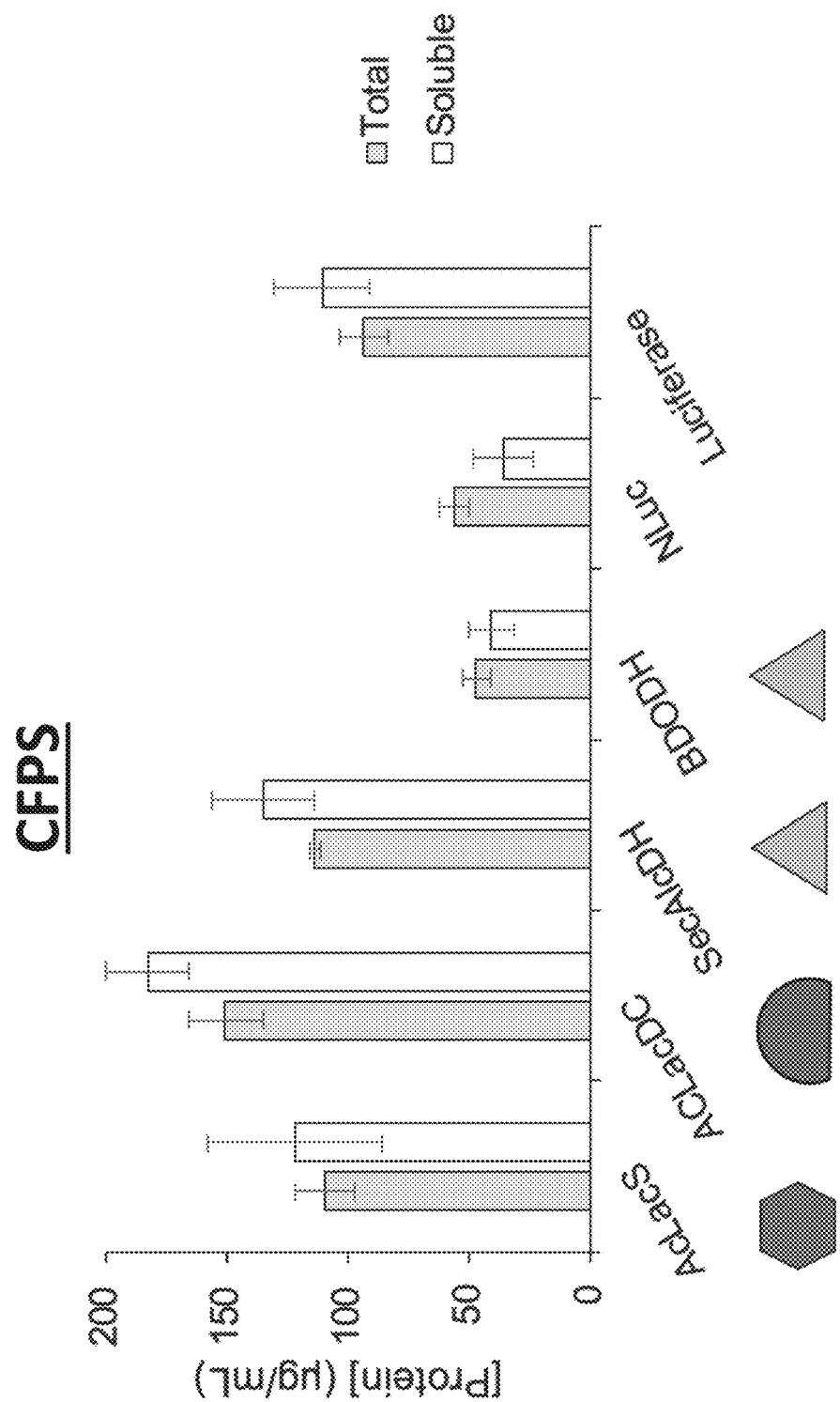
Figure 15, con't.

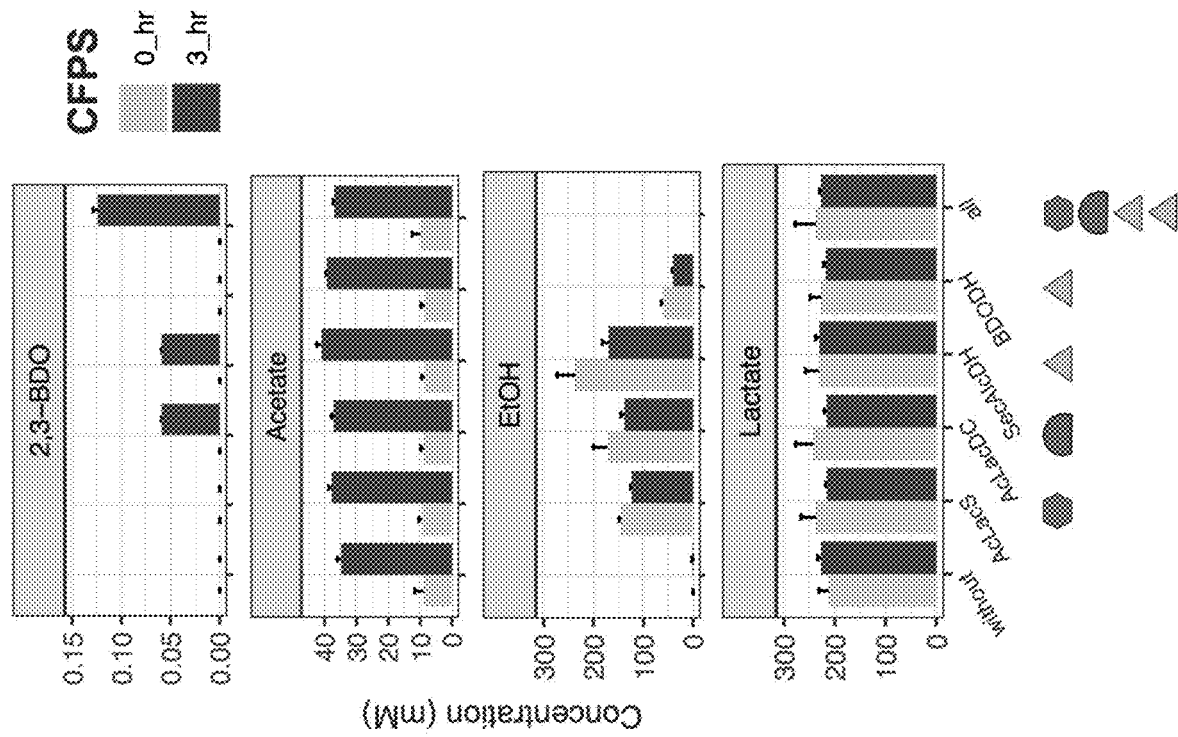
Figure 15, cont.
C.

CELL-FREE PROTEIN SYNTHESIS PLATFORMS DERIVED FROM CLOSTRIDIA EXTRACTS

CROSS-REFERENCE TO RELATED APPLICATIONS

This application claims the benefit of priority under 35 U.S.C. § 119(e) to U.S. Provisional Application No. 62/810,014, filed on Feb. 25, 2019, the content of which is incorporated herein by reference in its entirety.

STATEMENT REGARDING FEDERALLY SPONSORED RESEARCH OR DEVELOPMENT

This invention was made with government support under SC0018249 awarded by the Department of Energy. The government has certain rights in the invention.

BACKGROUND

The present invention generally relates to compositions, methods, and kits for performing cell-free RNA transcription and/or cell-free protein synthesis (CFPS). More specifically, the present invention relates to compositions, methods, and kits for performing cell-free RNA transcription and/or performing cell-free protein synthesis (CFPS) that include or utilize components prepared from a naturally occurring or recombinant species of Clostridia, including *Clostridium autoethanogenum*.

Clostridia are a class of Firmicutes that include *Clostridium* and other similar genera. Clostridia are gas and waste fermenting anaerobic bacteria with exceptional biomanufacturing potential (e.g. fuel and chemical production). (See, e.g., Tracy et al., "Clostridia: the importance of their exceptional substrate and metabolite diversity for biofuel and biorefinery application." Curr. Opin. Biotechno. 2012 June; 23(3): 364-81; the content of which is incorporated herein by reference in its entirety). Clostridia also have a wide range of medical applications (e.g. production of collagenases or Botulinum toxin for clinical applications) and recently first natural products from clostridia have been developed (e.g. with use as antibiotics or crop protectants). (See, e.g., Schiel et al., "*Clostridium*: Encyclopedia of Industrial Biotechnology: Bioprocess, Bioseparation, and Cell Technology, 2010; and Pidot et al., "Discovery of clostrubin, and exceptional polyphenolic polyketide antibiotic from a strictly anaerobic bacterium," Angew. Chem. Int. Ed. Engl. 2014 Jul. 21; 53(30): 7856-9; the contents of which are incorporated herein by reference in their entireties). Although Clostridia have been used industrially for over 100 years, the current state of art of strain engineering is still a low-throughput, labor-intensive and time-consuming challenge. Specific challenges to strain engineering include organism-specific genetic constraints, the requirement of an anaerobic environment, and in case of acetogens, the handling of gases. As a result, developments in Clostridia biotechnology and basic knowledge of Clostridia biology have lagged far behind achievements in aerobic prokaryotic and eukaryotic biology.

Here, the inventors present the first cell-free protein synthesis (CFPS) platform derived from an anaerobic bacterium, *Clostridium autoethanogenum*. The inventors' platform can be utilized for high-throughput prototyping of Clostridia genetic parts and metabolic pathways prior to in vivo implementation, as well as cell-free biomanufacturing of high-value products. The inventors have developed a series of protocols for cell growth in batch and continuous mode with different strains. The inventors have optimized of extract preparation, CFPS reaction components and CFPS reaction conditions that can be used for prototyping and biomanufacturing purposes. The inventors' optimized system is capable of producing up to 90 g/ml of luciferase reporter protein, which can be detected in high-throughput by luminescence measurements using standard laboratory equipment and provides a suitable dynamic range to begin determining nuances in genetic part libraries.

SUMMARY

Disclosed are compositions, methods, kits, and components for performing cell-free RNA transcription and/or performing cell-free protein synthesis (CFPS). The disclosed compositions, methods, and kits include or utilize components prepared from a naturally occurring or recombinant species of Clostridia, including *Clostridium autoethanogenum*. Further, the disclosed compositions, methods, kits, and components thereof, may be utilized for high-throughput prototyping of Clostridia genetic parts and metabolic pathways in vitro prior to in vivo implementation of the prototyped Clostridia genetic parts and metabolic pathways, for example, in Clostridia cells. The disclosed compositions, method, kits, and components thereof may also be used for biomanufacturing of high-value products in vitro in a cell-free system or in vivo.

BRIEF DESCRIPTION OF THE DRAWINGS

FIG. 2. *C. autoethanogenum*-derived CFPS requires different conditions than *E. coli*-derived CFPS. (A) Using *E. coli* conditions for extract preparation/processing and CFPS reactions, luciferase expression was determined in *C. autoethanogenum* extracts. (A, left and middle panel) Simplified schematic of extract preparation and processing steps and key components of CFPS reactions, respectively. (A, right panel) Luciferase expression in *C. autoethanogenum* extracts during CFPS at 8 mM Mg(Glu)$_2$. (B) Maximum luciferase expression during CFPS at different Mg(Glu)$_2$ concentrations. Arrow indicates optimized condition. *C. autoethanogenum* cell pellets were resuspended in S30 buffer, lysed by sonication at 640 J, clarified by centrifugation at 12,000×g, and used for CFPS containing the key components at indicated concentrations in (A). Luciferase expression was determined by bioluminescence. PEP: phosphoenolpyruvate; AAs: amino acids; NAD$^+$: reduced nicotinamide adenine dinucleotide; CoA: coenzyme A. Data are presented as mean±s.d. of at least three independent reactions.

FIG. 6. Provides tables showing A) oligonucleotide sequences, where "*" designates a phosphorothioate (PS) bond (i.e., sulfur atom substituting for a non-bridging oxygen in the phosphate backbone of an oligo). pJL1 linear F (SEQ ID NO: 21); pJL1 linear R (SEQ ID NO:22); PS_pJL1 linear F (SEQ ID NOL:23); and PS_pJL1 linear R (SEQ ID NO:24). B) exemplary optimized CFPS reaction conditions.

FIG. 14. Provides exemplary biological sequences for: 1) promoters and 5' UTRs: phosphotransacetylase-actetate kinase operon (pPta-Ack; CAETHG_RS16490) (SEQ ID NO:25); pyruvate:formate oxidoreductase (pPFOR; CAETHG_RS14890) promoter (SEQ ID NO:26); and the Wood-Ljungdahl cluster (pWL; CAETHG_RS07860) promoter (SEQ ID NO:27). 2) luciferase coding sequences: luciferase coding sequence adapted for expression in *Clostridium acetobutylicum* (SEQ ID NO: 17); luciferase coding sequence adapted for expression in *Clostridium autoethanogenum* (SEQ ID NO: 19), and luciferase coding sequence adapted for expression in *Escherichia coli* (SEQ ID NO:20); and 3) *Clostridium autoethanogenum* metabolic genes: Acetolactate decarboxylase (CAETHG_RS14410) (SEQ ID NO:28); Acetolactate synthase (CAETHG_RS08420) (SEQ ID NO:29); and Primary:secondary alcohol dehydrogenase (CAETHG_RS02620) (SEQ ID NO:30).

DETAILED DESCRIPTION

Definitions and Terminology

Figure 1:
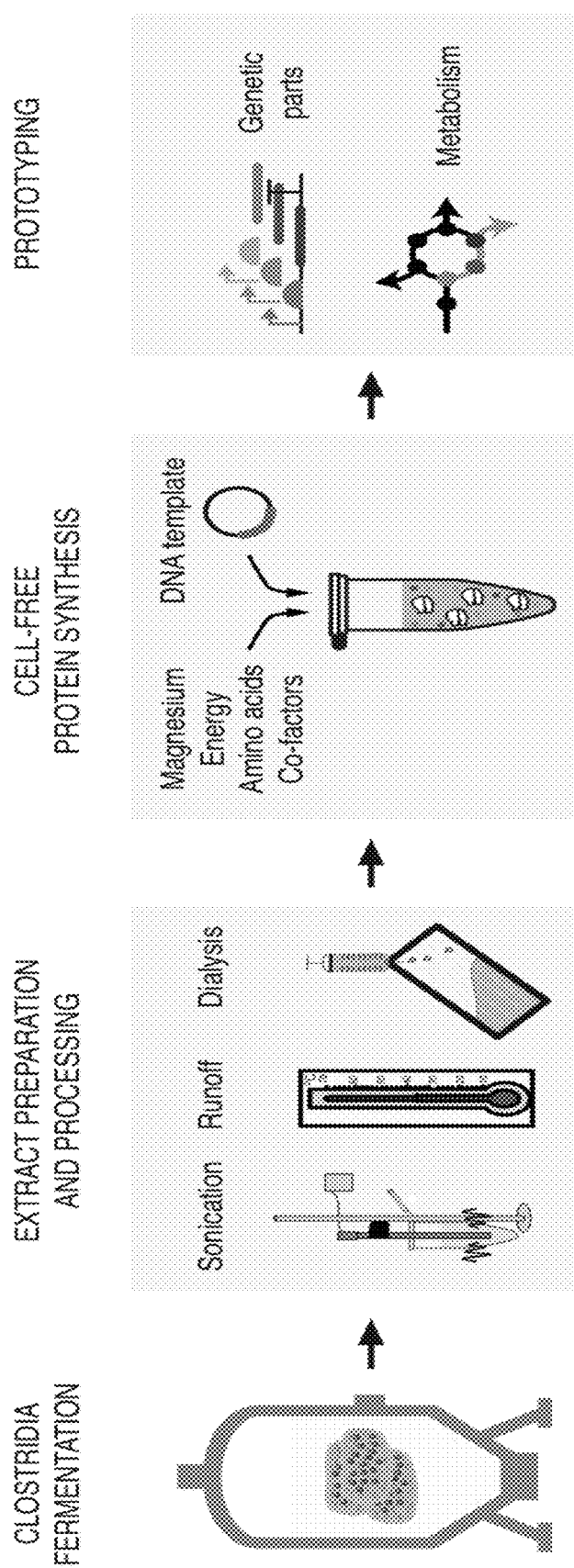
FIG. 1. Provides a schematic illustration of a simple, robust and high-yielding clostridia cell-free platform facilitating cell-free synthetic biology applications such as production of bio-products, prototyping of genetic parts, and metabolic pathway performance. Starting from cell pellets collected from clostridia cultures, we initially optimized extract preparation and processing by testing different sonication, runoff and dialysis conditions. In the second step, we adjusted concentrations of key components in the CFPS reaction to further maximize protein production. This optimized CFPS system was then used to demonstrate the system's capability for prototyping clostridia genetic parts and metabolic pathways.

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a component" should be interpreted to mean "one or more components" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Synthesis Methods

The disclosed methods, devices, kits, and components may utilize and/or include polynucleotides. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms "nucleic acid" and "oligonucleotide," as used herein, refer to polydeoxyribonucleotides (containing 2-de-oxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized and/or codon-adapted for expression in a particular host. In the art, codon usage frequency tables have been prepared for a number of host organisms including humans, mouse, rat, pig, *E. coli*, plants, and other host cells. In some embodiments, the polynucleotide sequences disclosed herein may encode a protein (e.g., a reporter protein such as luciferase) and may be codon-optimized and/or codon-adapted for expression in Clostridia (e.g., *Clostridium acetobutylicum, Clostridium autoethanogenum* and/or *E. coli* (see, e.g., SEQ ID NOs: 17-20 and FIG. 13).

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g. T3 RNA polymerase, T7 RNA polymerase, SP6 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence. As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro ribosomal assembly, transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

Oligonucleotides and polynucleotides may optionally include one or more nonstandard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

Peptides, Polypeptides, Proteins, and Synthesis Methods

The disclosed methods, devices, kits, and components may be utilized to synthesize proteins, polypeptides, and/or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine residues. The term "amino acid residue" may include alpha-, beta-, gamma-, and delta-amino acids.

In some embodiments, the term "amino acid residue" may include nonstandard, noncanonical, or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard, noncanonical, or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynyl, ether, thiol, sulfonyl, seleno, ester, thioacid, borate, boronate, 18ufa18hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Glu, His |
| Gly | Ala |
| His | Asn, Arg, Gln, Glu |
| Ile | Leu, Val |
| Leu | Ile, Val |
| Lys | Arg, Gln, Glu |
| Mel | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |

-continued

| Original Residue | Conservative Substitution |
| --- | --- |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

The proteins disclosed herein may be expressed from a "translation template." As used herein, "translation template" refers to an RNA product of transcription from an expression template that can be used by ribosomes to synthesize polypeptides or proteins.

The proteins disclosed herein may be expressed in a "reaction mixture." The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

Cell-Free Protein Synthesis

Cell-free protein synthesis (CFPS) and methods for making cell extracts for use in CFPS are known in the art. (See, e.g., Carlson et al., "Cell-free protein synthesis: Applications come of age," Biotech. Adv. Vol. 30, Issue 5, September-October 2012, Pages 1185-1194; Hodgman et al., "Cell-free synthetic biology: Thinking outside the cell," Metabol. Eng. Vol. 14, Issue 3, May 2012, Pages 261-269; and Harris et al., "Cell-free biology: exploiting the interface between synthetic biology and synthetic chemistry," Curr. Op. Biotech. Vol. 23, Issue 5, October 2012, Pages 672-678; see also U.S. Pat. Nos. 7,312,049; 7,008,651; and 6,994,986; see also U.S. Published Application Nos. 20170306320; 20160362708; 20160060301; 20120088269; 20090042244; 2008024821; 20080138857; 20070154983; 20070141661; 20050186655; 200501480461 20050064592; 20050032086; 20040209321; and 20040038332; the contents of which are incorporated herein by reference in their entireties).

The disclosed synthesis methods may utilize a cellular extract. As would be understood in the art, a cellular extract is an extract prepared from cells which is cell-free or substantially cell-free. For example, a cellular extract may be prepared by lysing cells using, for example, mechanical or chemical means, and isolating a fraction of the lysed cells which is cell-free or substantially cell free.

The disclosed compositions may include platforms for preparing a sequence defined biopolymer of protein in vitro. The platforms for preparing a sequence defined polymer or protein in vitro comprises a cellular extract from an organism, and in particulara species of Clostridia, such as *Clostridium autoethanogenum*. Because CFPS exploits an ensemble of catalytic proteins prepared from the crude lysate of cells, the cell extract (whose composition is sensitive to growth media, lysis method, and processing conditions) is an important component of extract-based CFPS reactions. A variety of methods exist for preparing an extract competent for cell-free protein synthesis, including those disclosed in U.S. Published Application No. 20140295492, published on Oct. 2, 2014, which is incorporated by reference in its entirety.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in U.S. Published Application Nos. 20170073381 and 20160060301, the contents of which are incorporated by reference in their entireties. In certain embodiments, one or more orthogonal components may be prepared in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture.

Platforms Comprising Extracts from Clostridia

The disclosed compositions (or systems) my include platforms for preparing a sequence defined biopolymer or protein in vitro, where the platform comprising a cellular extract prepared from a cell culture of a species of Clostridia, in particular *Clostridium autoethanogenum*.

Suitable species of Clostridia may include naturally occurring isolates (i.e., a wild-type species), or the species of Clostridia may be engineered. For example, the species of Clostridia may be engineered genetically to be deficient in a negative effector for cell-free protein synthesis (CFPS), for example via a knock-out mutation. Negative effectors for CFPS have been defined for *E. coli* and may include, but are not limited to, endA (SEQ ID NO: 1), lon (SEQ ID NO:2), mazF (SEQ ID NO:3), ompT (SEQ ID NO:4), rna (SEQ ID NO:5), rnb (SEQ ID NO:6), glpK (SEQ ID NO:7), gor (SEQ ID NO:8), gshA (SEQ ID NO:9), tnaA (SEQ ID NO:10), me (SEQ ID NO:11), gdhA (SEQ ID NO:12), sdaA (SEQ ID NO:13), sdaB (SEQ ID NO:14), speA (SEQ ID NO:15), WaaL (SEQ ID NO:16), and any combination thereof.

Suitable species of Clostridia may be engineered to be deficient in a gene encoding the corresponding homolog of any of *E. coli* endA, mazF, rna, rnb, rne, gor, lon, ompT, gdhA, gshA, sdaA, sdaB, speA, WaaL, tnaA, glpK, and any combination thereof. For example, the species of Clostridia may be deficient in a gene which encodes the corresponding homolog of any of *E. coli* endA, mazF, rna, rnb, rne, gor, lon, ompT, gdhA, gshA, sdaA, sdaB, speA, WaaL, tnaA, glpK, which homolog has at least about 20%, 30%, 40%, 50%, 60%, 70%, 75%, 80%, 85%, 90%, 95%, 96%, 97%, 98%, or 99% amino acid sequence identity to one or more of endA (SEQ ID NO:1), lon (SEQ ID NO:2), mazF (SEQ ID NO:3), ompT (SEQ ID NO:4), ma (SEQ ID NO:5), rnb (SEQ ID NO:6), glpK (SEQ ID NO:7), gor (SEQ ID NO:8), gshA (SEQ ID NO:9), tnaA (SEQ ID NO:10), rne (SEQ ID NO:11), gdhA (SEQ ID NO:12), sdaA (SEQ ID NO:13), sdaB (SEQ ID NO:14), speA (SEQ ID NO:15), WaaL (SEQ ID NO:16), and any combination thereof.

In addition or in the alternative, the species of Clostridia may be engineered to express an upregulated gene product that is a positive effector for CFPS. Positive effectors for CFPS have been defined for *E. coli* and may include, but are not limited to ackA, ndk, pykF, cdd, dsbC, dnaK, dnaJ, crpE, tig, groS, groL, infA, infB, fusA, efp, lepA, tufB, hslR, ffr, and any combination thereof. The species of Clostridia may be engineered genomically, for example by recombinantly introducing heterologous DNA into the genome of the Clostridia, and/or the Clostridia may be engineered by introducing an episomal vector (e.g., a plasmid) to the Clostridia in order to create an engineered species of Clostridia that expresses an upregulated gene product that is the corresponding homolog of any of *E. coli* ackA, ndk, pykF, cdd, dsbC, dnaK, dnaJ, crpE, tig, groS, groL, infA, infB, fusA, efp, lepA, tufB, hslR, ffr, and any combination thereof. For example, the Clostridia may be engineered to express an upregulated gene product that has an amino acid sequence having at least about 20%, 30%, 40%, 50%, 60%, 70%, 75%, 80%, 85%, 90%, 95%, 96%, 97%, 98%, or 99% amino acid sequence identity to one or more of *E. coli* ackA, ndk, pykF, cdd, dsbC, dnaK, dnaJ, crpE, tig, groS, groL, infA, infB, fusA, efp, lepA, tufB, hslR, ffr, and any combination thereof.

The species of Clostridia may be engineered to be deficient specifically in a release factor of translation. Release factors for translation may include, but are not limited to release factor 1 (RF-1).

The species of Clostridia may be genomically-recoded. For example, the Clostridia may be genomically-recoded to replace one or more stop codons with a different codon, optionally where all of one stop codon is replaced in the genome of the Clostridia with a different codon.

The species of Clostridia may be engineered to express a non-native or heterologous RNA polymerase, for example, by recombinantly introducing heterologous DNA encoding the RNA polymerase into the genome of the Clostridia, and/or the Clostridia may be engineered by introducing an episomal vector that expresses the RNA polymerase (e.g., a plasmid) to the Clostridia. Suitable RNA polymerases may include, but are not limited to T7 RNA polymerase.

The cellular extract of the platform is prepared from a cell culture of Clostridia. In some embodiments, the cell culture is in stationary phase. In some embodiments, stationary phase may be defined as the cell culture having an $OD_{600}$ of greater than about 3.0, 3.5, 4.0, 4.5, 5.0, 5.5, 6.0, 6.5, 7.0, 7.5, 8.0, or having an $OD_{600}$ within a range bounded by any of these values.

The cell extract may be prepared by lysing the cells of the cell culture and isolating a fraction from the lysed cells. For example, the cell extract may be prepared by lysing the cells of the cell culture and subjecting the lysed cells to centrifugal force, and isolating a fraction after centrifugation (e.g., where the S12 fraction and/or S30 fraction is isolated).

The platforms disclosed herein may include additional components, for example, one or more components for performing CFPS. Components may include, but are not limited to amino acids which optionally may include noncanonical amino acids, NTPs, salts (e.g., sodium salts, potassium salts, and/or magnesium salts), cofactors (e.g., nicotinamide adenine dinucleotide (NAD) and/or coenzyme-A (CoA)), an energy source and optionally an energy source comprising a phosphate group (e.g., phosphoenol pyruvate (PEP), ATP, or creatine phosphate), a translation template (e.g., a non-native mRNA that is translated in the platform) and/or a transcription template (e.g., a template DNA for synthesizing a non-native mRNA that is translated in the platform), and any combination thereof.

In some embodiments, the platform may comprise an energy source and optionally an energy source comprising a phosphate group (e.g., phosphoenol pyruvate (PEP), ATP, or creatine phosphate), where the energy source is present in the platform at a concentration of greater than about 30 mM, 40 mM, 50 mM, 60 mM, 70 mM, 80 mM, or 90 mM (preferably greater than about 67 mM), but less than about 100 mM, or within a concentration range bounded by any of these values.

In some embodiments, the platform further comprises a source of potassium ($K^+$) (such as a potassium salt such as potassium glutamate), where the platform comprises potassium at a concentration greater than about 50 mM, 100 mM, 150 mM, 200 mM, 250 mM, 300 mM, 350 mM, 400 mM, or 450 mM (preferably about 300 mM), but less than about 500 mM, or within a concentration range bounded by any of these values.

In some embodiments, the platform further comprises a source of magnesium ($Mg2^+$) (such as a magnesium salt such as magnesium glutamate or magnesium acetate), where the platform comprises magnesium at a concentration greater than about 1 mM, 2 mM, 3 mM, 4 mM, 5 mM, 6 mM, 8 mM, 12 mM, 16 mM, 20 mM, 24 mM, 28 mM, 32 mM, 36 mM (preferably about 24 mM), but less than about 60 mM, or within a concentration range bounded by any of these values.

The disclosed platforms and cell extracts may be utilized in methods for preparing a sequence defined biopolymer or protein in vitro. The disclosed methods typically include translating in vitro a translation template (e.g., mRNA) encoding the sequence defined biopolymer or protein in the platform of any of the foregoing claims. Optionally, the disclosed methods may include transcribing a transcription template (e.g., DNA) in the platform to provide the translation template.

The disclosed methods may be performed under conditions that are suitable for cellular extracts prepared from species of Clostridia. In some embodiments, the disclosed methods are performed at a temperature between about 20-40° C., and preferably at a temperature of about 30° C.

The disclosed methods may be performed to synthesize any sequence defined biopolymer or protein. In some embodiments, the sequence defined polymer or protein is a therapeutic protein and/or the method may be utilized to identify therapeutic proteins or biomaterials by translating a library of transcription templates. In some embodiments, the disclosed methods may be performed to optimize in vitro translation conditions for a cellular extract prepared from species of Clostridia.

Kits also are contemplated herein. In some embodiments, the contemplated kits comprise as components: (a) a cellular extract prepared from a cell culture of a species of Clostridia (e.g., *Clostridium autoethanogenum*); and (b) a reaction mixture for translating an mRNA. Suitable components for the reaction mixture of the disclosed kits may include, but are not limited to, amino acids which optionally may include noncanonical amino acids, NTPs, salts (e.g., sodium salts, potassium salts, and/or magnesium salts), cofactors (e.g., nicotinamide adenine dinucleotide (NAD) and/or coenzyme-A (CoA)), an energy source and optionally an energy source comprising a phosphate group (e.g., ATP or creatine phosphate).

Knock-Out Mutations

The species of Clostridia disclosed herein may include a genetic knock-out mutation, preferably a knock-out mutation that downregulates or eliminates a negative protein effector for CFPS. In certain embodiments, the at least one additional genetic knock-out mutation improves DNA stability, RNA stability, protein stability, amino acid stability, energy supply, or any combination thereof. In certain embodiments, the at least one additional genetic knock-out mutation comprises 1, 2, 3, 4, or more than 4 genetic knock-out mutations. In embodiments where the strain comprises 2 or more genetic knock-out mutations, at least 2 of the genetic knock-out mutations may both improve the same attribute, improved DNA stability, improved RNA stability, improved protein stability, improved amino acid stability, improved energy supply, or may both improve different attributes.

To improve DNA or RNA stability, the at least one additional genetic knock-out mutation may target the functional inactivation of nucleases. In vivo, nucleases play important roles in regulating DNA and mRNA turnover. However, their presence in crude cell extracts is expected to be deleterious, leading to template instability and reaction termination. A nonexhaustive list of potential negative effectors that have been identified in *E. coli* follow: RNase A (encoded by ma) degrades RNA by catalyzing the cleavage of phosodiester bonds, and identification of strains (e.g., MRE600, A19) lacking ma was important for early studies in in vitro translation. RNase II (encoded by rnb) is responsible for mRNA decay by 3' to 5' exonuclease activity, and cell extracts lacking RNase II exhibit a 70% increase in CFPS efficiency. RNase E (encoded by me) is part of a cold shock degradosome that induces mRNA decay in cold shock, which the cells experience during harvest prior to extract generation. MazF (encoded by mazF) is a toxin that degrades mRNA by sequence-specific (ACA) endoribonuclease activity, which could affect transcript stability. CsdA (encoded by csdA) is part of a cold shock degradosome along with RNase E and induces mRNA decay in cold shock, which the cells experience during harvest prior to extract generation. DNA-specific endonuclease I (encoded by endA) breaks double-stranded DNA, and its deletion has previously shown to be important for extending the duration of CFPS reactions. The corresponding Clostridia homolog of these and other nucleases may be functionally inactivated by the at least on additional genetic knock-out mutation.

To improve protein stability, the at least one additional genetic knock-out mutation may target the functional inactivation of proteases. In vivo, these proteases play important roles in regulating protein turnover. However, their presence in CFPS reactions is expected to be deleterious, leading to protein instability issues. A nonexhaustive list of potential negative effectors identified in $E.\ coli$ follow: Glutathione reductase (encoded by gor) reduces oxidized glutathione to maintain a reducing environment in the cytoplasm of a cell, making synthesis of disulfide-bonded proteins problematic. Lon (encoded by lon) is an ATP-dependent protease that demonstrated improved protein production in cell-free systems in BL21 strains upon transcriptional down regulation. Outer membrane protease VII (encoded by ompT) demonstrates specificity for paired basic residues and has been shown to stabilize proteins during CFPS upon removal. The corresponding Clostridia homolog of these and other proteases may be functionally inactivated by the at least on additional genetic knock-out mutation.

The at least one additional genetic knock-out mutation may target proteins known to negatively affect amino acid or energy supply. In vivo, these proteins play important roles in metabolism and substrate turnover. However, their presence in crude cell extracts is expected to be deleterious, leading to decreased amino acid and energy supply to support translation. A nonexhaustive list of potential negative effectors identified in $E.\ coli$ follow. Glutamate dehydrogenase (encoded by gdhA) catalyzes the deamination of glutamate, which may affect glutamate's stability. Glutamate-cysteine-ligase (encoded by gshA) catalyzes the first step of glutathione synthesis and may decrease the stability of cysteine. Serine deaminase I (encoded by sdaA) and serine deaminase II (encoded by sdaB) are two of the three enzymes involved in serine degradation. Arginine decarboxylase (encoded by speA) consumes arginine in the biosynthetic production of putrescine. Tryptophanase (encoded by tnaA) consumes tryptophan in the production of indole. Lastly, glycerol kinase (encoded by glpK) consumes ATP to phosphorylate glycerol, which could help deplete the energy supply required for cell-free reactions. The corresponding Clostridia homolog of these and other proteins may be functionally inactivated by the at least on additional genetic knock-out mutation.

Strains having at least one additional genetic knock-out mutation, may be prepared by any method of engineering a strain to functionally inactivate the negative effector to lessen or eliminate the negative effector from a lysate prepared from the strain. In certain embodiments, the genetic knock-out mutations may be prepared by inserting either a nonsense mutation and/or a frameshift mutation into the genome of the strain as well as deleting a vital portion of a gene coding sequence. In certain embodiments, the genetic knock-out mutations may be prepared by removing regulatory sequences (i.e. promoter, ribosome binding site) or otherwise changing these sequences in the genome as to render them non-functional. In certain embodiments, negative effectors can be functionally knocked out in lysates by introducing a unique affinity tag and subsequently using the tag to selectively remove the effector protein from the lysates. In certain embodiments a strain having at least one additional genetic knock-out, knock-down or disruption mutation may be prepared by multiplex automated genome engineering (MAGE), λ-Red recombinase-mediated recombination (Datsenko-Wanner), zinc-finger nucleases (ZFNs), transcription activator-like effector nucleases (TALENs), clustered regularly interspaced short palindromic repeats (CRISPR)-associated protein-9 nuclease (Cas9), homologous recombination, intron-based disruption and any other commonly used recombineering and genome engineering tools. Genetic tools for gene knock-outs/downs or disruption in Clostridia are known in the art. (See, e.g., Joseph et al., "Recent Developments of the Synthetic Biology Toolkit for $Clostridium$," Front. Microbiol., 2018; 9: 154; and Liew et al., "Gas Fermentation—A Flexible Platform for Commercial Scale Production of Low-Carbon-Fuels and Chemicals from Waste and Renewable Feedstocks," Front. Microbiol. 11 May 2016, 1-29; the contents of which are incorporated herein by reference in their entireties).

Upregulated Gene Products

The species of Clostridia disclosed herein may be engineered to express an additional upregulated gene product. The at least one additional upregulated gene product is preferably an upregulated gene product that is a positive effector for CFPS. In certain embodiments, the at least one additional upregulated gene product improves energy supply, chaperone levels, translations function, ribosome recycling, or any combination thereof. In certain embodiments, the at least on additional upregulated gene product comprises 1, 2, 3, 4, or more than 4 upregulated gene products. In embodiments where the strain comprises 2 or more upregulated gene products, at least 2 of the upregulated gene products may both improve the same attribute, improved energy supply, improved chaperone levels, improved translation function, or improved ribosome recycling, or may both improve different attributes.

To improve energy supply, the at least one additional upregulated gene product may target the upregulation of kinases. In vivo, these proteins play important roles in metabolism and the transfer of phosphate groups. The upregulated presence in crude cell extracts is expected to improve energy supply to support translation. A nonexhaustive list of potential positive effectors identified in $E.\ coli$ follow. Acetate kinase (encoded by ackA) increases the overall metabolic flux of metabolites toward substrate-level ATP generation. Nucleoside-diphosphate kinase (encoded by ndk) facilitates the synthesis of NTPs from their corresponding NDPs. Pyruvate kinase monomer (encoded by pykF) helps drive ATP generation. The corresponding Clostridia homolog of these and other kinases may be the at least one additional upregulated gene product.

To improve energy supply, the at least one additional upregulated gene product may target the upregulate of deaminases. In vivo, these proteins may play important roles in metabolism and preparing metabolites. A nonexhaustive list of potential positive effectors identified in $E.\ coli$ follow. Cytidine deaminase (encoded by cdd) initiates the deamination of cytidine which may lead to the synthesis of UTP.

The corresponding Clostridia homolog of these and other deaminases may be the at least one additional upregulated gene product.

To improve chaperone levels, the at least one upregulated gene product may target the upregulation of isomerases, foldases and/or holdases. In vivo, these proteins may play important roles in the assisting proteins to adopt functionally active conformations. The upregulated presence in crude cell extracts is expected to improve chaperone levels to support protein production into soluble and/or active confirmations. A nonexhaustive list of potential positive effectors identified in E. coli follow. Disulfide bond isomerase (encoded by dsbC) shuffles disulfide bonds into correct positions. Chaperone protein DnaK (encoded by dnaK) aids the folding of nascent polypeptide chains and the rescue of misfolded proteins. Chaperone protein DnaJ (encoded by dnaJ) stimulates the ATPase activity of DnaK. Protein GrpE (encoded by grpE) stimulates the ATPas activity of DnaK. Trigger Factor (encoded by tig) aids the folding of nascent polypeptides. The 10 kDa chaperonin subunit (encoded by groS) forms part of the GroEL-GroES chaperonin complex that aids in protein folding. The 60 kDa chaperonin subunit (encoded by groL) forms part of the GroEL-GroES chaperonin complex that aids in protein folding. The corresponding Clostridia homolog of these and other isomerases, foldases, and/or holdases may be the at least one additional upregulated gene product.

To improve translation function, the at least one upregulated gene product may target the upregulation of initiation factors and/or elongation factors. In vivo, these proteins play important roles in the translation function. The upregulated presence in crude cell extracts is expected to improve translation function. A nonexhaustive list of potential positive effectors identified in E. coli follow. Translation initiation factor IF-1 (encoded by infA) interacts with the 30S ribosomal subunit to initiate translations. Translation initiation faction IF-2 (encoded by infB) has a role in the proper placement of the charged initiator fMet-tRNA via a GTP-dependent mechanism. Elongation factor G (encoded by fusA) facilitates translocation of the ribosome by one codon along a mRNA. Elongation factor P (encoded by efp) stimulates the synthesis of peptide bonds. Elongation factor 4 (encoded by lepA) can alter the rate of translation, leading to increases in the rate of translation under certain stress conditions. Elongation factor TU 2 (encoded by tufB) helps shuttle charged tRNAs to ribosomes. The corresponding Clostridia homolog of these and other initiation factors and/or elongation factors may be the at least one additional upregulated gene product.

To improve translation function, the at least one upregulated gene product may target the upregulation of recycling factors. In vivo, these proteins play important roles in the ribosome recycling. The upregulated presence in crude cell extracts is expected to improve ribosome recycling. A nonexhaustive list of potential positive effectors identified in E. coli follow. Heat shock protein 15 (encoded by hslR) is involved with the recycling of free 50S ribosomal subunits. Ribosome-recycling factor (encoded by frr) promotes rapid recycling of ribosomal subunits after the release of the polypeptide chain. The corresponding Clostridia homolog of these and other recycling factors may be the at least one additional upregulated gene product.

Strains having at least one additional genetic knock-out mutation, may be prepared by any method of engineering a strain to functionally increase a positive effector to increase the presence of the positive effector in the lysate prepared from the strain. In certain embodiments, the upregulated gene product is expressed from a plasmid present in the GRO and/or expressed from an integration site in GRO genome. Additionally, gene upregulation may be enhanced by engineering the promoter and/or ribosome binding site in front of your gene of interest located either on a plasmid or on the genome. A stronger promoter/ribosome binding site would lead to an increase in transcriptional activity. Techniques commonly employed to integrate a plasmid overexpressing a positive effector into a strain includes transformation. Techniques commonly employed to integrate a gene cassette containing a positive effector into the genome for overexpression includes X-Red recombinase-mediated recombination (Datsenko-Wanner). Genetic tools for gene knock-outs/downs or disruption in Clostridia are known in the art. (See, e.g., Joseph et al., "Recent Developments of the Synthetic Biology Toolkit for *Clostridium*," Front. Microbiol., 2018; 9: 154; and Liew et al., "Gas Fermentation—A Flexible Platform for Commercial Scale Production of Low-Carbon-Fuels and Chemicals from Waste and Renewable Feedstocks," Front. Microbiol. 11 May 2016, 1-29; the contents of which are incorporated herein by reference in their entireties).

Genomically Recoded Organisms

An aspect of the present invention is a genomically recoded organism (GRO) which optionally may be a strain deficient in release factor 1 (RF1) or a genetic homolog thereof. GROs may be prepared by any method of strain engineering. In certain embodiments, a strain deficient in RF1 is prepared by replacing in the strain all instances of the UAG codon, permitting the deletion of release factor 1 (RF1; terminates translation at UAG and UAA) and, hence, eliminating translational termination at UAG codons. This GRO allows for the reintroduction of UAG codons, along with orthogonal translation machinery to permit efficient and site-specific incorporation of nonstandard or noncanonical amino acids into proteins. That is, UAG may be transformed from a nonsense codon (terminates translation) to a sense codon (incorporates amino acid of choice), provided the appropriate translation machinery is present.

ILLUSTRATIVE EMBODIMENTS

Provided below are several illustrative embodiments of the subject matter disclosed herein. These illustrative embodiments are not intended to limit the claims in any way.

Embodiment 1

A cell-free protein synthesis platform for in vitro transcription of mRNA, and/or translation of polypeptides, the platform comprising as a component a cellular extract prepared from a cell culture of a species of Clostridia.

Embodiment 2

The platform of embodiment 1, wherein the species of Clostridia is selected from *Clostridium autoethanogenum, Clostridium ljungdahlii, Clostridium butyricum, Clostridium beijerinckii, Clostridium pasteurianum, Clostridium saccharoperbutylacetonicum, Clostridium aceticum, Clostridium tetanomorphum, Clostridium phytofermentans, Clostridium arbusti, Clostridium akagii, Clostridium cellulovorans, Clostridium diolis, Clostridium acetireducens, Clostridium coskatii, Clostridium ragsdalei, Clostridium drakei, Clostridium formicoaceticum, Clostridium scatalogenes, Clostridium kluyveri, Clostridium tyrobutyricum, Clostridium grantii, Clostridium*

*homopropionicum, Clostridium tepidiprofundi, Clostridium collagenovorans, Clostridium tunisiense, Clostridium argentinense, Clostridium ihumii, Clostridium cadaveris, Clostridium amylolyticum, Clostridium sartagoforme, Clostridium baratii, Clostridium paraputrificum, Clostridium fallax, Clostridium cavendishii, Clostridium cylindrosporum, Clostridium phoceensis, Clostridium botulinum, Clostridium dificile, Clostridium tetani, Clostridium sordelli, Clostridium perfringes, Clostridium novyi, Clostridium septicum, Clostridium sordelli, Clostridium histolyticum, Clostridium perfringens, Clostridium sporogenes, Clostridium ramosum, Clostridium innocuum, Clostridium clostridioforme, Clostridium tertium*, and *Clostridium oedematiens.*

Embodiment 3

The platform of embodiment 1 or 2, wherein the species of Clostridia is *Clostridium autoethanogenum.*

Embodiment 4

The platform of any of the foregoing embodiments, wherein the species of Clostridia is engineered to be deficient in a negative effector for cell-free protein synthesis (CFPS).

Embodiment 5

The platform of embodiment 4, wherein the negative effector for CFPS is selected from the group consisting of the Clostridia homolog of *E. coli* endA, mazF, rna, rnb, rne, gor, lon, ompT, gdhA, gshA, sdaA, sdaB, speA, WaaL, tnaA, glpK, and any combination thereof.

Embodiment 6

The platform of any of the foregoing embodiments, wherein the species of Clostridia is engineered to express an upregulated gene product that is a positive effector for CFPS.

Embodiment 7

The platform of embodiment 6, wherein the positive effector for CFPS is selected from the group consisting of the Clostridia homolog of *E. coli* ackA, ndk, pykF, cdd, dsbC, dnaK, dnaJ, crpE, tig, groS, groL, infA, infB, fusA, efp, lepA, tufB, hslR, ffr, and any combination thereof.

Embodiment 8

The platform of any of the foregoing embodiments, wherein the species of Clostridia is engineered to be deficient in a release factor 1.

Embodiment 9

The platform of any of the foregoing embodiments, wherein the species of Clostridia has been engineered to express T7 RNA polymerase.

Embodiment 10

The platform of any of the foregoing embodiments, wherein the cell culture is in stationary phase.

Embodiment 11

The platform of embodiment 10, wherein stationary phase is defined as the cell culture having an $OD_{600}$ of greater than about 3.0.

Embodiment 12

The platform of any of the foregoing embodiments, wherein the cellular extract comprises an S12 fraction and/or S30 fraction of the cell culture.

Embodiment 13

The platform of any of the foregoing embodiments further comprising one or more of: (i) a reaction buffer; (ii) an RNA polymerase; and (iii) a transcription template, wherein the RNA polymerase is capable of transcribing the transcription template to form a translation template and the cellular extract can sustain protein synthesis through a combined transcription/translation reaction.

Embodiment 14

The platform of any of the foregoing embodiments further comprising one or more components selected from the group consisting of: (i) amino acids which optionally may include non-canonical amino acids and optionally at a concentration between about 0.5-4.0 mM and preferably about 2 mM; (ii) NTPs; (iii) salts optionally at a total concentration of between about 50-400 mM; (iv) a macromolecular crowding agent which optionally is polyethylene glycol or Ficol; (iv) cofactors; (v) an energy source and optionally an energy source comprising a phosphate group (such as phosphoenol pyruvate (PEP)); (vi) a translation template; (vii) a transcription template; (viii) a DNA-dependent RNA polymerase (e.g., T7 RNA polymerase); and (ix) any combination thereof.

Embodiment 15

The platform of any of the foregoing embodiments further comprising an energy source and optionally an energy source comprising a phosphate group (such as phosphoenol pyruvate (PEP)), wherein the energy source is present at a concentration of greater than about 30 mM, 40 mM, 50 mM, 60 mM, 70 mM, 80 mM, or 90 mM (preferably greater than about 67 mM), but less than about 100 mM, or within a concentration range bounded by any of these values.

Embodiment 16

The platform of any of the foregoing embodiments further comprising a source of potassium ($K^+$), wherein the platform comprises potassium at a concentration greater than about 10 mM, 20 mM, 30 mM, or 50 mM, but less than about 500 mM, 400 mM, 300 mM, or 200 mM, or within a concentration range bounded by any of these values preferably about 100 mM; and/or the platform of any of the foregoing claims further comprising a source of magnesium ($Mg^+$), wherein the platform comprises magnesium at a concentration greater than about 1 mM, 2 mM, 3 mM, 4 mM, 5 mM, 6 mM, 8 mM, 12 mM, 16 mM, 20 mM, 24 mM, or 28 mM, but less than about 60 mM, 56 mM, 52 mM, 48 mM, 44 mM, 40 mM, or 36 mM, or within a concentration range bounded by any of these values, preferably about 32 mM.

Embodiment 17

The platform of any of the foregoing embodiments, wherein the entirety of the platform or one or more components thereof are preserved by freeze-drying.

Embodiment 18

The platform of any of the foregoing embodiments, wherein the cellular extract is prepared by a method that includes one or more of the following steps: (i) cell suspension and lysis (e.g., via sonication); (ii) a run-off reaction; and (iii) dialysis.

Embodiment 19

A method for in vitro transcription of mRNA and/or in vitro translation of mRNA to prepare a polypeptide, the method comprising transcribing the mRNA from a transcription template and/or translating an mRNA in the platform of any of the foregoing embodiments.

Embodiment 20

The method of embodiment 19, wherein the method comprises transcribing a DNA template in the platform to provide the translated mRNA.

Embodiment 21

The method of embodiment 19 or 20, wherein the DNA template encodes an mRNA that includes modifications that facilitate efficient transcription and/or translation, optionally wherein the modification are present in the 5'-UTR, the 3'UTR, or both.

Embodiment 22

The method of any of embodiments 19-21, wherein the method is performed at a temperature between about 20-40° C.

Embodiment 23

The method of any of embodiments 19-22, wherein the method is performed as a batch reaction.

Embodiment 24

The method of any of embodiments 19-22, wherein the method is performed as a semi-continuous reaction.

Embodiment 25

The method of any of embodiments 19-22, wherein the method is performed as a continuous reaction.

Embodiment 26

The method of any of embodiments 19-25, wherein the method is performed under anaerobic conditions.

Embodiment 27

The method of any of embodiments 19-25, wherein the method is performed under aerobic conditions.

Embodiment 28

A kit comprising as component: (a) a cellular extract prepared from a cell culture of a species of Clostridia; and (b) a reaction mixture for transcribing and/or translating an mRNA, optionally wherein the species of Clostridia is *Clostridium autoethanogenum*.

Embodiment 29

The kit of embodiment 28, wherein the reaction mixture comprises one or more components selected from the group consisting of: (i) amino acids which optionally may include non-canonical amino acids; (ii) NTPs; (iii) salts; (iv) cofactors; (v) an energy source and optionally an energy source comprising a phosphate group (such as phosphoenol pyruvate (PEP)); and (vi) any combination thereof.

Embodiment 30

A recombinant species of Clostridia, optionally *Clostridium autoethanogenum*, wherein the species of Clostridia is engineered to be deficient in a negative effector for cell-free protein synthesis (CFPS).

Embodiment 31

The recombinant species of Clostridia of embodiment 30, wherein the negative effector for CFPS is selected from the group consisting of the Clostridia homolog of *E. coli* endA, mazF, rna, rnb, rne, gor, lon, ompT, gdhA, gshA, sdaA, sdaB, speA, WaaL, tnaA, glpK, and any combination thereof.

Embodiment 32

The recombinant species of Clostridia of embodiment 30 or 31, wherein the species of Clostridia is engineered to express an upregulated gene product that is a positive effector for CFPS.

Embodiment 33

The recombinant species of Clostridia of embodiment 32, wherein the positive effector for CFPS is selected from the group consisting of the Clostridia homolog of *E. coli* ackA, ndk, pykF, cdd, dsbC, dnaK, dnaJ, crpE, tig, groS, groL, infA, infB, fusA, efp, lepA, tufB, hslR, ffr, and any combination thereof.

Embodiment 34

The recombinant species of Clostridia of any of embodiments 30-33, wherein the species of Clostridia is engineered to be deficient in a release factor 1.

Embodiment 35

The recombinant species of Clostridia of any of embodiments 30-34, wherein the species of Clostridia has been genomically-recoded to replace one or more stop codons with a different codon.

Embodiment 36

The recombinant species of Clostridia of any of embodiments 30-35, wherein the species of Clostridia has been engineered to express T7 RNA polymerase.

Embodiment 37

A method for identifying and characterizing genetic parts of Clostridia and gene expression of Clostridia used for transcription and/or translation, the method comprising: (a) creating a test library of genetic parts of Clostridia or variant gene sequences of Clostridia (e.g., one or more of test promoters, test terminators, test ribosome binding sites, and the like); and (b) testing the genetic parts of the test library and/or an alternative codon expressed in a platform comprising: (i) a cellular extract prepared from Clostridia; and (ii) a reaction mixture for transcribing and/or translating an mRNA

EXAMPLES

The following Examples are illustrative and should not be interpreted to limit the scope of the claimed subject matter.

A. Abstract

Clostridia are industrially proven microbes with exceptional substrate flexibility and metabolite diversity as well as tolerance to metabolic end-products and contaminants, making them suitable for many metabolic engineering applications. Gas-fermenting clostridia are particularly attractive for sustainable biochemical production because of their potential to convert waste carbon into low-cost fuels and high-value compounds. Unfortunately, designing and engineering these non-model organisms remains laborious and costly. In efforts to accelerate strain engineering we have developed a simple, robust, and high-yielding aerobic clostridia cell-free system to prototype enzyme expression for metabolic pathway engineering in vitro. Here, we present a systematic optimization of extract preparation and processing as well as cell-free reaction conditions to enable prototyping of clostridia-specific promoters, coding sequences, and metabolism. Our system is derived from the industrially-relevant anaerobe, *Clostridium autoethanogenum*, and produces >200 μg/mL of active luciferase in batch reactions and >300 μg/mL in semi-continuous reaction mode. This easy to use system that does not require anaerobic conditions provides an excellent platform for prototyping oxygen-independent metabolic engineering efforts in clostridia such as transcription and translation and metabolic pathways comprised of oxygen-resistant enzymes, which will expand the clostridia metabolic engineering "toolbox" and accelerate clostridia strain engineering efforts.

B. Introduction

Microbes can be engineered to produce biofuels and high-value compounds such as chemicals, materials, and therapeutics (Keasling, 2012; Nielsen and Keasling, 2016), to address modern challenges like rapid population growth, an increase in energy demand, and waste generation (Nielsen et al., 2014). However, even the most advanced design-build-test cycles for optimizing a given compound's biosynthetic pathway in model organisms such as *Escherichia coli* and yeast are still on the order of weeks to months, and process-based challenges associated with these organisms remain (e.g., limited substrate range, cost of added enzymes, reduced yields through $CO_2$ losses, susceptibility to contamination, and genetic instability) (Keasling, 2012; Nielsen and Keasling, 2016). These challenges have prevented a more rapid commercialization of new bioproduct manufacturing processes, with only a handful successfully commercialized to date apart from ethanol fermentation (Meadows et al., 2016; Nakamura and Whited, 2003; Nielsen et al., 2014; Yim et al., 2011). Additionally, *E. coli* and yeast intrinsically lack certain cellular traits which limits the diversity of reaction space and ultimately products that can be made. As such, most industrial bioprocesses (e.g., synthesis of amino acids (Leuchtenberger et al., 2005), acetone-butanol-ethanol (ABE) (Jiang et al., 2015; Jones, 2005), organic acids (Ghaffar et al., 2014; Rodriguez et al., 2014; Wee et al., 2006) rely on other organisms.

Clostridia are one such group of organisms, which are industrially proven and have exceptional substrate and metabolite diversity, as well as tolerance to metabolic end-products and contaminants (Tracy et al., 2012). Industrial, large-scale fermentations with clostridia have been carried out for over 100 years with the ABE fermentation being the second largest industrial fermentation process only behind ethanol fermentation (Jones, 2005). In addition to ABE clostridia (solventogenic), there are also clostridia species that are able to degrade lignocellulosic biomass (cellulolytic) and species that are capable of autotrophic growth on C1 substrates, such as carbon monoxide (CO) and $CO_2$ (acetogenic) (Tracy et al., 2012). Gas fermentation with acetogenic clostridia offers an attractive route for conversion of syngas that can be generated from any biomass resource (e.g. agricultural waste or unsorted and non-recyclable municipal solid waste) and industrial waste resources (e.g. off-gases from steel mills, processing plants or refineries) to fuels and chemicals. However, the current state-of-the-art strain engineering for clostridia remains a low-throughput, labor-intensive endeavor. Specific challenges include organism-specific genetic constraints (Daniell et al., 2015; Joseph et al., 2018; Liew et al., 2016, 2017; Nagaraju et al., 2016), the requirement of an anaerobic environment, and, in case of acetogens, handling of gases. As a result, developments in clostridia biotechnology and basic knowledge of clostridia biology have lagged behind achievements in aerobic prokaryotic and eukaryotic biology. New robust tools are needed to study clostridia and speed up the designing, building, and testing of biological processes in these organisms.

Extract-based cell-free systems are emerging as powerful platforms for synthetic biology applications such as metabolic engineering (Bujara et al., 2011; Carlson et al., 2012; Dudley et al., 2019; Hodgman and Jewett, 2012; Karim et al., 2019; Karim and Jewett, 2016; Kelwick et al., 2017; Morgado et al., 2018). Assembling metabolic pathways in the cell-free environment has been done traditionally by assembling purified enzymes and substrates. However, the development of cell-free protein synthesis (CFPS) systems has transformed the way pathways can be built and tested. These systems consist of crude cell extracts, energy substrates, co-factors and genetic instructions in the form of DNA, and facilitate the activation, manipulation and usage of cellular processes in a test tube. While cell-free systems have historically been used to study fundamental biology (e.g., the genetic code) (Nirenberg and Matthaei, 1961), recent development of cell-free protein synthesis capabilities (Caschera and Noireaux, 2014; Jewett et al., 2008; Jewett and Swartz, 2004) has expanded the application space to include bulk production of recombinant proteins (Garamella et al., 2016; Jaroentomeechai et al., 2018; Kwon et al., 2013), paper-based diagnostics (Gootenberg et al., 2017; Pardee et al., 2016, 2014; Salehi et al., 2017; Takahashi et al., 2018), on-demand biomanufacturing (Karig et al., 2017; Pardee et al., 2016; Sullivan et al., 2016), prototyping of genetic parts (Chappell et al., 2013; Marshall et al., 2018; Moore, Simon J.; MacDonald, James T.; Wienecke, Sarah; Ishwarbhai, Alka; Tsipa, Argyro; Aw, Rochelle; Kylilis, Nicolas; Bell, David J., McClymont, David W.; Jensen, Kirsten; Polizzi, Karen M.; Biedendieck, Rebekka; Freemont, 2018; Siegal-Gaskins et al., 2014; Melissa K Takahashi et al., 2015; Melissa K. Takahashi et al., 2015; Yim et al., 2019) and studying whole metabolic pathways (Bujara et al., 2011; Dudley et al., 2019; Karim et al., 2019; Karim and Jewett, 2016; Kelwick et al., 2017). These systems have three key advantages: First, these systems lack a cell wall, and thereby allow active monitoring, rapid sampling and direct manipulation, facilitating an unprecedented freedom of design to control, modify, and engineer a desired bioprocess. Second, because genetic instructions can be simply added to CFPS reactions in form of plasmid DNA or linear PCR products, they circumvent laborious cloning and transformation steps, and can thereby facilitate testing of genetic designs within a few hours instead of several days or weeks. Third, this approach does not rely on time-consuming enzyme purification procedures but rapidly builds and tests metabolic pathways directly in cell extracts by synthesizing required enzymes in vitro (Karim et al., 2018; Karim and Jewett, 2016).

Cell-free systems have mostly been developed using *E. coli* and other model organism extracts until recently. This is important because the scope of extract-based CFPS applications is predefined by the chosen source organism and the biochemical resources present at the time of cell harvest and extract preparation. This means that metabolic enzymes, cellular machineries like the translation system, and co-factor and energy regeneration systems, unique to a chassis organism are also unique that organism's extract. The most exploited CFPS systems are from *E. coli* (bacterium) (Carlson et al., 2012; Hodgman and Jewett, 2012), wheat germ (plant) (Madin et al., 2000; Takai et al., 2010), *Spodoptera frugiperda* (insect) (Ezure et al., 2010; Tarui et al., 2001), and rabbit reticulocytes (mammal) (Anastasina et al., 2014; Kobs, 2008; Pelham and Jackson, 1976), with others being developed (Ferrer-Miralles et al., 2009; Gan and Jewett, 2014; Hodgman and Jewett, 2013), (Kovtun et al., 2010; Mureev et al., 2009), (Brödel et al., 2014; Martin et al., 2017), (Wang et al., 2018) (Mikami et al., 2010) (Kelwick et al., 2016). However, CFPS systems derived from non-model organisms have only recently been developed, most notably from species of archeae (Endoh et al., 2008, 2007, 2006), *Bacillus* (Moore, Simon J.; MacDonald, James T.; Wienecke, Sarah; Ishwarbhai, Alka; Tsipa, Argyro; Aw, Rochelle; Kylilis, Nicolas; Bell, David J., McClymont, David W.; Jensen, Kirsten; Polizzi, Karen M.; Biedendieck, Rebekka; Freemont, 2018), *Streptomyces* (Li et al., 2018, 2017), and *Vibrio* (Des Soye et al., 2018; Failmezger et al., 2018; Wiegand et al., 2018). To date no clostridia cell-free system exists that produces protein yields sufficient for prototyping genetic parts and metabolic pathways. Studying clostridia biosynthetic pathways in cell-free systems has been limited to translating *E. coli* cell-free results to clostridia cellular performance (Karim et al., 2019). Though these efforts can successfully inform clostridia strain engineering attempts, they are limited due to the difference between *E. coli* and clostridia metabolism present in the extract. We hypothesize that a cell-free platform based on clostridia extracts will further improve predictions about successful pathway designs, as those extracts might mimic the organism's natural metabolism better.

Here, we present the first easy-to-use, robust and high-yielding clostridia CFPS platform derived from an industrially relevant strain, *Clostridium autoethanogenum*, that facilitates cell-free synthetic biology applications. We started developing the clostridia CFPS system by using extract preparation and CFPS reaction conditions optimal for the *E. coli* system and clostridia codon-adapted firefly luciferase as reporter protein. We then adapted extract preparation and CFPS reaction conditions to attune to clostridia extracts by systematically optimizing key parameters of both steps. Finally, we demonstrate the capability of our system for clostridia-specific prototyping: clostridia genetic parts by expressing luciferase from constructs under the control of endogenous promoters+5'UTRs derived from clostridia metabolic enzymes or by utilizing different gene coding sequences, as well as activity of clostridia metabolic pathways in the extracts (FIG. 1). Our system produces >200 µg/mL of active luciferase in batch reactions and >300 µg/mL in semi-continuous reaction mode, enables detection of gene expression differences arising from using different endogenous promoters or coding sequences and shows metabolic activity in clostridia glycolysis/gluconeogenesis and connected pathways. To our knowledge, the presented system is the first high-yielding and robust CFPS system derived from an obligate anaerobic bacterium. Its capability of prototyping oxygen-insensitive bioprocesses under aerobic conditions can ease and speed-up metabolic engineering efforts for bioprocess development in clostridia.

C. Results and Discussion

Developing a system capable of cell-free protein synthesis (CFPS) from a new organism requires optimization at several levels. The choice of organism, fermentation conditions, extract preparation and processing, and cell-free reaction conditions each play an important role in a CFPS platform. In this work, we aimed to develop the first, simple, robust, and high-yielding clostridia-derived CFPS system using an industrially relevant clostridia strain as our source organism, *C. autoethanogenum*. Based on extensive optimization that has gone into establishing anaerobic fermentation conditions for this organism (Heijstra et al., 2017; Valgepea et al., 2017), we chose to fix microbial growth and harvest conditions. Here, we describe (1) establishing the aerobic, clostridia-based cell-free system, (2) identifying beneficial extract processing steps, and (3) optimizing reaction conditions to enable prototyping of clostridia-based genetic parts and metabolism in the cell-free environment.

1. Optimizing Mg(Glu)$_2$ Concentrations in CFPS Using *C. autoethanogenum* Extracts We started development of *C. autoethanogenum*-based cell-free systems by exploring the CFPS capability when prepared under aerobic conditions and using extract preparation and CFPS conditions of the high-yielding BL21 *E. coli* system (Kwon and Jewett, 2015). In brief, we resuspended *C. autoethanogenum* cells in buffer containing acetate salts, lysed them by sonication using 640 J total sonication input energy per mL cell suspension, and centrifuged them at 12,000×g to clarify the lysate (FIG. 2A, left panel). The resulting extract was used for CFPS at 30° C. driven by the PANOx-SP energy regeneration system (Jewett and Swartz, 2004) and containing 8 mM Mg(Glu)$_2$, 33 mM phosphoenolpyruvate (PEP), 2 mM of all cognate amino acids, 100 mM reduced nicotinamide adenine dinucleotide (NAD$^+$) and 50 mM coenzyme A (CoA) (FIG. 2A, middle). We chose firefly luciferase as reporter protein, as it has been demonstrated in clostridia (Feustel et al., 2004) and its expression can be detected via a highly sensitive bioluminescence assay and not only demonstrates the extract's capability for protein synthesis but also for proper folding. For this, we cloned a clostridia-codon-adapted variant of the firefly luciferase gene into our CFPS expression vector pJL1 under control of the T7 promoter, added the construct to the CFPS reaction, and followed luciferase expression in CFPS by luminescence for 2.75 hours. While low amounts of luciferase were expressed, we observed a luminescence increase and decrease over the course of the reaction, demonstrating that some protein synthesis activity is present in the extract (FIG. 2A, right panel).

This result led us to perform an initial optimization of magnesium added to CFPS reactions as it has been shown to be one of the most critical factors in CFPS productivity (Des Soye et al., 2018; Hodgman and Jewett, 2013; Jewett and Swartz, 2004; Kwon and Jewett, 2015; Li et al., 2017; Martin et al., 2017; Wang et al., 2018). We setup CFPS reactions expressing luciferase for 2.75 hours adjusting the $Mg(Glu)_2$ concentrations between 8 mM and 36 mM. $Mg(Glu)_2$ concentrations of ≥20 mM markedly increased luciferase expression by more than five orders of magnitude (FIG. 2B) with the optimum at 32 mM $Mg(Glu)_2$. This result was surprising because the optimum for *E. coli* extracts tends to be in the range of 8 mM to 12 mM $Mg(Glu)_2$ (Jewett and Swartz, 2004; Kwon and Jewett, 2015). One major role that magnesium plays in cell-free reactions is to scavenge free inorganic phosphate (accumulated via phosphorylated energy sources) which can inhibit metabolic reactions driving protein expression. Without wishing to be bound by theory, we speculate that clostridia extracts could contain or generate more inorganic phosphate than *E. coli* extracts. Competitive, synergistic, or counteracting effects with other ions present in clostridia extracts, especially iron (a cofactor to many key enzymes), are likely another reason for needing such high concentrations of magnesium. These results proved promising to further develop the aerobic, clostridia extract-based CFPS system. We therefore sought to stepwise adjust extract preparation and CFPS conditions to improve cell-free performance.

Figure 3:
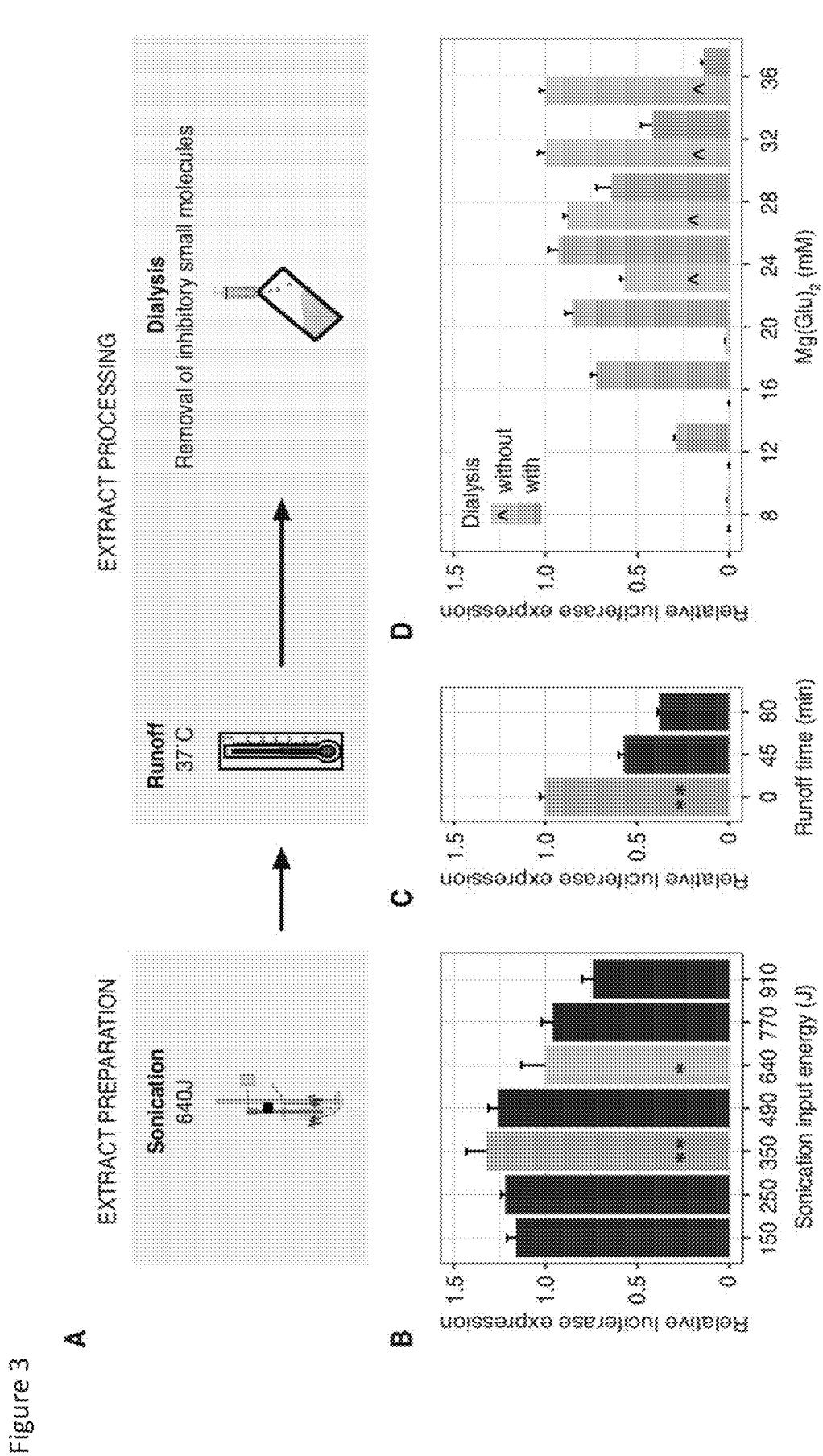
FIG. 3. Optimization of *C. autoethanogenum* extract preparation and processing. (A) Schematic diagram of the extract preparation workflow. (B-D) Relative maximum luciferase luminescence in vitro from *C. autoethanogenum* extracts during 4.25 h CFPS prepared using (B) indicated sonication input energies, (C) 350J sonication input energy and indicated runoff times, and (D) 350J sonication input energy without (the first bar in each set, ˆ) and with dialysis. For B and C, bars with one (*) or two (**) indicate previously and newly optimized condition, respectively. Luciferase expression was determined by bioluminescence and plotted as relative values compared to the maximal luciferase expression of the previously used condition. Data are presented as mean±s.d. of three independent reactions.

2. Adjusting Extract Preparation and Processing of *C. autoethanogenum* Increases CFPS Yields and Shifts the $Mg(Glu)_2$ Optimum Towards More Physiological Concentrations The quality of prepared crude cell extract, which is largely determined by how the cells are lysed (relevant proteins can be harmed during this process) and how the lysates are processed (i.e., run-off reactions, dialysis), has a significant effect on CFPS (Carlson et al., 2012; Gregorio et al., 2019; Kwon and Jewett, 2015). Work on CFPS systems such as *E. coli* (Kwon and Jewett, 2015; Silverman et al., 2019), *S. cerevisiae* (Hodgman and Jewett, 2013), and *V. natriegens* (Des Soye et al., 2018) has demonstrated that the extract's robustness and productivity can be improved by systematically optimizing each extract preparation and processing step. We therefore explored key parameters of both (FIG. 3A), starting with lysis conditions responsible for cell wall rupture. Using sonication as our lysis method due to its simple, reproducible, and inexpensive nature (Kwon and Jewett, 2015), we lysed 1 mL of resuspended *C. autoethanogenum* cells at different sonication input energies ranging from 250 J to 910 J at 50% amplitude for 10 sec on and 10 sec off (FIG. 3B). We clarified the lysates by centrifugation and tested the extract's capability for CFPS. Compared to the initially used 640 J, higher input energies reduced CFPS yields, while lower energies were beneficial. The optimum was 350 J, increasing luciferase expression by ~30%. Our results suggest that at input energies above 490 J ribosomes or other fragile cell components involved in protein synthesis are disrupted, harming the extract's CFPS activity.

Two common post-lysis processing steps, runoff and dialysis, can improve the quality of extracts for CFPS. The runoff involves incubating the extract at 37° C. which can increase the extract's protein synthesis productivity (Kwon and Jewett, 2015). The extra time at a physiological temperature potentially enables ribosomes to "run off" native mRNAs which might then be degraded by endogenous RNases while the ribosomes are freed-up for synthesis of recombinant proteins (Jermutus et al., 1998; Nirenberg and Matthaei, 1961). To test the effect of a runoff step, we incubated the clarified lysates after sonication at 37° C. for a short (45 min) and a long (80 min) time, clarified them a second time by centrifugation and compared their protein synthesis activity. We found that the runoff markedly decreased luciferase expression (FIG. 3C). A runoff for 45 min almost halved luciferase amounts while longer incubation time (80 min) reduced yields to a third. Due to our observation of a relatively large pellet of insoluble material after centrifugation, we suspect that the CFPS reduction arises from the loss of unstable and oxygen-sensitive proteins that are directly or indirectly essential for protein synthesis (e.g. enzymes and co-factors in energy metabolism such as ferredoxin or the extremely oxygen sensitive pyruvate:ferredoxin oxidoreductase (Meinecke et al., 1989) or critical electron-bifurcating enzymes (Mock et al., 2015).

In contrast to runoff, dialysis changes the extract's composition by allowing exchange of small molecules between a dialysis buffer and the extract. If this step removes small inhibitory molecules from the extract such as inorganic phosphate, this step can be beneficial and increase CFPS yields (Gregorio et al., 2019; Silverman et al., 2019). To test the impact of dialysis, we dialyzed the clarified lysates after sonication three times for 45 min in S30 buffer at 4° C. and compared luciferase expression at several $Mg(Glu)_2$ concentrations. We found that dialysis did not significantly affect overall extract productivity but instead decreased the $Mg(Glu)_2$ optimum from 32 mM toward a more physiological concentration of 24 mM (FIG. 3D). We speculate that inorganic phosphate or molecules leading to its production during CFPS left the extract and thereby reduce the required magnesium to counteract their inhibitory effect. Based on these results, we next set out to optimize CFPS reaction conditions with an extract preparation and processing protocol that now includes dialysis.

Figure 4:
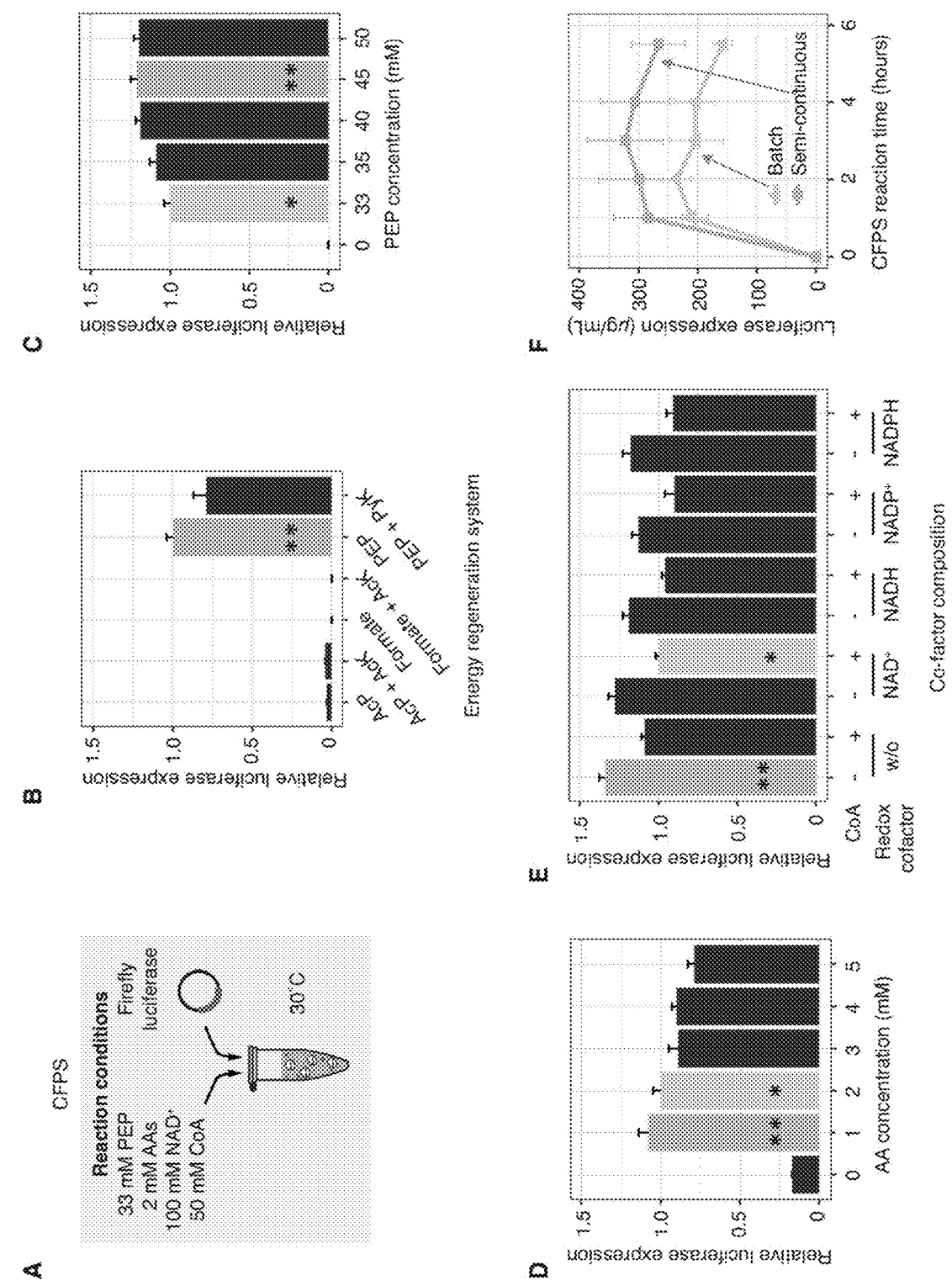
FIG. 4. Optimization of CFPS reaction conditions for *C. autoethanogenum* extracts. (A) Schematic diagram of a CFPS reaction depicting the concentrations of key CFPS components which were step-wise adjusted for *C. autoethanogenum* extracts-based CFPS. (B-H) Relative maximum luciferase luminescence in vitro from *C. autoethanogenum* extracts during CFPS at different reagent concentrations: (B) energy regeneration system, (C) PEP concentration, (D) amino acid concentration, (E) nicotinamide dinucleotide and coenzyme A cofactor composition, (F) plasmid DNA template concentration. Bars with one * or two ** indicate previously and newly optimized condition, respectively. Maximal luciferase expressions were determined by bioluminescence and plotted as relative values compared to the previously used condition (B-E) or converted to protein yields using a luciferase standard curve (F). AA: amino acid, AcP: acetyl-phosphate, AcK: acetyl-phosphate kinase, PEP: phosphoenol pyruvate, PyK: pyruvate kinase. Data are presented as mean±s.d. of at least three independent reactions.

3. Adapting CFPS Reaction Conditions Further Improved *C. autoethanogenum* Extract-Based CFPS The physiochemical environment of a cell-free reaction is important for cell-free functions. For example, when we varied $Mg(Glu)_2$ concentration we saw dramatic changes in protein synthesis productivity. To this point, we have mostly used physiochemical reaction conditions optimal for BL21 *E. coli* (Kwon and Jewett, 2015) (FIG. 4A). However, *C. autoethanogenum*'s proteome and metabolism significantly differs from *E. coli*'s metabolism (Kracke et al., 2016; Marcellin et al., 2016; Valgepea et al., 2018, 2017), and therefore would require physiochemical optimizations to improve *C. autoethanogenum* extract-based CFPS. We thus set out to systematically tune reaction temperature, key CFPS components involved in energy regeneration, the amino acid and co-factor concentrations, the extract concentration and oxygen availability, and the DNA template.

Figure 7:
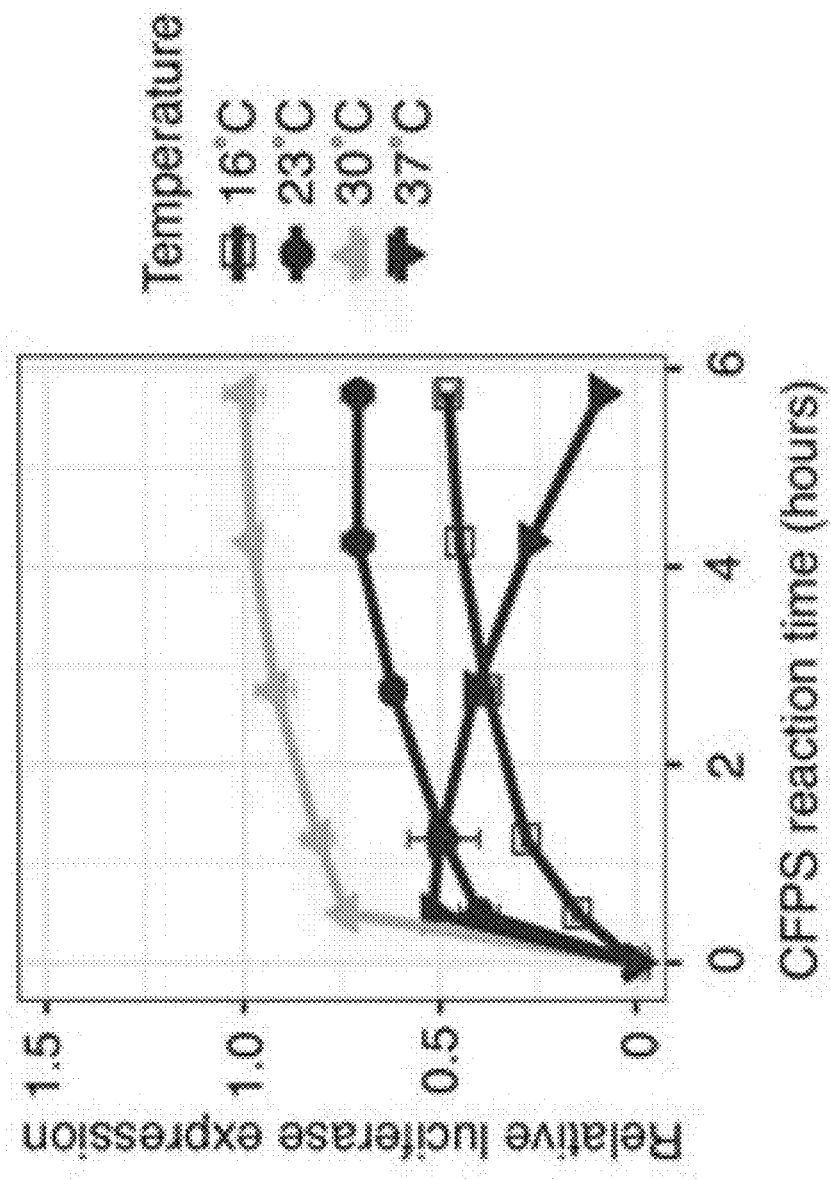
FIG. 7. Effect of temperature on CFPS with *C. autoethanogenum* extracts. Relative luciferase expression in CFPS at different reaction temperatures. *C. autoethanogenum* cell pellets were resuspended in S30 buffer, lysed by sonication at 350J, clarified by centrifugation at 12,000×g, dialyzed against S30 buffer 3 times for 45 min at 4° C., clarified again by centrifugation at 12,000×g and used for CFPS at indicated temperatures. Luciferase expression was determined by bioluminescence and plotted as relative values compared to the maximal luciferase expression at 30° C. The top line indicates optimal condition. Data are presented as mean±s.d. of three independent reactions.

First, we investigated CFPS reaction temperature. Though *E. coli*'s optimal growth temperature is 37° C., *E. coli*-based CFPS works best at 30° C. While overall activity might be slower at the lower temperature, RNase and protease activity is also reduced increasing the half-lives of recombinant mRNA transcripts and synthesized proteins thereby enhancing overall protein synthesis capabilities in cell-free systems. To test this effect in *C. autoethanogenum* extracts, we set the temperature of CFPS at 16° C., 23° C., 30° C., and 37° C. (FIG. 7). We found that 16° C. and 23° C. decreased luciferase expression to 48±2% and 71±4%, respectively. Interestingly, though, CFPS of luciferase at 30° C. and 37° C. increased similarly in the first 30 min, luciferase luminescence gradually decreased at 37° C. to 9±1% after 5.75 h. This result indicates that at 37° C. protease activity in the extract is very high and leads to luciferase degradation which cannot be compensated by its production. Hence, 30° C. is the temperature optimum for *C. autoethanogenum*-based CFPS.

Figure 8:
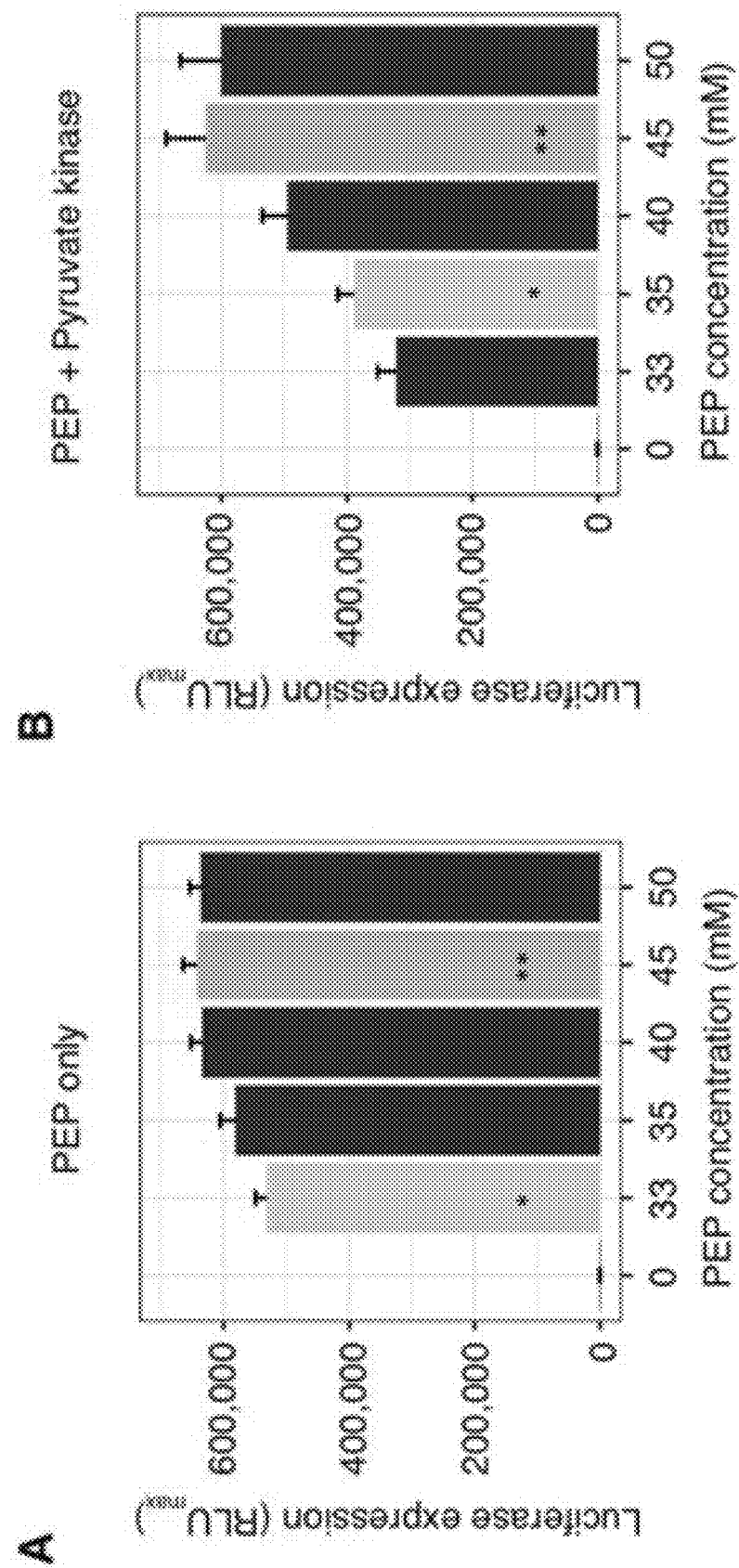
FIG. 8. Effect of phosphoenolpyruvate (PEP) on CFPS with *C. autoethanogenum* extracts. Maximal luciferase expression during CFPS (A) at different concentrations of PEP and (B) at different concentrations of PEP in the presence of pyruvate kinase (PyK). CFPS was performed with indicated PEP concentrations at 30° C. Luciferase expression was determined by bioluminescence. Bars with one * or two ** indicate previously used and newly optimized condition, respectively. Data are presented as mean±s.d. of three independent reactions.

Next, we explored energy regeneration for CFPS in in *C. autoethanogenum* extracts. Protein synthesis is a highly energy-consuming process, requiring ATP to be regenerated during transcription and translation. The primary source of ATP in the state-of-the-art *E. coli*-based PANOx-SP energy regeneration system (Jewett and Swartz, 2004) is phosphoenolpyruvate (PEP) conversion to pyruvate by pyruvate kinase (PyK). While this reaction occurs in *C. autoethanogenum*, the Wood-Ljungdahl pathway along with acetyl-phosphate kinase (AcK) reaction is more active in generating ATP for protein synthesis (Brown et al., 2014; Kracke et al., 2016; Liew et al., 2017). Due to the difference in metabolism of *E. coli* and *C. autoethanogenum*, we hypothesized that PEP might not be the most ideal energy source. To determine the best energy regeneration system for *C. autoethanogenum* extracts under aerobic conditions, we tested varying concentrations of PEP, acetyl-phosphate (AcP), and formate, a key Wood-Ljungdahl pathway metabolite. In order to mitigate potential down-regulation or oxidative damage of the substrate's-metabolizing enzymes in the extract due to aerobic extract preparation, we also tested supplementing 0.67 mg/mL of purified recombinant PyK with PEP and AcK with AcP and with formate. We found that almost no luciferase was expressed in the presence of other substrates than PEP (FIG. 4B). We further investigated varied PEP concentrations in the "PEP+PyK" energy regeneration system (FIG. 8A). Interestingly, compared to PEP alone, PEP plus pyruvate kinase (PyK) reduced CFPS productivity by about 20%. This inhibitory effect might be caused by the glycerol-containing PyK storage buffer or by side reactions and/or by-products arising from the accelerated conversion of PEP to pyruvate. In addition, we see that 45 mM PEP is optimal both with and without added PyK yielding a similar luciferase expression in both conditions (FIG. 8A; FIG. 4C). We therefore kept PEP without PyK as energy regeneration system and chose 45 mM as our new concentration moving forward.

Figure 9:
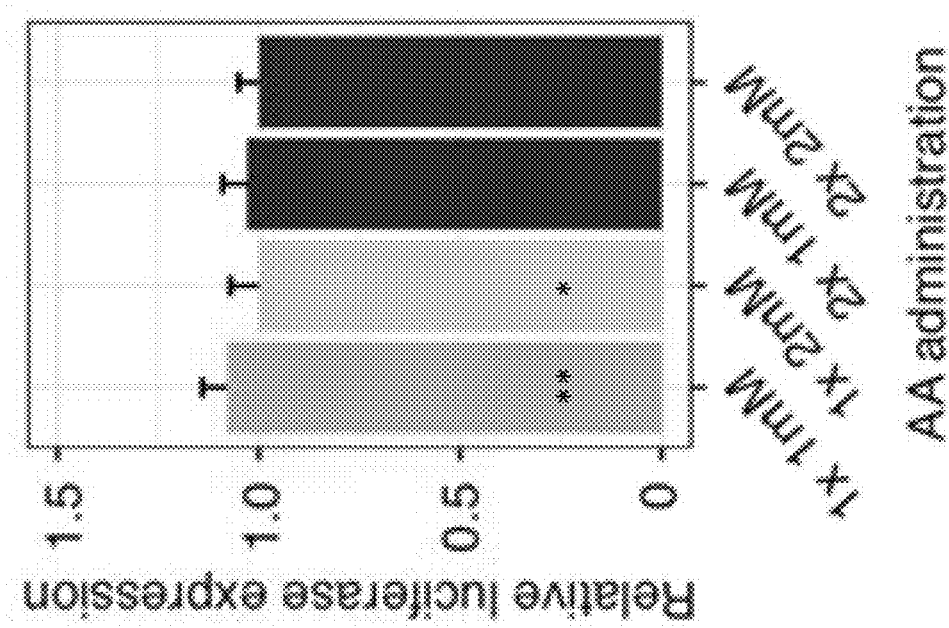
FIG. 9. Effect of a second amino acid (AA) administration after 1 hour of CFPS with *C. autoethanogenum* extracts. Relative luciferase expression at different AA administration regimes. CFPS was performed with 45 mM PEP and indicated AA concentrations, either once or a second time after 1 hr of CFPS. Luciferase expression was determined by bioluminescence and plotted as relative values compared to the previously used condition. Bars with one * or two ** indicate previously used and newly optimized condition, respectively. Data are presented as mean±s.d. of three independent reactions.

Following the optimization of the extract energy source, we evaluated the amino acid (AA) and co-factor concentrations as they are essential components in optimizing *E. coli* extract-based CFPS. In *E. coli* extracts, supplementation of 2 mM AAs ensures adequate availability for protein synthesis and background metabolism (Martin et al., 2018). To optimize the AA concentration for *C. autoethanogenum*-based CFPS, we varied the AA concentration 0-5 mM (FIG. 4D). Concentrations higher than 2 mM gradually decreased the CFPS yields, while reducing AAs to 1 mM slightly increased luciferase expression. In addition, we found that a second supplementation of AAs after one hour of CFPS had no significant effect on CFPS yields (FIG. 9). Furthermore, NAD+ and CoA both have important roles in redox balancing and metabolism and are added to CFPS reactions to ensure that the extract's metabolic activity drives ATP production for protein synthesis. In contrast to *E. coli*, *C. autoethanogenum* uses NADP(H) for many catabolic reactions and pyruvate oxidation to acetyl-CoA is independent of NAD(H) but relies on oxygen labile ferredoxin (Meinecke et al., 1989; Mock et al., 2015). In addition to these differences, aerobic *C. autoethanogenum*-based CFPS may affect the redox state and the ratio of co-factors may shift. We therefore sought to examine the impact of co-factor composition on *C. autoethanogenum* extract-based CFPS. We determined luciferase expression in CFPS in the presence or absence of NADP(H) or NAD(H) and with or without CoA (FIG. 4E). Interestingly, we found that excluding both CoA and NAD(P)(H) from the reagent mix improved luciferase expression by a third. These results together informed our selection 1 mM AA and our decision to waive the supplementation of co-factors going forward.

Figure 10:
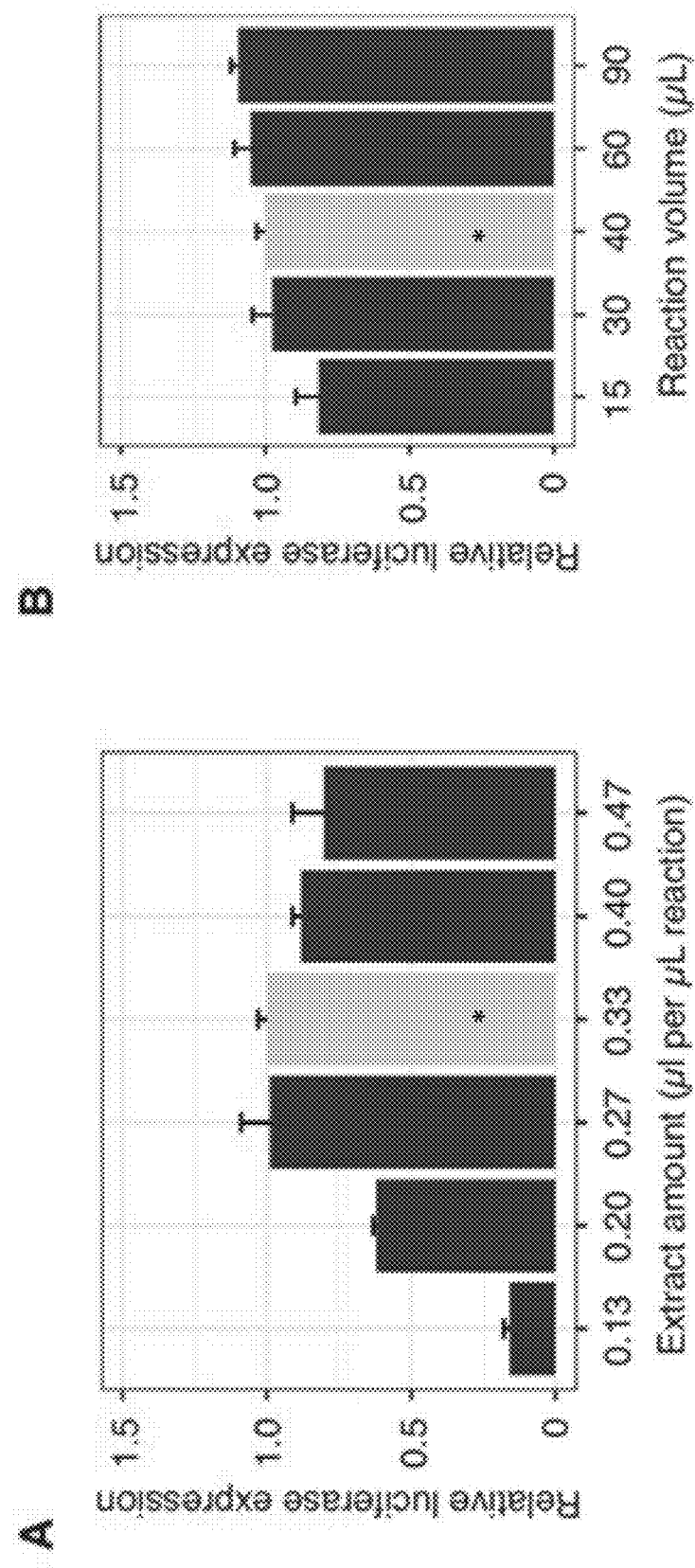
FIG. 10. Effect of extract amount and oxygen availability on CFPS with *C. autoethanogenum* extracts. (A) Relative luciferase expression in CFPS reactions containing different amounts of extract per µl CFPS reaction. CFPS reactions were set up as 40 µl batch reactions. (B) Relative luciferase expression in CFPS batch reactions set up at indicated volumes in 1.5 ml reaction tubes. Luciferase expression was determined by bioluminescence and plotted as relative values compared to the luciferase expression of the previously used condition (bar with *). Data are presented as mean±s.d. of three independent reactions.
Figure 11:
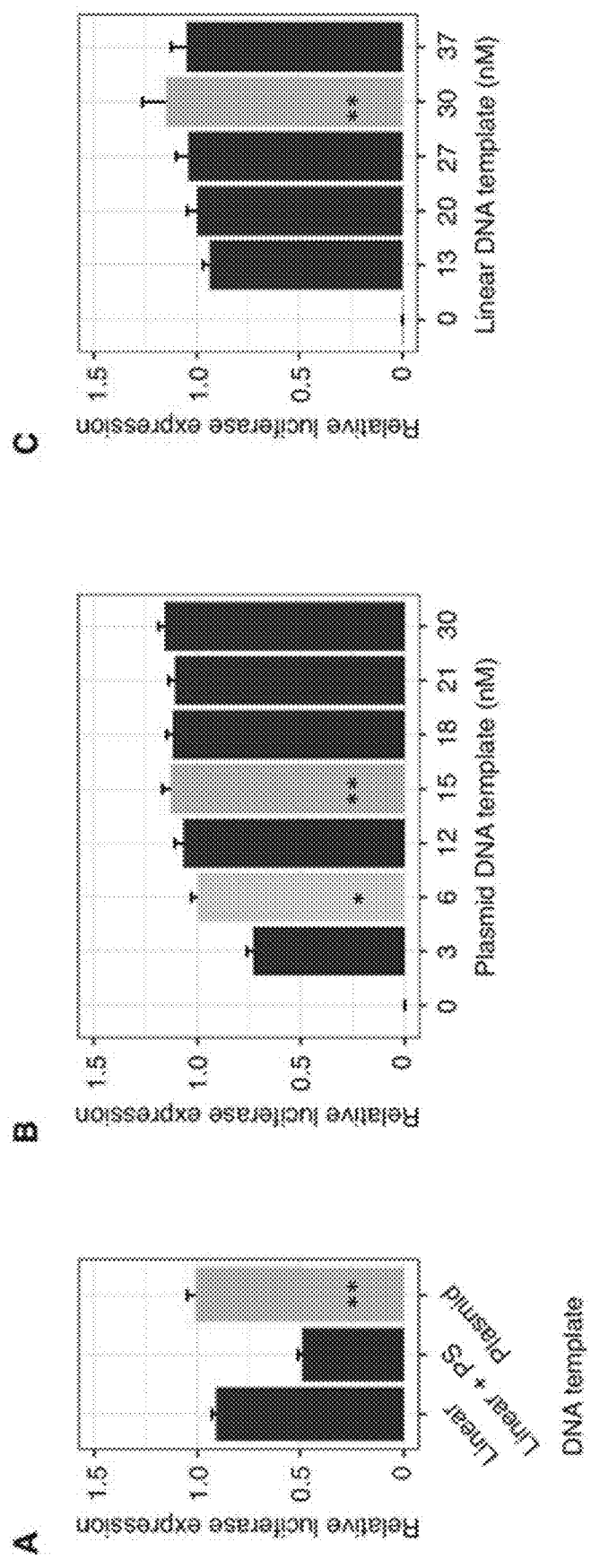
FIG. 11. Effect of DNA template type and concentration on CFPS with *C. autoethanogenum* extracts. Relative luciferase expression in CFPS reactions containing (A) different DNA template types, and different concentrations of (B) plasmid DNA, and (C) linear DNA. Plasmid DNA was midi-prepped and additionally cleaned-up by ethanol precipitation. Linear templates were prepared by PCR and cleaned using a PCR purification kit and additional ethanol precipitation. Luciferase expression was determined by bioluminescence and plotted as relative values compared to the luciferase expression of the previously used condition (bar with one *). "Linear+PS" indicates linear DNA template containing phosphorothioated 5' end modifications. Bars with two ** indicates newly optimized condition. Data are presented as mean±s.d. of three independent reactions.

Having established concentrations for the CFPS reaction buffer, we next tested the other two components of CFPS: the extract and the DNA template. Increasing the extract amount was seen to be beneficial in other extract-based CFPS systems (Li et al., 2018), so we tested varying volume amounts of *C. autoethanogenum* extracts on CFPS. However, we did not observe any improvement in protein synthesis (FIG. 10A). Clostridia are known for their high exonuclease activity (Nakotte et al., 1998). The DNA template can be added in plasmid or linear DNA forms and has a concentration-dependent effect on CFPS (Nakotte et al., 1998). We first tested whether increasing the plasmid DNA concentration from our initial 6 nM plasmid DNA would improve CFPS in *C. autoethanogenum* extracts as was helpful in other CFPS systems (Li et al., 2017). We tested 0-30 nM of plasmid DNA and found that concentrations ≥15 nM increased luciferase expression by about 10-15% (FIG. 11A). We then tested whether linear DNA templates can be used in *C. autoethanogenum* extract-based CFPS. Using linear templates made by PCR can speed-up preparation time but can be susceptible to exonucleases in cellular extracts. To test their suitability in *C. autoethanogenum* extract-based CFPS, we amplified the luciferase gene including its regulatory elements and additional ~250 bp on the 5' and 3' ends from the plasmid template via PCR using standard oligonucleotide primers and with oligonucleotide primers containing phosphorothioate (PS) bonds (Table at FIG. 6A) to increase linear template stability. Comparing CFPS from reactions containing equal molarities of DNA template, we found that linear PCR products are indeed suitable templates in *C. autoethanogenum* extract-based CFPS (FIG. 11A). Using PCR products made by standard primers decreased CFPS yields by only about 10%. Surprisingly, however, linear templates containing PS bonds at the 5' and 3' end reduced CFPS yields to 50%. We also determined the optimal concentration of PCR products made by standard primers, and found it to be 33.3 nM, yielding luciferase expression comparable with the ones gained by using plasmid templates (FIG. 11C).

After optimization of the components of the CFPS reaction, we lastly evaluated reactor operation conditions, specifically oxygen availability reaction mode (i.e., batch vs. semi-continuous). We investigated the influence of oxygen availability in *C. autoethanogenum*-based CFPS reactions by changing the reaction volume but keeping the reaction tube geometry constant in effect altering the surface area to volume ratio of the reaction. Decreasing this ratio decreases oxygen availability and lowers the effective oxygen concentration in the reaction and thereby its availability for metabolism, which is harmful for *E. coli* extract-based CFPS (Voloshin and Swartz, 2005). We tested this effect on *C. autoethanogenum*-based CFPS by performing 15-90 µL reactions in 1.5 mL reaction tubes and compared their luciferase expression to 40 µL reactions used previously.

Figure 12:
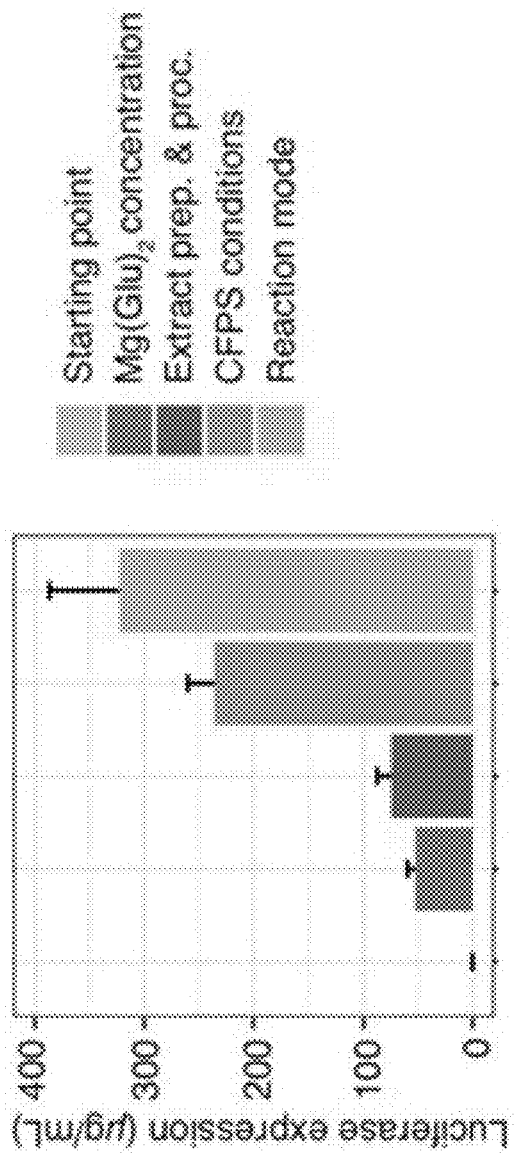
FIG. 12. Summary of the development and optimization of *C. autoethanogenum* CFPS. Shown are step-wise and cumulative improvements of luciferase expression yields in *C. autoethanogenum* CFPS. Extract prep. & proc.: extract preparation and processing; Data are presented as mean±s.d. of at least three independent reactions. Bars from left to right: 1) starting material; 2) Mg(Glu)$_2$ concentration; 3) extract prep. & proc.; 4) CFPS conditions; 5) reaction mode.

Increasing oxygen availability by running 15 µL reactions resulted in a ~20% reduction in luciferase expression. However, decreasing the oxygen availability did not show significant differences (FIG. 10B). We also tested whether running reactions in a semi-continuous fashion which offers substrate replenishment and byproduct (e.g., inorganic phosphate) removal could further increase expression yields in *C. autoethanogenum*-based CFPS. To test this question, we performed CFPS reactions in two compartments (complete reaction in one; reaction buffer without extract in the other) separated by a semi-permeable membrane (3.5 kDa cutoff). Small molecules can freely diffuse between both compartments, while metabolic enzymes and the translation machinery remain in the reaction compartment. We observed 37±14% more active luciferase in semi-continuous reactions than in batch reactions (FIG. 4F). Using all optimized conditions (CFPS reagent concentration, extract volume, DNA template concentration) (Table at FIG. 6B), we made 235.95±24.11 µg/ml of luciferase in batch mode and 322.71±63.99 µg/ml in semi-continuous reaction mode (FIG. 12).

Figure 5:
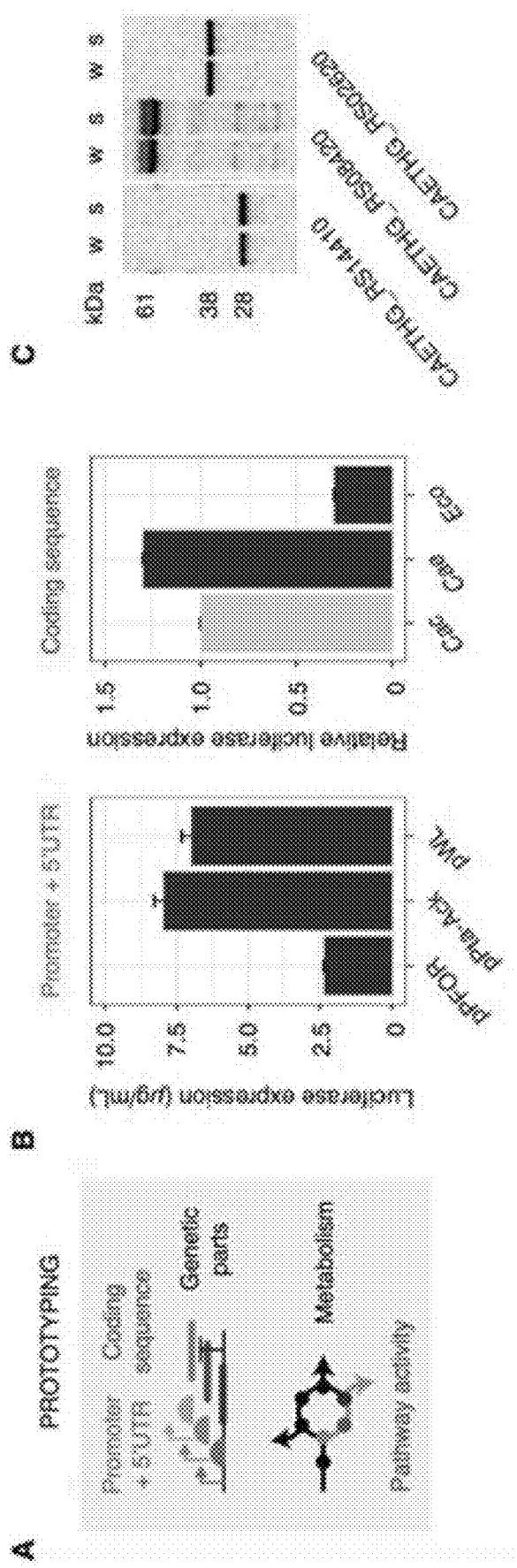
FIG. 5. *C. autoethanogenum* CFPS facilitates prototyping applications towards clostridia metabolic engineering. (A) Schematic illustration of tested prototyping applications using *C. autoethanogenum* CFPS. (B) left panel: luciferase expression from plasmid DNA templates containing native *C. autoethanogenum* promoters and a *C. autoethanogenum* adapted coding sequence. Right panel: luciferase expression from PCR product templates containing coding sequences adapted for two different *Clostridium* species, *C. acetobutylicum* (Cac) and *C. autoethanogenum* (Cae), and an aerobic bacterium, *E. coli* (Eco). CFPS was performed using the optimized conditions. Maximal luciferase expressions were determined by bioluminescence and either plotted as luciferase yields determined by using a luciferase standard curve (left panel), or as relative values compared to the for *C. autoethanogenum* adapted coding sequence (right panel). Data are presented as mean±s.d. of at least three independent reactions. (C) Autoradiography of full-length expression of recombinant native metabolic enzymes in *C. autoethanogenum* CFPS. CFPS reactions were performed using the optimized conditions and radioactive 14C-Leucine (10 µM) supplemented in addition to all 20 standard amino acids. Following CFPS, 4 µl CFPS reaction were used for SDS-PAGE. The gels were dried and exposed for 14 days on a Storage Phosphor Screen. This image was digitally compared to the stained image that included a protein standard ladder to determine the length of synthesized proteins. w and s: whole and soluble fraction, respectively. (D) Schematic illustration of the generalized carbon flux in *C. autoethanogenum* extracts during CFPS reactions. (E, F, G, H) Metabolite concentration changes during CFPS with or without 45 mM PEP as indicated in light grey or black, respectively determined by GC-MS. Data are presented as mean±s.d of four independent reactions.
Figure 13:
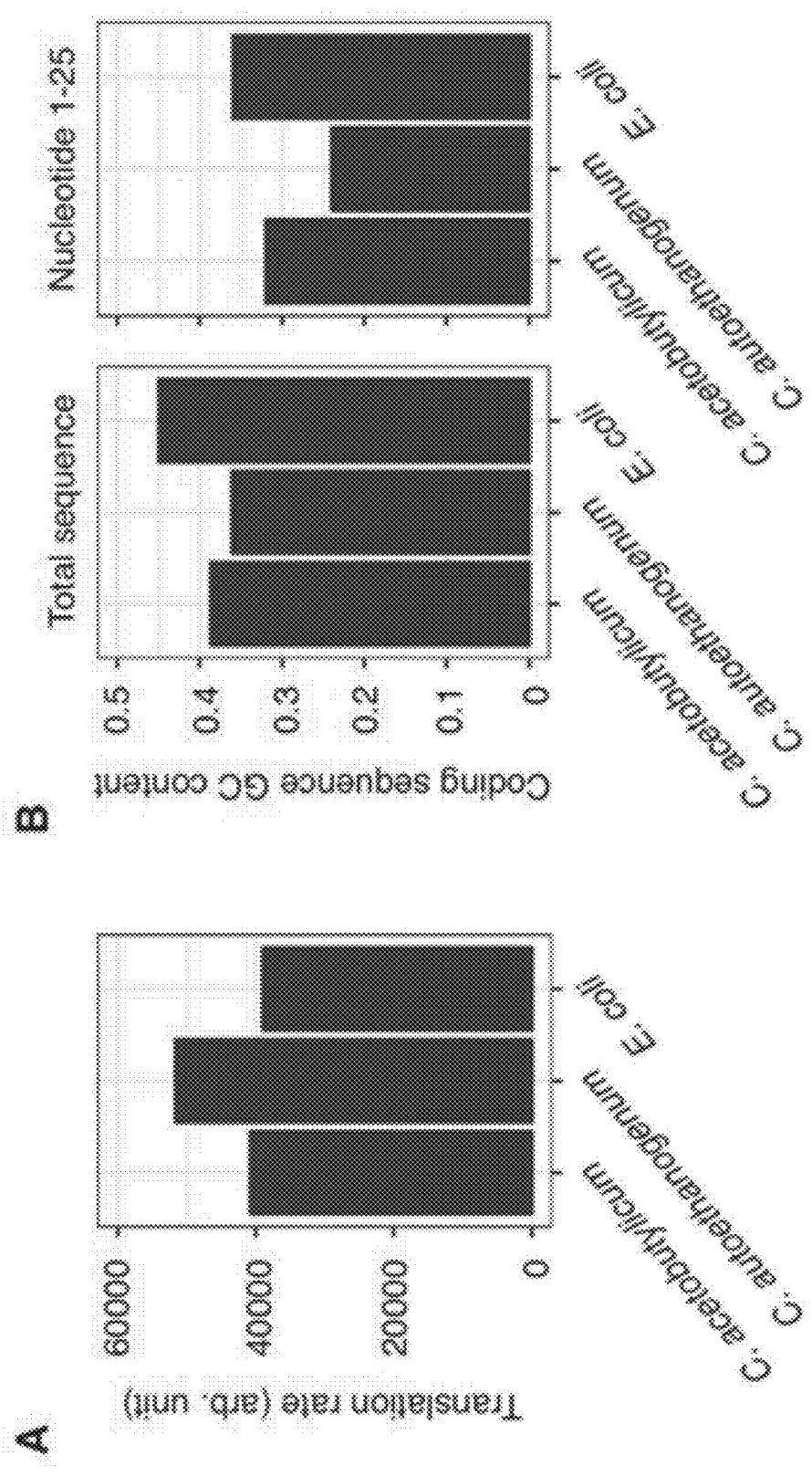
FIG. 13. Analysis of three different luciferase coding sequences. (A) Predicted translation rate determined by an RBS calculator (Salis et al., 2009). (B) GC content of luciferase coding sequences.
Figure 15:
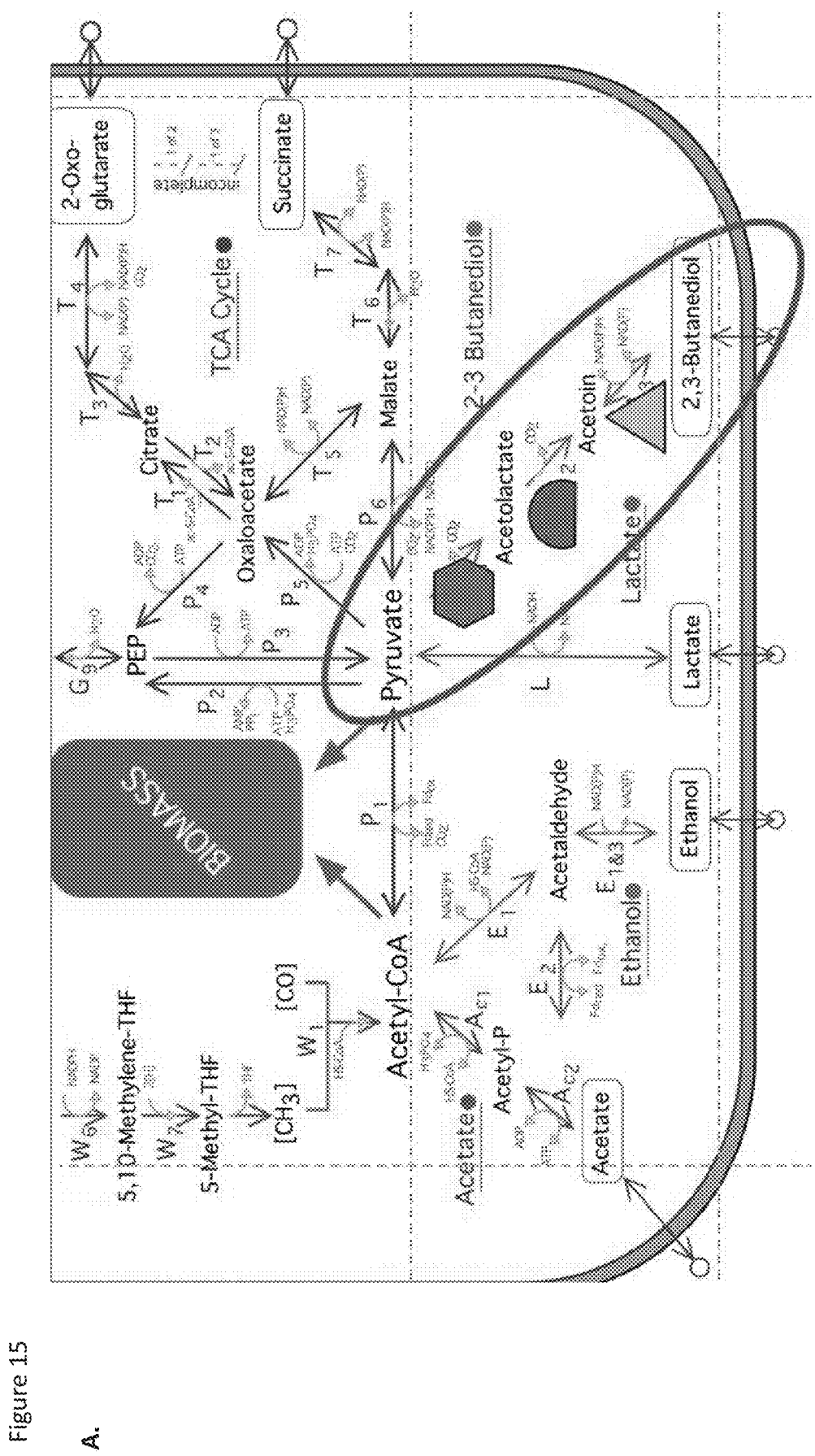
FIG. 15. Capability of prototyping metabolic pathways. (A) Schematic illustration of *C. autoethanogenum* metabolism in vivo, highlighting an example target pathway for prototyping (three-step conversion of pyruvate to 2,3 butanediol (2,3-BDO)). (B) Expression of recombinant native metabolic enzymes of the 2,3-BDO synthesis pathway (acetolactate synthase (AcLacS; hexagon), acetolactate decarboxylase (ACLacDC; half circle), secondary alcohol dehydrogenase (SecAlcDH; first triangle), 2,3-butanediol dehydrogenase (BDODH; yellow triangle)) as well as luciferase and nano-luciferase (NLuc) in *C. autoethanogenum* CFPS. CFPS reactions were performed using the optimized conditions and radioactive 14C-Leucine (10 μM) supplemented in addition to all 20 standard amino acids. Radioactively labelled protein samples were then precipitated using trichloroacetic acid and their radioactive counts measured by liquid scintillation. (C) 2,3-BDO, acetate, ethanol (EtOH) and lactate production in CFPS reactions before and after 3 h CFPS of native metabolic enzymes of the 2,3-BDO synthesis pathway. Using HPLC, metabolite concentrations were calculated from chromatogram peak areas based on standards of known concentration.

4. *C. autoethanogenum* Extract-Based CFPS Facilitates Prototyping of Genetic Parts and Metabolism for Metabolic Engineering Efforts Two of the most appealing applications for a simple, robust, and highly productive clostridia-based cell-free platform are gene expression testing and metabolic pathway prototyping as they could accelerate laborious *C. autoethanogenum* engineering efforts (FIG. 5A). In fact, metabolic engineering efforts in clostridia would benefit from a "toolbox" of well-characterized genetic parts including promoters, ribosomal binding sites, and terminators that could be assembled in combination with individual or grouped genes (Joseph et al., 2018). Thus, we evaluated the ability to test gene expression in the cell-free environment by investigating (1) codon adaptation effects, (2) the use of endogenous RNA polymerases, and (3) expression of biosynthetic enzymes. First, we compared luciferase expression using luciferase gene sequences codon-adapted for two different *Clostridium* species, *C. acetobutylicum* (Cac), *C. autoethanogenum* (Cae), and one aerobic bacterium, *E. coli* (Eco) with a significant different global GC content (*C. autoethanogenum* has a GC content of 31.1%) (Brown et al., 2014). We found that compared to luciferase expression from the *C. autoethanogenum*-adapted sequence 20% less luciferase was expressed from a *C. acetobutylicum*-adapted one and ~75% less from the sequence adapted for *E. coli* (FIG. 5B, right panel). These results correlate with the predicted translation rate determined by the Salis RBS calculator (Salis et al., 2009) and with the GC content of the gene sequences (FIG. 13). This provides a proof-of-principle that the *C. autoethanogenum*-based CFPS systems could be used for genetic part prototyping. Second, we investigated the activity of endogenous RNA polymerases by swapping the T7 promoter and the 5' UTR of our expression vector with three different clostridia native promoter regions (pPta-Ack, pPFOR, and pWL) that have been used for gene expression in the past (Liew et al., 2016), and compared their CFPS yields. We detected luciferase expression in the range of 2-7.5 µg/mL from endogenous promoters (FIG. 5B, left panel). As expected, the native promoter-based expression is ~5% of the T7 promoter-based expression in *C. autoethanogenum* extracts. Third, we wanted to test full-length synthesis of recombinant proteins other than luciferase. Thus, we expressed three recombinant enzymes with different protein lengths in *C. autoethanogenum*-based CFPS. All three enzymes were expressed in full-length and in comparable amounts (FIG. 5C). With a few optimizations, native promoters could be used in building clostridia-based genetic circuits and biosensors, and expression of recombinant proteins in full-length would be useful to build metabolic pathways in the cell-free environment to inform metabolic engineering in clostridia.

Metabolic pathway prototyping in the cell-free environment allows us to probe endogenous metabolism and biosynthetic pathways before manipulating metabolism in cells. We sought to use the *C. autoethanogenum*-based extracts to identify active metabolic pathways in vitro. While we fully expect the aerobic cell-free system presented here to be markedly different from the source anaerobic organism, we anticipate the cell-free system could be used to identify key metabolites from which novel biosynthetic routes can be developed and tested. In order to detect active metabolic routes in *C. autoethanogenum* extracts, we determined the metabolome over the course of 3-hour CFPS reactions with and without PEP and with and without DNA template for protein synthesis via GC-MS. We identified 44 metabolites: 4-hydroxybutanoic acid; phospho(enol)pyruvic acid; 3-phosphoglyceric acid; 2-phosphoglyceric acid; α-ketoglutaric acid; glucose 6-phosphate; oxalomalic acid; (S)-(−)-2-hydroxyisocaproic acid; 23-dihydroxy-isovaleric acid; alanine; hydroxypyruvic acid; indole-3-lactic acid; succinic acid; serine; malonic acid; acetoacetate; lactic acid; 4-dihydroxybutanoic acid; glycerol 1/3-phosphate; thymine; aspartic acid; lysine; glycerol 2-phosphate; glycerol; valine; 5-oxo-proline; oxalic acid; glutamic acid; phenylalanine; glycine; dithiothreitol (ox); glycolic acid; tryptophan; 3-hydroxypropanoic acid; putrescine; methionine; proline; uracil; leucine; monostearin; isoleucine; threonine; xanthine; and inosine.

The addition of DNA template for CFPS caused only minor effects on the metabolite profiles, which has been seen previously in *E. coli* cell-free systems (Karim et al., 2018), leading us to pool together the sample sets identical in PEP treatment and CFPS reaction time. We split the detected metabolites into specific anabolic and catabolic reactions based on generalized carbon flux in *C. autoethanogenum* extracts during CFPS (FIG. 5D). Excitingly, for most identified metabolites we detected concentration changes during CFPS, strongly indicating metabolic activity of their corresponding biosynthesis and degradation pathways (FIG. 5E-H). We observed large-scale effects when comparing the PEP conditions. For instance, PEP addition immediately increased the concentrations of glycolysis/gluconeogenesis intermediates 3-phosphoglyceric acid, 2-phosphoglyceric acid, and glucose 6-phosphate (FIG. 5E). Additionally, several organic acids were up-regulated, including metabolites involved in TCA cycle and carbon fixation into biomass, such as α-keto-glutaric acid, succinic acid, glycolic acid and malonic acid (FIG. 5F). Metabolites that were depleted in CFPS reactions containing PEP included the purine and pyrimidine pathway intermediates inosine, xanthine and uracil (FIG. 5G) and the amino acid methionine (FIG. 5H). In summary, we observed metabolites of glycolysis/gluconeogenesis and associated pathways, including nucleotide synthesis, incomplete TCA cycle, carbon fixation, amino acid and glycerolipid pathway. We did not observe carbon flux towards acetyl-coA and associated pathways. This observation indicates that the enzyme converting pyruvate to acetyl-CoA, pyruvate:ferredoxin oxidoreductase (PFOR), is inactive in aerobic *C. autoethanogenum* extracts as described for other clostridia (Meinecke et al., 1989). Together these results suggest that the developed *C. autoethanogenum* cell-free system could indeed be used to test libraries of genetic parts and pathways that are oxygen-independent.

Next we investigated the system's capability for prototyping metabolic pathways. To test this, we chose the conversion of pyruvate to 2,3-butanediol (2,3-BDO) as an example pathway. Using optimized *C. autoethanogenum* CFPS reaction conditions we expressed acetolactate synthetase (AcLacS), acetolactate decarboxylase (ACLacDC), secondary alcohol dehydrogenase (SecAlcDH) and 2,3-butanediol dehydrogenase (BDODH) individually or combined and determined the production of 2,3-BDO, ethanol, acetate, and lactate before and after 3 h CFPS using HPLC. We found that combined expression of all enzymes indeed increased 2,3-BDO production compared to reactions with no or individually expressed enzymes.

D. Discussion

In this work, we present a novel, robust, high-yielding CFPS system derived from the non-model and anaerobic bacterium *C. autoethanogenum* that can expand the "toolbox" of clostridia metabolic engineering and help accelerating strain engineering efforts. We identified optimal extract preparation conditions for this organism, demonstrating that *C. autoethanogenum* extracts are sensitive to lysis energies higher than 490 J, but relative consistent at lower energies. Compared to the *E. coli*-based system this lower input energy conveniently halves the extract preparation time.

Surprisingly, *C. autoethanogenum* CFPS requires unusually high magnesium concentrations. Though, including a dialysis step in the extract processing protocol decreased the initial optimum of 32 mM, 24 mM however is still a high demand. Optimizing other CFPS components specifically for *C. autoethanogenum*, we were able to produce more than 230 g/mL of luciferase within 3 hours in batch reaction mode. This yield is higher than that of most other CFPS systems derived from other model and non-model organisms such as rabbit reticulocytes (Anastasina et al., 2014), archaea (Endoh et al., 2008, 2007, 2006), yeast (Gan and Jewett, 2014; Hodgman and Jewett, 2013), insects (Ezure et al., 2010), and much higher than that of other CFPS systems derived from Gram (+) bacteria to the best of the inventors' knowledge, see e.g., *Bacillus subtilis* (Kelwick et al., 2016), *Bacillus megaterium* (Moore, Simon J.; MacDonald, James T.; Wienecke, Sarah; Ishwarbhai, Alka; Tsipa, Argyro; Aw, Rochelle; Kylilis, Nicolas; Bell, David J., McClymont, David W.; Jensen, Kirsten; Polizzi, Karen M.; Biedendieck, Rebekka; Freemont, 2018) and *Streptomyces* (Li et al., 2018, 2017). Performing semi-continuous reactions, we increased yields to more than 320 µg/mL within 4 hours. Only CFPS systems derived from CHO cell (Martin et al., 2017), *V. natriegens* (Des Soye et al., 2018), wheat germ (Harbers, 2014) and *E. coli* (Caschera and Noireaux, 2014) have been demonstrated to be more productive.

We anticipate that our optimization workflow can pave the way for development of CFPS systems for clostridia species including solventogenic or cellulolytic clostridia but also medical relevant clostridia. Further optimizing CFPS reaction conditions could help prolong the CFPS reaction duration and thereby further increase protein yields and development of an anaerobic system may mimics the cell environment of clostridia even better. Because our system exposes the extracts to oxygen, we assume that oxygen-sensitive proteins, including metabolic enzymes, get damaged and cannot be rescued by the endogenous clostridia antioxidant machinery. Alternatively, supplementing the aerobic system with antioxidant systems could rescue reversible oxidative protein damage.

We demonstrate the suitability of our system for prototyping of genetic parts. Though we only tested a few promoters and gene coding sequences, the data gained demonstrate that our *C. autoethanogenum*-based CFPS system in combination with the luciferase reporter assay is sensitive and dynamic enough to detect both transcription and translation-associated expression differences. Importantly, our system allows prototyping of native promoters that need to be recognized by the endogenous transcription machinery. This is a particularly powerful feature of our system. The most commonly used promoters for clostridia metabolic engineering originate from a few strains and are often not transferrable to non-native hosts. Being able to characterize promoter parts and to test adjustments rapidly and in high-throughput can have a huge impact on clostridia metabolic engineering. Looking forward, we expect that our system combined with a liquid handler can rapidly prototype hundreds of genetic parts.

Our developed system showed metabolic activity of native pathways. Though the oxygen exposure of the extracts probably inactivates oxygen-sensitive enzymes such as PFOR, we detected metabolic activity in several pathways associated with glycolysis. By comparing metabolite concentration changes during CFPS with and without the energy substrate PEP, we deducted the general carbon flux in the extracts. Looking forward, we anticipate that the determined active pathways and the capability of full-length recombinant enzyme expression can be used for cell-free metabolic engineering. In conclusion, the here developed *C. autoethanogenum*-based CFPS system provides an excellent platform for prototyping clostridia metabolic engineering efforts that are oxygen-independent such as transcription and translation and metabolic pathways with oxygen-resistant enzymes.

We also demonstrated the suitability of the developed system for pathway prototyping. Expression of native metabolic enzymes implicated in the conversion of pyruvate to 2,3-BDO increased 2,3-BDO production when expressing all enzymes in a one-pot CFPS reaction. Individual or combined enzyme expression also affected EtOH production while no differences were observed for lactate and acetate production. Future efforts testing varies different combinations of enzyme homologs and optimizing pathway performance by using cell-free metabolic engineering in clostridia extracts may further improve titers and pathway performance informing metabolic engineering efforts in vivo.

E. Materials & Methods

Strains and Plasmid Constructs.

*Clostridium autoethanogenum* DSM 23693 was used in this study. DSM 23693 is a derivate of type strain DSM10061 (Heijstra et al., 2016). The gene sequences and oligonucleotides used in this study are provided in FIGS. 6 and 14 and in the SEQ ID listing.

Codon-adapted luciferase genes for CFPS were synthesized by IDT, cloned into the pJL1 plasmid using Gibson assembly and confirmed by Sanger sequencing by ACGT, Inc. Kanamycin (50 µg/mL) was used to maintain pJL1-based plasmids. *C. autoethanogenum* endogenous promoters of phosphotransacetylase-actetate kinase operon (pPta-Ack; CAETHG_RS16490), pyruvate:formate oxidoreductase (pPFOR; CAETHG_RS14890) and Wood-Ljungdahl cluster (pWL; CAETHG_RS07860) were amplified from a plasmid where the respective sequences have been amplified from the genome and cloned into a pMTL82250 vector reporter plasmid (Nagaraju et al., 2016) and cloned in place of the T7 promoter region in the pJL1-LucCae construct using Gibson assembly and confirmed by Sanger sequencing by ACGT, Inc.

Cell Culture and Harvest

Fermentations with C. autoethanogenum were carried out in 10-L bioreactors with a working volume of 6 L at 37° C. and CO-containing gas (50% CO, 10% $H_2$, 20% $CO_2$, 20% $N_2$) as sole energy and carbon source at a bacterial growth rate near 1 day$^{-1}$ as described earlier (Wang et al., 2013). Prior to harvest of the cells, the pH of the culture was adjusted to pH 6 with $K_2CO_3$. Five liters of culture was collected on ice. The culture was divided between 1-L centrifuge bottles and cells pelleted at 5000×g for 10 min. The supernatant was decanted, and residual liquid removed. The pellets were resuspended in ~300 mL of 50 mM $K_2PO_4$, pH 7.5. Resuspensions were transferred to 50-mL-Falcon-tubes and cells pelleted at 5000×g for 15 min. Supernatants were discarded and the pellets immediately frozen on liquid $N_2$ and stored at –80° C.

Extract Preparation.

Cell pellets were thawed and suspended in 0.33 mL of S30 buffer (10 mM Tris($CH_3COO$) (pH 8.2), 14 mM Mg($CH_3COO$)$_2$, 10 mM K($CH_3COO$), 4 mM DTT) per gram of wet cell mass. The cell suspension was transferred as 1 mL aliquots into 1.5 mL microtubes. Using a Q125 Sonicator (Qsonica, Newtown, CT, USA) with 3.175 mm diameter probe at a 20 kHz frequency and 50% amplitude, cells were lysed for several cycles of 10 s ON/10 s OFF until final input energy was reached. Samples were kept in an ice-water bath during sonication to minimize potential heat denaturation arising from sonication. For each 1 mL cell suspension aliquot, the input energy was ~70 Joules/sonication cycle. Subsequently, lysates were centrifuged at 12,000×g at 4° C. for 10 min, supernatants collected, flash-frozen in liquid nitrogen, and stored at –80° C. until use. For run-off reactions, the supernatant of the first clarifying spin was transferred to a new tube, incubated at 37° C. for 45 min or 80 min, cleared by centrifugation at 12,000×g at 4° C. for 10 min, supernatants collected, flash-frozen in liquid nitrogen, and stored at –80° C. until use. Dialysis was performed using Slide-A-Lyzer™ Dialysis Cassettes with a 3.5 kDa cut-off (Thermo Scientific, Rockford, IL, USA). Extracts were dialyzed three times with 150 mL S30 buffer per mL extract for 45 min at 4° C., and subsequently cleared by centrifugation at 12,000×g at 4° C. for 10 min. Supernatants were collected, flash frozen in liquid nitrogen, and stored at –80° C. until use.

CFPS Reaction.

A modified PANOx-SP system was utilized for CFPS reactions. Briefly, if not stated otherwise, in a 1.5 mL microtube 40-60 µL CFPS reactions were prepared by mixing the following components: 1.2 mM ATP; 0.85 mM each of GTP, UTP, and CTP; 34 µg/mL folinic acid; 170 µg/mL of E. coli tRNA mixture; 16 µg/mL T7 RNA polymerase; 2 mM for each of the 20 standard amino acids; 0.33 mM nicotinamide adenine dinucleotide (NAD); 0.27 mM coenzyme-A (CoA); 1.5 mM spermidine; 1 mM putrescine; 4 mM sodium oxalate; 8 mM magnesium glutamate; 10 mM ammonium glutamate; 130 mM potassium glutamate; 57 mM HEPES (pH 7.2); 33 mM phosphoenolpyruvate (PEP), and 33% (v/v) of cell extract. Unless noted otherwise, synthesis of specific products was initiated by adding 6 nM of pJL1 template plasmid encoding the gene of interest to each reaction, and each CFPS reaction was incubated at 30° C. Because individual reagent concentrations were optimized throughout the study, their determined optimal values were used for all reactions from that point onward. E. coli total tRNA mixture (from strain MRE600) and PEP was purchased from Roche Applied Science (Indianapolis, IN, USA); ATP, GTP, CTP, UTP, 20 amino acids and other materials were purchased from Sigma (St. Louis, MO, USA) without further purification. T7RNAP was purified in house as described previously (Martin et al., 2018).

Quantification of Active Luciferase.

Luciferase expression in CFPS was determined using the ONE-Glo Luciferase Assay System (Promega, Madison, WI, USA), a Synergy 2 plate reader (BioTek, Winooski, VT, USA), and 96-well half area white plates (Costar 3694; Corning, Corning, NY). The assay was performed using 4 µl CFPS reaction mixed with 30 µl of luciferase assay buffer. Luminescence was detected every 3 min over a 30 min period using a BioTek Synergy 2 plate reader (Winooski, VT, USA). The maximum amount of relative light units (RLUs) was recorded for each reaction. RLUs were then converted into µg/mL amounts using a linear standard curve determined using radioactively labelled luciferase. For this, CFPS reactions were performed with radioactive $^{14}$C-Leucine (10 µM) supplemented in addition to all 20 standard amino acids. Radioactively labelled protein samples were then precipitated using trichloroacetic acid (TCA) and their radioactive counts measured by liquid scintillation using a MicroBeta2 (PerkinElmer, Waltham, MA) to quantify soluble and total luciferase yields as previously reported (Jewett et al., 2008; Jewett and Swartz, 2004).

Semi-Continuous CFPS Reaction

90 µL CFPS semi-continuous reactions were performed using 3.5 kDa MWCO 96-well plate dialysis cassettes (Thermo Scientific, Rockford, IL, USA) in 2 mL microcentrifuge tubes with 1.4 mL dialysis buffer solution. Reactions were incubated in an Eppendorf Thermomixer C at 30° C. and 600 rpm and compared to a 60 µL batch reaction performed under the same conditions.

Gas Chromatography-Mass Spectrometry (GC-MS).

Clostridia CFPS reaction samples were analyzed by GC-MS. In brief, samples stored at –80° C. prior to analysis were thawed and centrifuged at 12,000 rpm at 4° C. for 15 minutes. An aliquot of 5 µl was transferred to a vial containing 10 µl of sorbitol (1 mg/ml aqueous solution) used as internal standard and then dried under a stream of $N_2$. Dried samples were dissolved in 250 µl of silylation-grade acetonitrile followed by addition of 250 µl of N-methyl-N-(trimethylsilyl)trifluoroacetamide (MSTFA) with 1% trimethylchlorosilane (TMCS) (Thermo Scientific, Bellefonte, PA) and heated for 1 hr at 70° C. to generate trimethylsilyl derivatives. After 2 days, 1 µl aliquots were injected into an Agilent Technologies 7890A GC coupled to a 5975C inert XL MS fitted with an RTX-5MS (5% diphenyl/95% dimethyl polysiloxane) 30 m×250 m×0.25 µm film thickness capillary column with a 5 m Integra-Guard column. Gas flow was 1.0 ml per minute and the injection port was configured for splitless injection. The initial oven temperature was 50° C. with a 2-minute hold followed by a temperature ramp of 20° C. per minute to 325° C. and held for another 11.5 minutes. The MS was operated in standard electron impact (70 eV) ionization mode. The injection port, MS transfer line, MS source, and MS quad temperatures were 250° C., 300° C., 230° C., and 150° C. respectively. A large user-created database and the commercially available Wiley Registry 10th Edition combined with the NIST 14 mass spectral database were used to identify metabolites of interest. Peaks were quantified by using extracted-ion chromatograms (EIC) rather than total ion current chromatograms, utilizing a key selected ion characteristic m/z fragment, to minimize co-eluting metabolites. The EIC was scaled back to TIC using predetermined scaling factors and quantification was based on area integration and normalized to the quantity of internal standard recovered, the volume of sample processed, the derivatization volume and injection volume.

Autoradiography.

Autoradiography was used to determine the quality of synthesized metabolic enzymes synthesized in *C. autoethanogenum* CFPS. CFPS reactions were performed with radioactive $^{14}$C-Leucine (10 µM) supplemented in addition to all 20 standard amino acids. Following 3.5 hrs incubation, 4 µl CFPS reaction was loaded onto a NuPAGE 4-12% Bis-Tris Gel (Life Technologies, Carlsbad, CA, USA) following the manufacturer's instructions. The NuPAGE gels were stained with InstantBlue (Expedeon, Cambridgeshire, UK). The gels were dried and exposed for 14 days on a Storage Phosphor Screen (GE Healthcare Biosciences, Chicago, IL, USA) and imaged with a Typhoon FLA 7000 (GE Healthcare Biosciences). This image was digitally compared to the stained image that included a protein standard ladder to determine the length of synthesized proteins.

REFERENCES

Anastasina, M., Terenin, I., Butcher, S. J., Kainov, D. E., 2014. A technique to increase protein yield in a rabbit reticulocyte lysate translation system. Biotechniques 56. https://doi.org/10.2144/000114125

Brödel, A. K., Sonnabend, A., Kubick, S., 2014. Cell-free protein expression based on extracts from CHO cells. Biotechnol. Bioeng. 111, 25-36. https://doi.org/10.1002/bit.25013

Brown, S. D., Nagaraju, S., Utturkar, S., De Tissera, S., Segovia, S., Mitchell, W., Land, M. L., Dassanayake, A., Köpke, M., 2014. Comparison of single-molecule sequencing and hybrid approaches for finishing the genome of *Clostridium autoethanogenum* and analysis of CRISPR systems in industrial relevant Clostridia. Biotechnol. Biofuels 7, 40. https://doi.org/10.1186/1754-6834-7-40

Bujara, M., Schuimperli, M., Pellaux, R., Heinemann, M., Panke, S., 2011. Optimization of a blueprint for in vitro glycolysis by metabolic real-time analysis. Nat. Chem. Biol. 7, 271-277. https://doi.org/10.1038/nchembio.541

Carlson, E. D., Gan, R., Hodgman, C. E., Jewett, M. C., 2012. Cell-free protein synthesis: Applications come of age. Biotechnol. Adv. 30, 1185-1194. https://doi.org/10.1016/J.BIOTECHADV.2011.09.016

Caschera, F., Noireaux, V., 2014. Synthesis of 2.3 mg/ml of protein with an all *Escherichia coli* cell-free transcription-translation system. Biochimie 99, 162-168. https://doi.org/10.1016/J.BIOCHI.2013.11.025

Chappell, J., Jensen, K., Freemont, P. S., 2013. Validation of an entirely in vitro approach for rapid prototyping of DNA regulatory elements for synthetic biology. Nucleic Acids Res. 41, 3471-3481. https://doi.org/10.1093/nar/gkt052

Daniell, J., Nagaraju, S., Burton, F., Köpke, M., Simpson, S. D., 2015. Low-Carbon Fuel and Chemical Production by Anaerobic Gas Fermentation. Springer, Cham, pp. 293-321. https://doi.org/10.1007/10_2015_5005

Des Soye, B. J., Davidson, S. R., Weinstock, M. T., Gibson, D. G., Jewett, M. C., 2018. Establishing a High-Yielding Cell-Free Protein Synthesis Platform Derived from *Vibrio natriegens*. ACS Synth. Biol. 7, 2245-2255. https://doi.org/10.1021/acssynbio.8b00252

Dudley, Q. M., Nash, C. J., Jewett, M. C., 2019. Cell-free biosynthesis of limonene using enzyme-enriched *Escherichia coli* lysates. Synth. Biol. (Oxford, England) 4. https://doi.org/10.1093/SYNBIO/YSZ003

Endoh, T., Kanai, T., Imanaka, T., 2008. Effective approaches for the production of heterologous proteins using the *Thermococcus kodakaraensis*-based translation system. J. Biotechnol. 133, 177-182. https://doi.org/10.1016/J.JBIOTEC.2007.08.036

Endoh, T., Kanai, T., Imanaka, T., 2007. A highly productive system for cell-free protein synthesis using a lysate of the hyperthermophilic archaeon, *Thermococcus kodakaraensis*. Appl. Microbiol. Biotechnol. 74, 1153-1161. https://doi.org/10.1007/s00253-006-0753-3

Endoh, T., Kanai, T., Sato, Y. T., Liu, D. V., Yoshikawa, K., Atomi, H., Imanaka, T., 2006. Cell-free protein synthesis at high temperatures using the lysate of a hyperthermophile. J. Biotechnol. 126, 186-195. https://doi.org/10.1016/J.JBIOTEC.2006.04.010

Ezure, T., Suzuki, T., Shikata, M., Ito, M., Ando, E., 2010. A Cell-Free Protein Synthesis System from Insect Cells, in: Methods in Molecular Biology. Humana Press, pp. 31-42. https://doi.org/10.1007/978-1-60327-331-2_4

Failmezger, J., Scholz, S., Blombach, B., Siemann-Herzberg, M., 2018. Cell-Free Protein Synthesis From Fast-Growing *Vibrio natriegens*. Front. Microbiol. 9, 1146. https://doi.org/10.3389/fmicb.2018.01146

Ferrer-Miralles, N., Domingo-Espin, J., Corchero, J., Vázquez, E., Villaverde, A., 2009. Microbial factories for recombinant pharmaceuticals. Microb. Cell Fact. 8, 17. https://doi.org/10.1186/1475-2859-8-17

Feustel, L., Nakotte, S., Duirre, P., 2004. Characterization and Development of Two Reporter Gene Systems for *Clostridium acetobutylicum*. Appl. Environ. Microbiol. 70, 798-803. https://doi.org/10.1128/AEM.70.2.798-803.2004

Gan, R., Jewett, M. C., 2014. A combined cell-free transcription-translation system from *Saccharomyces cerevisiae* for rapid and robust protein synthe. Biotechnol. J. 9, 641-651. https://doi.org/10.1002/biot.201300545

Garamella, J., Marshall, R., Rustad, M., Noireaux, V., 2016. The All *E. coli* TX-TL Toolbox 2.0: A Platform for Cell-Free Synthetic Biology. ACS Synth. Biol 5, 355. https://doi.org/10.1021/acssynbio.5b00296

Ghaffar, T., Irshad, M., Anwar, Z., Aqil, T., Zulifqar, Z., Tariq, A., Kamran, M., Ehsan, N., Mehmood, S., 2014. Recent trends in lactic acid biotechnology: A brief review on production to purification. J. Radiat. Res. Appl. Sci. 7, 222-229. https://doi.org/10.1016/J.JRRAS.2014.03.002

Gootenberg, J. S., Abudayyeh, O. O., Lee, J. W., Essletzbichler, P., Dy, A. J., Joung, J., Verdine, V., Donghia, N., Daringer, N. M., Freije, C. A., Myhrvold, C., Bhattacharyya, R. P., Livny, J., Regev, A., Koonin, E. V, Hung, D. T., Sabeti, P. C., Collins, J. J., Zhang, F., 2017. Nucleic acid detection with CRISPR-Cas13a/C2c2. Science 356, 438-442. https://doi.org/10.1126/science.aam9321

Gregorio, N. E., Levine, M. Z., Oza, J. P., 2019. A User's Guide to Cell-Free Protein Synthesis. Methods Protoc. 2. https://doi.org/10.3390/mps2010024

Harbers, M., 2014. Wheat germ systems for cell-free protein expression. FEBS Lett. 588, 2762-2773. https://doi.org/10.1016/j.febslet.2014.05.061

Heijstra, B. D., Kern, E., Koepke, M., Segovia, S., Liew, F., 2016. NOVEL BACTERIA AND METHODS OF USE THEREOF.

Heijstra, B. D., Leang, C., Juminaga, A., 2017. Gas fermentation: cellular engineering possibilities and scale up. Microb. Cell Fact. 16, 60. https://doi.org/10.1186/s12934-017-0676-y Hodgman, C. E., Jewett, M. C., 2013. Optimized extract preparation methods and reaction conditions for improved yeast cell-free protein synthesis. Biotechnol. Bioeng. 110, 2643-2654. https://doi.org/10.1002/bit.24942

Hodgman, C. E., Jewett, M. C., 2012. Cell-free synthetic biology: Thinking outside the cell. Metab. Eng. 14, 261-269. https://doi.org/10.1016/J.YMBEN.2011.09.002

Jaroentomeechai, T., Stark, J. C., Natarajan, A., Glasscock, C. J., Yates, L. E., Hsu, K. J., Mrksich, M., Jewett, M. C., DeLisa, M. P., 2018. Single-pot glycoprotein biosynthesis using a cell-free transcription-translation system enriched with glycosylation machinery. Nat. Commun. 9, 2686. https://doi.org/10.1038/s41467-018-05110-x Jermutus, L., Ryabova, L. A., Plitckthun, A., 1998. Recent advances in producing and selecting functional proteins by using cell-free translation. Curr. Opin. Biotechnol. 9, 534-548. https://doi.org/10.1016/S0958-1669(98)80042-6

Jewett, M. C., Calhoun, K. A., Voloshin, A., Wuu, J. J., Swartz, J. R., 2008. An integrated cell-free metabolic platform for protein production and synthetic biology. Mol. Syst. Biol. https://doi.org/10.1038/msb.2008.57

Jewett, M. C., Swartz, J. R., 2004. Mimicking the *Escherichia coli* cytoplasmic environment activates long-lived and efficient cell-free protein synthesis. Biotechnol. Bioeng. 86, 19-26. https://doi.org/10.1002/bit.20026

Jiang, Y., Liu, J., Jiang, W., Yang, Y., Yang, S., 2015. Current status and prospects of industrial bio-production of n-butanol in China. Biotechnol. Adv. 33, 1493-1501. https://doi.org/10.1016/J.BIOTECHADV.2014.10.007

Jones, D. T., 2005. Applied Acetone-Butanol Fermentation, in: Clostridia. Wiley-VCH Verlag GmbH, Weinheim, FRG, pp. 125-168. https://doi.org/10.1002/3527600108.ch5

Joseph, R. C., Kim, N. M., Sandoval, N. R., 2018. Recent Developments of the Synthetic Biology Toolkit for *Clostridium*. Front. Microbiol. 9, 154. https://doi.org/10.3389/fmicb.2018.00154

Karig, D. K., Bessling, S., Thielen, P., Zhang, S., Wolfe, J., 2017. Preservation of protein expression systems at elevated temperatures for portable therapeutic production. J. R. Soc. Interface 14, 20161039. https://doi.org/10.1098/rsif.2016.1039

Karim, A. S., Dudley, Q. M., Juminaga, A., Yuan, Y., Crowe, S. A., Heggestad, J. T., Abdalla, T., Grubbe, W., Rasor, B., Coar, D., Torculas, M., Krein, M., Liew, F., Quattlebaum, A., Jensen, R. O., Stuart, J., Simpson, S. D., Köpke, M., Jewett, M. C., 2019. In vitro prototyping and rapid optimization of biosynthetic enzymes for cellular design. bioRxiv. https://doi.org/10.1101/685768

Karim, A. S., Heggestad, J. T., Crowe, S. A., Jewett, M. C., 2018. Controlling cell-free metabolism through physiochemical perturbations. Metab. Eng. 45, 86-94. https://doi.org/10.1016/J.YMBEN.2017.11.005

Karim, A. S., Jewett, M. C., 2016. A cell-free framework for rapid biosynthetic pathway prototyping and enzyme discovery. Metab. Eng. 36, 116-126. https://doi.org/10.1016/J.YMBEN.2016.03.002

Keasling, J. D., 2012. Synthetic biology and the development of tools for metabolic engineering. Metab. Eng. 14, 189-195. https://doi.org/10.1016/J.YMBEN.2012.01.004

Kelwick, R., Ricci, L., Mei Chee, S., Bell, D., Webb, A. J., Freemont, P. S., Freemont, P., 2017. Cell-free prototyping strategies for enhancing the sustainable production of polyhydroxyalkanoates bioplastics. bioRxiv. https://doi.org/10.1101/225144

Kelwick, R., Webb, A. J., MacDonald, J. T., Freemont, P. S., 2016. Development of a *Bacillus subtilis* cell-free transcription-translation system for prototyping regulatory elements. Metab. Eng. 38, 370-381. https://doi.org/10.1016/J.YMBEN.2016.09.008

Kobs, G., 2008. Selecting the cell-free protein expression system that meets your experimental goals. Promega Coop. Madison, WI, USA.

Kovtun, O., Mureev, S., Johnston, W., Alexandrov, K., 2010. Towards the Construction of Expressed Proteomes Using a *Leishmania tarentolae* Based Cell-Free Expression System. PLoS One 5, e14388. https://doi.org/10.1371/journal.pone.0014388

Kracke, F., Virdis, B., Bernhardt, P. V., Rabaey, K., Krömer, J. O., 2016. Redox dependent metabolic shift in *Clostridium autoethanogenum* by extracellular electron supply. Biotechnol. Biofuels 9, 249. https://doi.org/10.1186/s13068-016-0663-2

Kwon, Y.-C., Jewett, M. C., 2015. High-throughput preparation methods of crude extract for robust cell-free protein synthesis. Sci. Rep. 5, 8663. https://doi.org/10.1038/srep08663

Kwon, Y.-C., Oh, I.-S., Lee, N., Lee, K.-H., Yoon, Y. J., Lee, E. Y., Kim, B.-G., Kim, D.-M., 2013. Integrating cell-free biosyntheses of heme prosthetic group and apoenzyme for the synthesis of functional P450 monooxygenase. Biotechnol. Bioeng. 110, 1193-1200. https://doi.org/10.1002/bit.24785

Leuchtenberger, W., Huthmacher, K., Drauz, K., 2005. Biotechnological production of amino acids and derivatives: current status and prospects. Appl. Microbiol. Biotechnol. 69, 1-8. https://doi.org/10.1007/s00253-005-0155-y Li, J., Wang, H., Jewett, M. C., 2018. Expanding the palette of *Streptomyces*-based cell-free protein synthesis systems with enhanced yields. Biochem. Eng. J. 130, 29-33. https://doi.org/10.1016/J.BEJ.2017.11.013

Li, J., Wang, H., Kwon, Y.-C., Jewett, M. C., 2017. Establishing a high yielding *streptomyces*-based cell-free protein synthesis system. Biotechnol. Bioeng. 114, 1343-1353. https://doi.org/10.1002/bit.26253

Liew, F., Henstra, A. M., Köpke, M., Winzer, K., Simpson, S. D., Minton, N. P., 2017. Metabolic engineering of *Clostridium autoethanogenum* for selective alcohol production. Metab. Eng. 40, 104-114. https://doi.org/10.1016/J.YMBEN.2017.01.007

Liew, F., Martin, M. E., Tappel, R. C., Heijstra, B. D., Mihalcea, C., Köpke, M., 2016. Gas Fermentation-A Flexible Platform for Commercial Scale Production of Low-Carbon-Fuels and Chemicals from Waste and Renewable Feedstocks. Front. Microbiol.|www.frontiersin.org 7. https://doi.org/10.3389/fmicb.2016.00694

Madin, K., Sawasaki, T., Ogasawara, T., Endo, Y., 2000. A highly efficient and robust cell-free protein synthesis system prepared from wheat embryos: plants apparently contain a suicide system directed at ribosomes. Proc. Natl. Acad. Sci. U.S.A. 97, 559-64. https://doi.org/10.1073/pnas.97.2.559

Marcellin, E., Behrendorff, J. B., Nagaraju, S., DeTissera, S., Segovia, S., Palfreyman, R. W., Daniell, J., Licona-Cassani, C., Quek, L., Speight, R., Hodson, M. P., Simpson, S. D., Mitchell, W. P., Köpke, M., Nielsen, L. K., 2016. Low carbon fuels and commodity chemicals from waste gases—systematic approach to understand energy metabolism in a model acetogen. Green Chem. 18, 3020-3028. https://doi.org/10.1039/C5GC02708J Marshall, R., Maxwell, C. S., Collins, S. P., Jacobsen, T., Luo, M. L., Begemann, M. B., Gray, B. N., January, E., Singer, A., He, Y., Beisel, C. L., Noireaux, V., 2018. Rapid and Scalable Characterization of CRISPR Technologies Using an E. coli Cell-Free Transcription-Translation System. Mol. Cell 69, 146-157.e3. https://doi.org/10.1016/J.MOLCEL.2017.12.007

Martin, R. W., Des Soye, B. J., Kwon, Y.-C. C., Kay, J., Davis, R. G., Thomas, P. M., Majewska, N. I., Chen, C. X., Marcum, R. D., Weiss, M. G., Stoddart, A. E., Amiram, M., Ranji Charna, A. K., Patel, J. R., Isaacs, F. J., Kelleher, N. L., Hong, S. H., Jewett, M. C., 2018. Cell-free protein synthesis from genomically recoded bacteria enables multisite incorporation of noncanonical amino acids. Nat. Commun. 9, 1-9. https://doi.org/10.1038/s41467-018-03469-5

Martin, R. W., Majewska, N. I., Chen, C. X., Albanetti, T. E., Jimenez, R. B. C., Schmelzer, A. E., Jewett, M. C., Roy, V., 2017. Development of a CHO-Based Cell-Free Platform for Synthesis of Active Monoclonal Antibodies. ACS Synth. Biol. 6, 1370-1379. https://doi.org/10.1021/acssynbio.7b00001

Meadows, A. L., Hawkins, K. M., Tsegaye, Y., Antipov, E., Kim, Y., Raetz, L., Dahl, R. H., Tai, A., Mahatdejkul-Meadows, T., Xu, L., Zhao, L., Dasika, M. S., Murarka, A., Lenihan, J., Eng, D., Leng, J. S., Liu, C.-L., Wenger, J. W., Jiang, H., Chao, L., Westfall, P., Lai, J., Ganesan, S., Jackson, P., Mans, R., Platt, D., Reeves, C. D., Saija, P. R., Wichmann, G., Holmes, V. F., Benjamin, K., Hill, P. W., Gardner, T. S., Tsong, A. E., 2016. Rewriting yeast central carbon metabolism for industrial isoprenoid production. Nat. Publ. Gr. 537. https://doi.org/10.1038/nature19769

Meinecke, B., Bertram, J., Gottsehalk, G., 1989. Purification and characterization of the pyruvate-ferredoxin oxidoreductase from Clostridium acetobutylicum, Arch Microbiol.

Mikami, S., Kobayashi, T., Imataka, H., 2010. Cell-Free Protein Synthesis Systems with Extracts from Cultured Human Cells, in: Methods in Molecular Biology. Humana Press, pp. 43-52. https://doi.org/10.1007/978-1-60327-331-2_5

Mock, J., Zheng, Y., Mueller, A. P., Ly, S., Tran, L., Segovia, S., Nagaraju, S., Köpke, M., Dürre, P., Thauer, R. K., 2015. Energy Conservation Associated with Ethanol Formation from H2 and CO2 in Clostridium autoethanogenum Involving Electron Bifurcation. J. Bacteriol. 197, 2965-80. https://doi.org/10.1128/JB.00399-15 Moore, Simon J.; MacDonald, James T.; Wienecke, Sarah; Ishwarbhai, Alka;

Tsipa, Argyro; Aw, Rochelle; Kylilis, Nicolas; Bell, David J.; McClymont, David W.; Jensen, Kirsten; Polizzi, Karen M.; Biedendieck, Rebekka; Freemont, P. S., 2018. Rapid acquisition and model-based analysis of cell-free transcription-translation reactions from nonmodel bacteria. Proc. Natl. Acad. Sci. 115, E4340-E4349. https://doi.org/10.1073/pnas.1715806115

Morgado, G., Gerngross, D., Roberts, T. M., Panke, S., 2018. Synthetic biology for cell-free biosynthesis: Fundamentals of designing novel in vitro multi-enzyme reaction networks, in: Advances in Biochemical Engineering/Biotechnology. Springer, Cham, pp. 117-146. https://doi.org/10.1007/10_2016_13

Mureev, S., Kovtun, O., Nguyen, U. T. T., Alexandrov, K., 2009. Species-independent translational leaders facilitate cell-free expression. Nat. Biotechnol. 27, 747-752. https://doi.org/10.1038/nbt.1556

Nagaraju, S., Davies, N. K., Jeffrey, D., Walker, F., Köpke, M., Simpson, S. D., 2016. Genome editing of Clostridium autoethanogenum using CRISPR/Cas9. Biotechnol Biofuels 9, 219. https://doi.org/10.1186/s13068-016-0638-3

Nakamura, C. E., Whited, G. M., 2003. Metabolic engineering for the microbial production of 1,3-propanediol. Curr. Opin. Biotechnol. 14, 454-459. https://doi.org/10.1016/J.COPBIO.2003.08.005

Nakotte, S., Schaffer, S., Böhringer, M., Dürre, P., 1998. Electroporation of, plasmid isolation from and plasmid conservation in Clostridium acetobutylicum DSM 792. Appl. Microbiol. Biotechnol. 50, 564-567.

Nielsen, J., Fussenegger, M., Keasling, J., Lee, S. Y., Liao, J. C., Prather, K., Palsson, B., 2014. Engineering synergy in biotechnology. Nat. Chem. Biol. 10, 319-322. https://doi.org/10.1038/nchembio.1519

Nielsen, J., Keasling, J. D., 2016. Engineering Cellular Metabolism. Cell 164, 1185-1197. https://doi.org/10.1016/J.CELL.2016.02.004

Nirenberg, M. W., Matthaei, J. H., 1961. The dependence of cell-free protein synthesis in E. coli upon naturally occurring or synthetic polyribonucleotides. Proc. Natl. Acad. Sci. U.S.A. 47, 1588-602. https://doi.org/10.1073/pnas.47.10.1588

Pardee, K., Green, A. A., Ferrante, T., Cameron, D. E., DaleyKeyser, A., Yin, P., Collins, J. J., 2014. Paper-Based Synthetic Gene Networks. Cell 159, 940-954. https://doi.org/10.1016/J.CELL.2014.10.004

Pardee, K., Slomovic, S., Nguyen, P. Q., Lee, J. W., Donghia, N., Burrill, D., Ferrante, T., McSorley, F. R., Furuta, Y., Vernet, A., Lewandowski, M., Boddy, C. N., Joshi, N. S., Collins, J. J., 2016. Portable, On-Demand Biomolecular Manufacturing. Cell 167, 248-259.e12. https://doi.org/10.1016/J.CELL.2016.09.013

Pelham, H. R. B., Jackson, R. J., 1976. An Efficient mRNA-Dependent Translation System from Reticulocyte Lysates. Eur. J. Biochem. 67, 247-256. https://doi.org/10.1111/j.1432-1033.1976.tb10656.x Rodriguez, B. A., Stowers, C. C., Pham, V., Cox, B. M., 2014. Green Chemistry PERSPECTIVE The production of propionic acid, propanol and propylene via sugar fermentation: an industrial perspective on the progress, technical challenges and future outlook. https://doi.org/10.1039/c3gc42000k Salehi, A. S. M., Shakalli Tang, M. J., Smith, M. T., Hunt, J. M., Law, R. A., Wood, D. W., Bundy, B. C., 2017. Cell-Free Protein Synthesis Approach to Biosensing hTRβ-Specific Endocrine Disruptors. Anal. Chem. 89, 3395-3401. https://doi.org/10.1021/acs.analchem.6b04034

Salis, H. M., Mirsky, E. A., Voigt, C. A., 2009. Automated design of synthetic ribosome binding sites to control protein expression. Nat. Biotechnol. 27, 946-950. https://doi.org/10.1038/nbt.1568

Siegal-Gaskins, D., Tuza, Z. A., Kim, J., Noireaux, V., Murray, R. M., 2014. Gene Circuit Performance Characterization and Resource Usage in a Cell-Free "Breadboard." ACS Synth. Biol. 3, 416-425. https://doi.org/10.1021/sb400203p Silverman, A. D., Kelley-Loughnane, N., Lucks, J. B., Jewett, M. C., 2019. Deconstructing Cell-Free Extract Preparation for in Vitro Activation of Transcriptional Genetic Circuitry. ACS Synth. Biol. 8, 403-414. https://doi.org/10.1021/acssynbio.8b00430

Sullivan, C. J., Pendleton, E. D., Sasmor, H. H., Hicks, W. L., Farnum, J. B., Muto, M., Amendt, E. M., Schoborg, J. A., Martin, R. W., Clark, L. G., Anderson, M. J., Choudhury, A., Fior, R., Lo, Y.-H., Griffey, R. H., Chappell, S. A., Jewett, M. C., Mauro, V. P., Dresios, J., 2016. A cell-free expression and purification process for rapid production of protein biologics. Biotechnol. J. 11, 238-248. https://doi.org/10.1002/biot.201500214

Takahashi, Melissa K., Chappell, J., Hayes, C. A., Sun, Z. Z., Kim, J., Singhal, V., Spring, K. J., Al-Khabouri, S., Fall, C. P., Noireaux, V., Murray, R. M., Lucks, J. B., 2015. Rapidly Characterizing the Fast Dynamics of RNA Genetic Circuitry with Cell-Free Transcription-Translation (TX-TL) Systems. ACS Synth. Biol. 4, 503-515. https://doi.org/10.1021/sb400206c Takahashi, Melissa K, Hayes, C. A., Chappell, J., Sun, Z. Z., Murray, R. M., Noireaux, V., Lucks, J. B., 2015. Characterizing and prototyping genetic networks with cell-free transcription–translation reactions. METHODS. https://doi.org/10.1016/j.ymeth.2015.05.020

Takahashi, M. K., Tan, X., Dy, A. J., Braff, D., Akana, R. T., Furuta, Y., Donghia, N., Ananthakrishnan, A., Collins, J. J., 2018. A low-cost paper-based synthetic biology platform for analyzing gut microbiota and host biomarkers. Nat. Commun. 9, 3347. https://doi.org/10.1038/s41467-018-05864-4

Takai, K., Sawasaki, T., Endo, Y., 2010. Practical cell-free protein synthesis system using purified wheat embryos. Nat. Protoc. 5, 227-238. https://doi.org/10.1038/nprot.2009.207

Tarui, H., Murata, M., Tani, I., Imanishi, S., Nishikawa, S., Hara, T., 2001. Establishment and characterization of cell-free translation/glycosylation in insect cell (*Spodoptera frugiperda* 21) extract prepared with high pressure treatment. Appl. Microbiol. Biotechnol. 55, 446-453. https://doi.org/10.1007/s002530000534

Tracy, B. P., Jones, S. W., Fast, A. G., Indurthi, D. C., Papoutsakis, E. T., 2012. Clostridia: the importance of their exceptional substrate and metabolite diversity for biofuel and biorefinery applications. Curr. Opin. Biotechnol. 23, 364-381. https://doi.org/10.1016/J.COPBIO.2011.10.008

Valgepea, K., de Souza Pinto Lemgruber, R., Abdalla, T., Binos, S., Takemori, N., Takemori, A., Tanaka, Y., Tappel, R., Köpke, M., Simpson, S. D., Nielsen, L. K., Marcellin, E., 2018. H2 drives metabolic rearrangements in gas-fermenting *Clostridium autoethanogenum*. Biotechnol. Biofuels 11, 55. https://doi.org/10.1186/s13068-018-1052-9

Valgepea, K., de Souza Pinto Lemgruber, R., Meaghan, K., Palfreyman, R. W., Abdalla, T., Heijstra, B. D., Behrendorff, J. B., Tappel, R., Köpke, M., Simpson, S. D., Nielsen, L. K., Marcellin, E., 2017. Maintenance of ATP Homeostasis Triggers Metabolic Shifts in Gas-Fermenting Acetogens. Cell Syst. 4, 505-515.e5. https://doi.org/10.1016/j.cels.2017.04.008

Voloshin, A. M., Swartz, J. R., 2005. Efficient and scalable method for scaling up cell free protein synthesis in batch mode. Biotechnol. Bioeng. 91, 516-521. https://doi.org/10.1002/bit.20528

Wang, H., Li, J., Jewett, M. C., 2018. Development of a *Pseudomonas putida* cell-free protein synthesis platform for rapid screening of gene regulatory elements. Synth. Biol. 3. https://doi.org/10.1093/synbio/ysy003

Wang, S., Huang, H., Kahnt, J., Mueller, A. P., Köpke, M., Thauer, R. K., 2013. NADP-specific electron-bifurcating [FeFe]-hydrogenase in a functional complex with formate dehydrogenase in *Clostridium autoethanogenum* grown on CO. J. Bacteriol. 195, 4373-86. https://doi.org/10.1128/JB.00678-13

Wee, Y.-J., Kim, J.-N., Ryu, H.-W., 2006. Biotechnological Production of Lactic Acid and Its Recent Applications. Food Technol. Biotechnol. 44, 163-172.

Wiegand, D. J., Lee, H. H., Ostrov, N., Church, G. M., 2018. Establishing a Cell-Free *Vibrio natriegens* Expression System. ACS Synth. Biol. 7, 2475-2479. https://doi.org/10.1021/acssynbio. 8b00222

Yim, H., Haselbeck, R., Niu, W., Pujol-Baxley, C., Burgard, A., Boldt, J., Khandurina, J., Trawick, J., Osterhout, R., Stephen, R., Estadilla, J., Teisan, S., Brett schreyer, H., Andrae, S., Hoon Yang, T., Yup Lee, S., Burk, M. J., Van dien, S., 2011. Metabolic engineering of *Escherichia coli* for direct production of 1,4-butanediol. Nat. Chem. Biol. 7. https://doi.org/10.1038/nCHeMBIO.580

Yim, S. S., Johns, N. I., Park, J., Gomes, A. L. C., Mcbee, R. M., Richardson, M., Ronda, C., Chen, S. P., Garenne, D., Noireaux, V., Wang, H. H., 2019. Multiplex transcriptional characterizations across diverse and hybrid bacterial cell-free expression systems. bioRxiv. https://doi.org/10.1101/427559

Köpke, M., Held, C., Hujer, S., Liesegang, H., Wiezer, A., Wollherr, A., Ehrenreich, A., Liebl, W., Gottschalk, G. & Dürre, P. *Clostridium ljungdahlii* represents a microbial production platform based on syngas. Proceedings of the National Academy of Sciences 107, 13087-13092, (2010).

Salis, H. M., Mirsky, E. A., Voigt, C. A., 2009. Automated design of synthetic ribosome binding sites to control protein expression. Nat. Biotechnol. 27, 946-950. https://doi.org/10.1038/nbt. 1568

Tummala, S. B., Tomas, C., Harris, L. M., Papoutsakis, E. T., Welker, N. E., Rudolph, F. B. & Bennett, G. N. in Clostridia: Biotechnology and Medical Applications (ed H. Bahl and P. Dürre) (Wiley-VCH Verlag GmbH, 2001).

Papoutsakis, E. T. Engineering solventogenic clostridia. Current Opinion in Biotechnology 19, 420-429, (2008).

U.S. Pat. No. 7,041,479. Enhanced in vitro synthesis of active proteins containing disulfide bonds. Kim, D., Swartz, J.

U.S. Pat. No. 7,186,525. Methods of RNA and protein synthesis. Sakanyan, V., Snapyan, M., Ghochikyan, A., Lecocq, F.

U.S. Pat. No. 8,734,856. Cell extract for cell-free protein synthesis and process for producing the same. Endo, Y.

U.S. Pat. No. 7,235,382. Preparation containing cell extracts for cell-free protein synthesis and means for synthesizing protein using the preparation. Endo, Y., Nishikawa, S.

U.S. Pat. No. 7,273,615. Reaction solution for cell-free protein synthesis, method of preparing the same, and protein synthesis method using the same. Endo, Y., Kawasaki, T., and Sawasaki, T.

U.S. Pat. No. 7,008,651. *E. coli* extract for protein synthesis. Ambuel, Y., Oosbree, T., McCormick, M., Mierendorf, R.

U.S. Pat. No. 6,994,986. In vitro synthesis of polypeptides by optimizing amino acid metabolism. Swartz, J., Kim, D.

U.S. Pat. No. 7,312,049. Total amino acid stabilization during cell-free protein synthesis. Calhoun, K. and Swartz, J.

U.S. Pat. No. 8,298,759. Protein expression yield enhancement in cell-free protein synthesis systems by addition of antifoam agents. Voloshin, A. and Swartz, J.

U.S. Pat. No. 9,005,920. Solution for cell-free protein synthesis, kit for cell-free protein synthesis, and method of protein synthesis. Kusumegi, T. and Kawaguchi, T.

U.S. Pat. No. 10,494,600. Bacteria and methods of use thereof. Heijstra, Bjorn Daniel, et al.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A cell-free protein synthesis platform for in vitro transcription of mRNA and in vitro translation of polypeptides, the platform comprising as a component a cellular extract prepared from a cell culture of a species of Clostridia, wherein the species of Clostridia is engineered to express an upregulated gene product that is a positive effector for cell-free protein synthesis (CFPS), and wherein the positive effector for CFPS is the Clostridia homolog of *E. coli* ackA.

2. The platform of claim 1, wherein the species of Clostridia is *Clostridium autoethanogenum.*

3. The platform of claim 1, wherein the species of Clostridia is engineered to be deficient in a negative effector for cell-free protein synthesis (CFPS).

4. The platform of claim 3, wherein the negative effector for CFPS is selected from the group consisting of the Clostridia homolog of *E. coli* endA, mazF, rna, rnb, rne, gar, lon, ompT, gdhA, gshA, sdaA, sdaB, speA, WaaL, tnaA, glpK, and any combination thereof.

5. The platform of claim 1, wherein the species of Clostridia is engineered to express an additional positive effector for CFPS, wherein the additional positive effector for CFPS is selected from the group consisting of the Clostridia homolog of *E. coli* ndk, pykF, cdd, dsbC, dnaK, dnaJ, crpE, tig, groS, groL, infA, injB, fusA, efp, lepA, tujB, hslR, ffr, and any combination thereof.

6. The platform of claim 1, wherein the species of Clostridia is engineered to be deficient in a release factor 1.

7. The platform of claim 1, wherein the species of Clostridia has been engineered to express T7 RNA polymerase.

8. The platform of claim 1, wherein the cell culture is in stationary phase defined as the cell culture having an $OD_{600}$ of greater than about 3.0.

9. The platform of claim 1, wherein cellular extract is prepared from cells that are harvested from a continuous cell culture.

10. The platform of claim 1, wherein the cellular extract comprises an S12 fraction and/or S30 fraction of the cell culture.

11. The platform of claim 1 further comprising: a reaction buffer; an RNA polymerase; and a transcription template, wherein the RNA polymerase is capable of transcribing the transcription template to form a translation template and the cellular extract can sustain protein synthesis through a combined transcription/translation reaction.

12. The platform of claim 1 further comprising one or more components selected from the group consisting of amino acids, salts, a macromolecular crowding agent, cofactors, an energy source comprising phosphoenol pyruvate (PEP) at a concentration of greater than about 30 mM but less than about 100 mM, a translation template, a transcription template, a DNA dependent RNA polymerase.

13. The platform of claim 1 further comprising magnesium ($Mg^+$) at a concentration greater than about 1 mM, but less than about 60 mM.

14. The platform of claim 1 further comprising potassium ($K^+$) at a concentration greater than about 10 mM, but less than about 500 mM.

15. The platform of claim 1, wherein the platform or one or more components thereof are preserved by freeze-drying.

16. A method for in vitro transcription of mRNA and translation of mRNA to prepare a polypeptide, the method comprising transcribing the mRNA from a transcription template and translating an mRNA in the platform of claim 1.

17. A kit comprising as components: (a) a cellular extract prepared from a cell culture of a species of Clostridia; and (b) a reaction mixture for transcribing and/or translating an mRNA in the cellular extract.

18. A recombinant *Clostridium autoethanogenum* engineered to be deficient in a negative effector for cell-free protein synthesis (CFPS).

19. A method for identifying and characterizing genetic parts of Clostridia and gene expression of Clostridia used for transcription and/or translation, the method comprising:
(a) creating a test library of genetic parts or variant gene sequences of Clostridia; and
(b) testing the genetic parts of the test library and/or an alternative codon expressed in the platform of claim 1.

* * * * *

SEQUENCE LISTING

```
<160> NUMBER OF SEQ ID NOS: 30

<210> SEQ ID NO 1
<211> LENGTH: 235
<212> TYPE: PRT
<213> ORGANISM: E. coli

<400> SEQUENCE: 1

Met Tyr Arg Tyr Leu Ser Ile Ala Ala Val Val Leu Ser Ala Ala Phe
1               5                   10                  15

Ser Gly Pro Ala Leu Ala Glu Gly Ile Asn Ser Phe Ser Gln Ala Lys
                20                  25                  30

Ala Ala Ala Val Lys Val His Ala Asp Ala Pro Gly Thr Phe Tyr Cys
            35                  40                  45

Gly Cys Lys Ile Asn Trp Gln Gly Lys Lys Gly Val Val Asp Leu Gln
        50                  55                  60

Ser Cys Gly Tyr Gln Val Arg Lys Asn Glu Asn Arg Ala Ser Arg Val
65                  70                  75                  80

Glu Trp Glu His Val Val Pro Ala Trp Gln Phe Gly His Gln Arg Gln
                85                  90                  95

Cys Trp Gln Asp Gly Gly Arg Lys Asn Cys Ala Lys Asp Pro Val Tyr
            100                 105                 110

Arg Lys Met Glu Ser Asp Met His Asn Leu Gln Pro Ser Val Gly Glu
        115                 120                 125

Val Asn Gly Asp Arg Gly Asn Phe Met Tyr Ser Gln Trp Asn Gly Gly
    130                 135                 140

Glu Gly Gln Tyr Gly Gln Cys Ala Met Lys Val Asp Phe Lys Glu Lys
145                 150                 155                 160

Ala Ala Glu Pro Pro Ala Arg Ala Arg Gly Ala Ile Ala Arg Thr Tyr
                165                 170                 175

Phe Tyr Met Arg Asp Gln Tyr Asn Leu Thr Leu Ser Arg Gln Gln Thr
            180                 185                 190

Gln Leu Phe Asn Ala Trp Asn Lys Met Tyr Pro Val Thr Asp Trp Glu
        195                 200                 205

Cys Glu Arg Asp Glu Arg Ile Ala Lys Val Gln Gly Asn His Asn Pro
    210                 215                 220
```

Tyr Val Gln Arg Ala Cys Gln Ala Arg Lys Ser
225                 230                 235

<210> SEQ ID NO 2
<211> LENGTH: 784
<212> TYPE: PRT
<213> ORGANISM: E. coli

<400> SEQUENCE: 2

Met Asn Pro Glu Arg Ser Glu Arg Ile Glu Ile Pro Val Leu Pro Leu
1               5                   10                  15

Arg Asp Val Val Val Tyr Pro His Met Val Ile Pro Leu Phe Val Gly
                20                  25                  30

Arg Glu Lys Ser Ile Arg Cys Leu Glu Ala Ala Met Asp His Asp Lys
            35                  40                  45

Lys Ile Met Leu Val Ala Gln Lys Glu Ala Ser Thr Asp Glu Pro Gly
50                  55                  60

Val Asn Asp Leu Phe Thr Val Gly Thr Val Ala Ser Ile Leu Gln Met
65                  70                  75                  80

Leu Lys Leu Pro Asp Gly Thr Val Lys Val Leu Val Glu Gly Leu Gln
                85                  90                  95

Arg Ala Arg Ile Ser Ala Leu Ser Asp Asn Gly Glu His Phe Ser Ala
            100                 105                 110

Lys Ala Glu Tyr Leu Glu Ser Pro Thr Ile Asp Glu Arg Glu Gln Glu
        115                 120                 125

Val Leu Val Arg Thr Ala Ile Ser Gln Phe Glu Gly Tyr Ile Lys Leu
    130                 135                 140

Asn Lys Lys Ile Pro Pro Glu Val Leu Thr Ser Leu Asn Ser Ile Asp
145                 150                 155                 160

Asp Pro Ala Arg Leu Ala Asp Thr Ile Ala Ala His Met Pro Leu Lys
                165                 170                 175

Leu Ala Asp Lys Gln Ser Val Leu Glu Met Ser Asp Val Asn Glu Arg
            180                 185                 190

Leu Glu Tyr Leu Met Ala Met Met Glu Ser Glu Ile Asp Leu Leu Gln
        195                 200                 205

Val Glu Lys Arg Ile Arg Asn Arg Val Lys Lys Gln Met Glu Lys Ser
    210                 215                 220

Gln Arg Glu Tyr Tyr Leu Asn Glu Gln Met Lys Ala Ile Gln Lys Glu
225                 230                 235                 240

Leu Gly Glu Met Asp Asp Ala Pro Asp Glu Asn Glu Ala Leu Lys Arg
                245                 250                 255

Lys Ile Asp Ala Ala Lys Met Pro Lys Glu Ala Lys Glu Lys Ala Glu
            260                 265                 270

Ala Glu Leu Gln Lys Leu Lys Met Met Ser Pro Met Ser Ala Glu Ala
        275                 280                 285

Thr Val Val Arg Gly Tyr Ile Asp Trp Met Val Gln Val Pro Trp Asn
    290                 295                 300

Ala Arg Ser Lys Val Lys Lys Asp Leu Arg Gln Ala Gln Glu Ile Leu
305                 310                 315                 320

Asp Thr Asp His Tyr Gly Leu Glu Arg Val Lys Asp Arg Ile Leu Glu
                325                 330                 335

Tyr Leu Ala Val Gln Ser Arg Val Asn Lys Ile Lys Gly Pro Ile Leu
            340                 345                 350

Cys Leu Val Gly Pro Pro Gly Val Gly Lys Thr Ser Leu Gly Gln Ser
        355                 360                 365

```
Ile Ala Lys Ala Thr Gly Arg Lys Tyr Val Arg Met Ala Leu Gly Gly
    370                 375                 380
Val Arg Asp Glu Ala Glu Ile Arg Gly His Arg Arg Thr Tyr Ile Gly
385                 390                 395                 400
Ser Met Pro Gly Lys Leu Ile Gln Lys Met Ala Lys Val Gly Val Lys
                405                 410                 415
Asn Pro Leu Phe Leu Leu Asp Glu Ile Asp Lys Met Ser Ser Asp Met
                420                 425                 430
Arg Gly Asp Pro Ala Ser Ala Leu Leu Glu Val Leu Asp Pro Glu Gln
            435                 440                 445
Asn Val Ala Phe Ser Asp His Tyr Leu Glu Val Asp Tyr Asp Leu Ser
    450                 455                 460
Asp Val Met Phe Val Ala Thr Ser Asn Ser Met Asn Ile Pro Ala Pro
465                 470                 475                 480
Leu Leu Asp Arg Met Glu Val Ile Arg Leu Ser Gly Tyr Thr Glu Asp
                485                 490                 495
Glu Lys Leu Asn Ile Ala Lys Arg His Leu Leu Pro Lys Gln Ile Glu
                500                 505                 510
Arg Asn Ala Leu Lys Lys Gly Glu Leu Thr Val Asp Asp Ser Ala Ile
            515                 520                 525
Ile Gly Ile Ile Arg Tyr Tyr Thr Arg Glu Ala Gly Val Arg Gly Leu
    530                 535                 540
Glu Arg Glu Ile Ser Lys Leu Cys Arg Lys Ala Val Lys Gln Leu Leu
545                 550                 555                 560
Leu Asp Lys Ser Leu Lys His Ile Glu Ile Asn Gly Asp Asn Leu His
                565                 570                 575
Asp Tyr Leu Gly Val Gln Arg Phe Asp Tyr Gly Arg Ala Asp Asn Glu
                580                 585                 590
Asn Arg Val Gly Gln Val Thr Gly Leu Ala Trp Thr Glu Val Gly Gly
            595                 600                 605
Asp Leu Leu Thr Ile Glu Thr Ala Cys Val Pro Gly Lys Gly Lys Leu
    610                 615                 620
Thr Tyr Thr Gly Ser Leu Gly Glu Val Met Gln Glu Ser Ile Gln Ala
625                 630                 635                 640
Ala Leu Thr Val Val Arg Ala Arg Ala Glu Lys Leu Gly Ile Asn Pro
                645                 650                 655
Asp Phe Tyr Glu Lys Arg Asp Ile His Val His Val Pro Glu Gly Ala
                660                 665                 670
Thr Pro Lys Asp Gly Pro Ser Ala Gly Ile Ala Met Cys Thr Ala Leu
            675                 680                 685
Val Ser Cys Leu Thr Gly Asn Pro Val Arg Ala Asp Val Ala Met Thr
    690                 695                 700
Gly Glu Ile Thr Leu Arg Gly Gln Val Leu Pro Ile Gly Gly Leu Lys
705                 710                 715                 720
Glu Lys Leu Leu Ala Ala His Arg Gly Gly Ile Lys Thr Val Leu Ile
                725                 730                 735
Pro Phe Glu Asn Lys Arg Asp Leu Glu Glu Ile Pro Asp Asn Val Ile
                740                 745                 750
Ala Asp Leu Asp Ile His Pro Val Lys Arg Ile Glu Glu Val Leu Thr
            755                 760                 765
Leu Ala Leu Gln Asn Glu Pro Ser Gly Met Gln Val Val Thr Ala Lys
    770                 775                 780
```

<210> SEQ ID NO 3
<211> LENGTH: 111
<212> TYPE: PRT
<213> ORGANISM: E. coli

<400> SEQUENCE: 3

Met Val Ser Arg Tyr Val Pro Asp Met Gly Asp Leu Ile Trp Val Asp
1               5                   10                  15

Phe Asp Pro Thr Lys Gly Ser Glu Gln Ala Gly His Arg Pro Ala Val
            20                  25                  30

Val Leu Ser Pro Phe Met Tyr Asn Asn Lys Thr Gly Met Cys Leu Cys
        35                  40                  45

Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
            100                 105                 110

<210> SEQ ID NO 4
<211> LENGTH: 317
<212> TYPE: PRT
<213> ORGANISM: E. coli

<400> SEQUENCE: 4

Met Arg Ala Lys Leu Leu Gly Ile Val Leu Thr Thr Pro Ile Ala Ile
1               5                   10                  15

Ser Ser Phe Ala Ser Thr Glu Thr Leu Ser Phe Thr Pro Asp Asn Ile
            20                  25                  30

Asn Ala Asp Ile Ser Leu Gly Thr Leu Ser Gly Lys Thr Lys Glu Arg
        35                  40                  45

Val Tyr Leu Ala Glu Glu Gly Arg Lys Val Ser Gln Leu Asp Trp
    50                  55                  60

Lys Phe Asn Asn Ala Ala Ile Ile Lys Gly Ala Ile Asn Trp Asp Leu
65                  70                  75                  80

Met Pro Gln Ile Ser Ile Gly Ala Ala Gly Trp Thr Thr Leu Gly Ser
                85                  90                  95

Arg Gly Gly Asn Met Val Asp Gln Asp Trp Met Asp Ser Ser Asn Pro
            100                 105                 110

Gly Thr Trp Thr Asp Glu Ser Arg His Pro Asp Thr Gln Leu Asn Tyr
        115                 120                 125

Ala Asn Glu Phe Asp Leu Asn Ile Lys Gly Trp Leu Leu Asn Glu Pro
    130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
            180                 185                 190

Lys Gln Arg Phe Lys Met Pro Tyr Ile Gly Leu Thr Gly Ser Tyr Arg
        195                 200                 205

Tyr Glu Asp Phe Glu Leu Gly Gly Thr Phe Lys Tyr Ser Gly Trp Val
    210                 215                 220

Glu Ser Ser Asp Asn Asp Glu His Tyr Asp Pro Gly Lys Arg Ile Thr
225                 230                 235                 240

Tyr Arg Ser Lys Val Lys Asp Gln Asn Tyr Tyr Ser Val Ala Val Asn
            245                 250                 255

Ala Gly Tyr Tyr Val Thr Pro Asn Ala Lys Val Tyr Val Glu Gly Ala
            260                 265                 270

Trp Asn Arg Val Thr Asn Lys Lys Gly Asn Thr Ser Leu Tyr Asp His
            275                 280                 285

Asn Asn Asn Thr Ser Asp Tyr Ser Lys Asn Gly Ala Gly Ile Glu Asn
            290                 295                 300

Tyr Asn Phe Ile Thr Thr Ala Gly Leu Lys Tyr Thr Phe
305                 310                 315

<210> SEQ ID NO 5
<211> LENGTH: 268
<212> TYPE: PRT
<213> ORGANISM: E. coli

<400> SEQUENCE: 5

Met Lys Ala Phe Trp Arg Asn Ala Ala Leu Leu Ala Val Ser Leu Leu
1               5                   10                  15

Pro Phe Ser Ser Ala Asn Ala Leu Ala Leu Gln Ala Lys Gln Tyr Gly
            20                  25                  30

Asp Phe Asp Arg Tyr Val Leu Ala Leu Ser Trp Gln Thr Gly Phe Cys
        35                  40                  45

Gln Ser Gln His Asp Arg Asn Arg Asn Glu Arg Asp Glu Cys Arg Leu
    50                  55                  60

Gln Thr Glu Thr Thr Asn Lys Ala Asp Phe Leu Thr Val His Gly Leu
65                  70                  75                  80

Trp Pro Gly Leu Pro Lys Ser Val Ala Ala Arg Gly Val Asp Glu Arg
                85                  90                  95

Arg Trp Met Arg Phe Gly Cys Ala Thr Arg Pro Ile Pro Asn Leu Pro
            100                 105                 110

Glu Ala Arg Ala Ser Arg Met Cys Ser Ser Pro Glu Thr Gly Leu Ser
        115                 120                 125

Leu Glu Thr Ala Ala Lys Leu Ser Glu Val Met Pro Gly Ala Gly Gly
    130                 135                 140

Arg Ser Cys Leu Glu Arg Tyr Glu Tyr Ala Lys His Gly Ala Cys Phe
145                 150                 155                 160

Gly Phe Asp Pro Asp Ala Tyr Phe Gly Thr Met Val Arg Leu Asn Gln
                165                 170                 175

Glu Ile Lys Glu Ser Glu Ala Gly Lys Phe Leu Ala Asp Asn Tyr Gly
            180                 185                 190

Lys Thr Val Ser Arg Arg Asp Phe Asp Ala Ala Phe Lys Ser Trp
        195                 200                 205

Gly Lys Glu Asn Val Lys Ala Val Lys Leu Thr Cys Gln Gly Asn Pro
    210                 215                 220

Ala Tyr Leu Thr Glu Ile Gln Ile Ser Ile Lys Ala Asp Ala Ile Asn
225                 230                 235                 240

Ala Pro Leu Ser Ala Asn Ser Phe Leu Pro Gln Pro His Pro Gly Asn
                245                 250                 255

Cys Gly Lys Thr Phe Val Ile Asp Lys Ala Gly Tyr
            260                 265

<210> SEQ ID NO 6

<211> LENGTH: 644
<212> TYPE: PRT
<213> ORGANISM: E. coli

<400> SEQUENCE: 6

```
Met Phe Gln Asp Asn Pro Leu Leu Ala Gln Leu Lys Gln Gln Leu His
1               5                   10                  15

Ser Gln Thr Pro Arg Ala Glu Gly Val Val Lys Ala Thr Glu Lys Gly
            20                  25                  30

Phe Gly Phe Leu Glu Val Asp Ala Gln Lys Ser Tyr Phe Ile Pro Pro
        35                  40                  45

Pro Gln Met Lys Lys Val Met His Gly Asp Arg Ile Ile Ala Val Ile
    50                  55                  60

His Ser Glu Lys Glu Arg Glu Ser Ala Glu Pro Glu Glu Leu Val Glu
65                  70                  75                  80

Pro Phe Leu Thr Arg Phe Val Gly Lys Val Gln Gly Lys Asn Asp Arg
                85                  90                  95

Leu Ala Ile Val Pro Asp His Pro Leu Leu Lys Asp Ala Ile Pro Cys
            100                 105                 110

Arg Ala Ala Arg Gly Leu Asn His Glu Phe Lys Glu Gly Asp Trp Ala
        115                 120                 125

Val Ala Glu Met Arg Arg His Pro Leu Lys Gly Asp Arg Ser Phe Tyr
    130                 135                 140

Ala Glu Leu Thr Gln Tyr Ile Thr Phe Gly Asp Asp His Phe Val Pro
145                 150                 155                 160

Trp Trp Val Thr Leu Ala Arg His Asn Leu Glu Lys Glu Ala Pro Asp
                165                 170                 175

Gly Val Ala Thr Glu Met Leu Asp Glu Gly Leu Val Arg Glu Asp Leu
            180                 185                 190

Thr Ala Leu Asp Phe Val Thr Ile Asp Ser Ala Ser Thr Glu Asp Met
        195                 200                 205

Asp Asp Ala Leu Phe Ala Lys Ala Leu Pro Asp Asp Lys Leu Gln Leu
    210                 215                 220

Ile Val Ala Ile Ala Asp Pro Thr Ala Trp Ile Ala Glu Gly Ser Lys
225                 230                 235                 240

Leu Asp Lys Ala Ala Lys Ile Arg Ala Phe Thr Asn Tyr Leu Pro Gly
                245                 250                 255

Phe Asn Ile Pro Met Leu Pro Arg Glu Leu Ser Asp Asp Leu Cys Ser
            260                 265                 270

Leu Arg Ala Asn Glu Val Arg Pro Val Leu Ala Cys Arg Met Thr Leu
        275                 280                 285

Ser Ala Asp Gly Thr Ile Glu Asp Asn Ile Glu Phe Phe Ala Ala Thr
    290                 295                 300

Ile Glu Ser Lys Ala Lys Leu Val Tyr Asp Gln Val Ser Asp Trp Leu
305                 310                 315                 320

Glu Asn Thr Gly Asp Trp Gln Pro Glu Ser Ala Ile Ala Glu Gln
                325                 330                 335

Val Arg Leu Leu Ala Gln Ile Cys Gln Arg Arg Gly Glu Trp Arg His
            340                 345                 350

Asn His Ala Leu Val Phe Lys Asp Arg Pro Asp Tyr Arg Phe Ile Leu
        355                 360                 365

Gly Glu Lys Gly Glu Val Leu Asp Ile Val Ala Glu Pro Arg Arg Ile
    370                 375                 380

Ala Asn Arg Ile Val Glu Glu Ala Met Ile Ala Ala Asn Ile Cys Ala
```

```
            385                 390                 395                 400
    Ala Arg Val Leu Arg Asp Lys Leu Gly Phe Gly Ile Tyr Asn Val His
                        405                 410                 415

Met Gly Phe Asp Pro Ala Asn Ala Asp Ala Leu Ala Ala Leu Leu Lys
                        420                 425                 430

Thr His Gly Leu His Val Asp Ala Glu Glu Val Leu Thr Leu Asp Gly
                        435                 440                 445

Phe Cys Lys Leu Arg Arg Glu Leu Asp Ala Gln Pro Thr Gly Phe Leu
                        450                 455                 460

Asp Ser Arg Ile Arg Arg Phe Gln Ser Phe Ala Glu Ile Ser Thr Glu
    465                 470                 475                 480

Pro Gly Pro His Phe Gly Leu Gly Leu Glu Ala Tyr Ala Thr Trp Thr
                        485                 490                 495

Ser Pro Ile Arg Lys Tyr Gly Asp Met Ile Asn His Arg Leu Leu Lys
                        500                 505                 510

Ala Val Ile Lys Gly Glu Thr Ala Thr Arg Pro Gln Asp Glu Ile Thr
                        515                 520                 525

Val Gln Met Ala Glu Arg Arg Leu Asn Arg Met Ala Glu Arg Asp
                        530                 535                 540

Val Gly Asp Trp Leu Tyr Ala Arg Phe Leu Lys Asp Lys Ala Gly Thr
    545                 550                 555                 560

Asp Thr Arg Phe Ala Ala Glu Ile Val Asp Ile Ser Arg Gly Gly Met
                        565                 570                 575

Arg Val Arg Leu Val Asp Asn Gly Ala Ile Ala Phe Ile Pro Ala Pro
                        580                 585                 590

Phe Leu His Ala Val Arg Asp Glu Leu Val Cys Ser Gln Glu Asn Gly
                        595                 600                 605

Thr Val Gln Ile Lys Gly Glu Thr Val Tyr Lys Val Thr Asp Val Ile
                        610                 615                 620

Asp Val Thr Ile Ala Glu Val Arg Met Glu Thr Arg Ser Ile Ile Ala
    625                 630                 635                 640

Arg Pro Val Ala

<210> SEQ ID NO 7
<211> LENGTH: 502
<212> TYPE: PRT
<213> ORGANISM: E. coli

<400> SEQUENCE: 7

Met Thr Glu Lys Lys Tyr Ile Val Ala Leu Asp Gln Gly Thr Thr Ser
    1               5                   10                  15

Ser Arg Ala Val Val Met Asp His Asp Ala Asn Ile Ile Ser Val Ser
                        20                  25                  30

Gln Arg Glu Phe Glu Gln Ile Tyr Pro Lys Pro Gly Trp Val Glu His
                        35                  40                  45

Asp Pro Met Glu Ile Trp Ala Thr Gln Ser Ser Thr Leu Val Glu Val
                        50                  55                  60

Leu Ala Lys Ala Asp Ile Ser Ser Asp Gln Ile Ala Ala Ile Gly Ile
    65                  70                  75                  80

Thr Asn Gln Arg Glu Thr Thr Ile Val Trp Glu Lys Glu Thr Gly Lys
                        85                  90                  95

Pro Ile Tyr Asn Ala Ile Val Trp Gln Cys Arg Arg Thr Ala Glu Ile
                        100                 105                 110

Cys Glu His Leu Lys Arg Asp Gly Leu Glu Asp Tyr Ile Arg Ser Asn
```

```
                    115                 120                 125
Thr Gly Leu Val Ile Asp Pro Tyr Phe Ser Gly Thr Lys Val Lys Trp
    130                 135                 140
Ile Leu Asp His Val Glu Gly Ser Arg Glu Arg Ala Arg Arg Gly Glu
145                 150                 155                 160
Leu Leu Phe Gly Thr Val Asp Thr Trp Leu Ile Trp Lys Met Thr Gln
                165                 170                 175
Gly Arg Val His Val Thr Asp Tyr Thr Asn Ala Ser Arg Thr Met Leu
            180                 185                 190
Phe Asn Ile His Thr Leu Asp Trp Asp Asp Lys Met Leu Glu Val Leu
        195                 200                 205
Asp Ile Pro Arg Glu Met Leu Pro Glu Val Arg Arg Ser Ser Glu Val
    210                 215                 220
Tyr Gly Gln Thr Asn Ile Gly Gly Lys Gly Gly Thr Arg Ile Pro Ile
225                 230                 235                 240
Ser Gly Ile Ala Gly Asp Gln Gln Ala Ala Leu Phe Gly Gln Leu Cys
                245                 250                 255
Val Lys Glu Gly Met Ala Lys Asn Thr Tyr Gly Thr Gly Cys Phe Met
            260                 265                 270
Leu Met Asn Thr Gly Glu Lys Ala Val Lys Ser Glu Asn Gly Leu Leu
        275                 280                 285
Thr Thr Ile Ala Cys Gly Pro Thr Gly Glu Val Asn Tyr Ala Leu Glu
    290                 295                 300
Gly Ala Val Phe Met Ala Gly Ala Ser Ile Gln Trp Leu Arg Asp Glu
305                 310                 315                 320
Met Lys Leu Ile Asn Asp Ala Tyr Asp Ser Glu Tyr Phe Ala Thr Lys
                325                 330                 335
Val Gln Asn Thr Asn Gly Val Tyr Val Val Pro Ala Phe Thr Gly Leu
            340                 345                 350
Gly Ala Pro Tyr Trp Asp Pro Tyr Ala Arg Gly Ala Ile Phe Gly Leu
        355                 360                 365
Thr Arg Gly Val Asn Ala Asn His Ile Ile Arg Ala Thr Leu Glu Ser
    370                 375                 380
Ile Ala Tyr Gln Thr Arg Asp Val Leu Glu Ala Met Gln Ala Asp Ser
385                 390                 395                 400
Gly Ile Arg Leu His Ala Leu Arg Val Asp Gly Gly Ala Val Ala Asn
                405                 410                 415
Asn Phe Leu Met Gln Phe Gln Ser Asp Ile Leu Gly Thr Arg Val Glu
            420                 425                 430
Arg Pro Glu Val Arg Glu Val Thr Ala Leu Gly Ala Ala Tyr Leu Ala
        435                 440                 445
Gly Leu Ala Val Gly Phe Trp Gln Asn Leu Asp Glu Leu Gln Glu Lys
    450                 455                 460
Ala Val Ile Glu Arg Glu Phe Arg Pro Gly Ile Glu Thr Thr Glu Arg
465                 470                 475                 480
Asn Tyr Arg Tyr Ala Gly Trp Lys Lys Ala Val Lys Arg Ala Met Ala
                485                 490                 495
Trp Glu Glu His Asp Glu
            500

<210> SEQ ID NO 8
<211> LENGTH: 450
<212> TYPE: PRT
<213> ORGANISM: E. coli
```

<400> SEQUENCE: 8

```
Met Thr Lys His Tyr Asp Tyr Ile Ala Ile Gly Gly Ser Gly Gly
1               5                   10                  15

Ile Ala Ser Ile Asn Arg Ala Ala Met Tyr Gly Gln Lys Cys Ala Leu
                20                  25                  30

Ile Glu Ala Lys Glu Leu Gly Gly Thr Cys Val Asn Val Gly Cys Val
            35                  40                  45

Pro Lys Lys Val Met Trp His Ala Ala Gln Ile Arg Glu Ala Ile His
50                  55                  60

Met Tyr Gly Pro Asp Tyr Gly Phe Asp Thr Thr Ile Asn Lys Phe Asn
65                  70                  75                  80

Trp Glu Thr Leu Ile Ala Ser Arg Thr Ala Tyr Ile Asp Arg Ile His
                85                  90                  95

Thr Ser Tyr Glu Asn Val Leu Gly Lys Asn Asn Val Asp Val Ile Lys
            100                 105                 110

Gly Phe Ala Arg Phe Val Asp Ala Lys Thr Leu Glu Val Asn Gly Glu
        115                 120                 125

Thr Ile Thr Ala Asp His Ile Leu Ile Ala Thr Gly Gly Arg Pro Ser
130                 135                 140

His Pro Asp Ile Pro Gly Val Glu Tyr Gly Ile Asp Ser Asp Gly Phe
145                 150                 155                 160

Phe Ala Leu Pro Ala Leu Pro Glu Arg Val Ala Val Gly Ala Gly
                165                 170                 175

Tyr Ile Ala Val Glu Leu Ala Gly Val Ile Asn Gly Leu Gly Ala Lys
            180                 185                 190

Thr His Leu Phe Val Arg Lys His Ala Pro Leu Arg Ser Phe Asp Pro
        195                 200                 205

Met Ile Ser Glu Thr Leu Val Glu Val Met Asn Ala Glu Gly Pro Gln
210                 215                 220

Leu His Thr Asn Ala Ile Pro Lys Ala Val Val Lys Asn Thr Asp Gly
225                 230                 235                 240

Ser Leu Thr Leu Glu Leu Glu Asp Gly Arg Ser Glu Thr Val Asp Cys
                245                 250                 255

Leu Ile Trp Ala Ile Gly Arg Glu Pro Ala Asn Asp Asn Ile Asn Leu
            260                 265                 270

Glu Ala Ala Gly Val Lys Thr Asn Glu Lys Gly Tyr Ile Val Val Asp
        275                 280                 285

Lys Tyr Gln Asn Thr Asn Ile Glu Gly Ile Tyr Ala Val Gly Asp Asn
290                 295                 300

Thr Gly Ala Val Glu Leu Thr Pro Val Ala Val Ala Ala Gly Arg Arg
305                 310                 315                 320

Leu Ser Glu Arg Leu Phe Asn Asn Lys Pro Asp Glu His Leu Asp Tyr
                325                 330                 335

Ser Asn Ile Pro Thr Val Val Phe Ser His Pro Pro Ile Gly Thr Val
            340                 345                 350

Gly Leu Thr Glu Pro Gln Ala Arg Glu Gln Tyr Gly Asp Asp Gln Val
        355                 360                 365

Lys Val Tyr Lys Ser Ser Phe Thr Ala Met Tyr Thr Ala Val Thr Thr
370                 375                 380

His Arg Gln Pro Cys Arg Met Lys Leu Val Cys Val Gly Ser Glu Glu
385                 390                 395                 400

Lys Ile Val Gly Ile His Gly Ile Gly Phe Gly Met Asp Glu Met Leu
```

```
            405                 410                 415
Gln Gly Phe Ala Val Ala Leu Lys Met Gly Ala Thr Lys Lys Asp Phe
            420                 425                 430

Asp Asn Thr Val Ala Ile His Pro Thr Ala Ala Glu Glu Phe Val Thr
            435                 440                 445

Met Arg
    450

<210> SEQ ID NO 9
<211> LENGTH: 518
<212> TYPE: PRT
<213> ORGANISM: E. coli

<400> SEQUENCE: 9

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala
    50                  55                  60

Leu Leu Glu Phe Ile Thr Pro Val Asp Gly Asp Ile Glu His Met Leu
65                  70                  75                  80

Thr Phe Met Arg Asp Leu His Arg Tyr Thr Ala Arg Asn Met Gly Asp
                85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys
        115                 120                 125

Thr Leu Tyr Arg Glu Gly Leu Lys Asn Arg Tyr Gly Ala Leu Met Gln
    130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly
    210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
            260                 265                 270

Glu Tyr Ala Lys Ile Gly Ile Glu Lys Asp Gly Lys Arg Leu Gln Ile
        275                 280                 285

Asn Ser Asn Val Leu Gln Ile Glu Asn Glu Leu Tyr Ala Pro Ile Arg
    290                 295                 300

Pro Lys Arg Val Thr Arg Ser Gly Glu Ser Pro Ser Asp Ala Leu Leu
305                 310                 315                 320
```

-continued

Arg Gly Gly Ile Glu Tyr Ile Glu Val Arg Ser Leu Asp Ile Asn Pro
            325                 330                 335

Phe Ser Pro Ile Gly Val Asp Glu Gln Gln Val Arg Phe Leu Asp Leu
        340                 345                 350

Phe Met Val Trp Cys Ala Leu Ala Asp Ala Pro Glu Met Ser Ser Ser
        355                 360                 365

Glu Leu Ala Cys Thr Arg Val Asn Trp Asn Arg Val Ile Leu Glu Gly
        370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
                420                 425                 430

Cys Asp Glu Leu Val Ala Cys Phe Asp Asn Pro Asp Leu Thr Phe Ser
            435                 440                 445

Ala Arg Ile Leu Arg Ser Met Ile Asp Thr Gly Ile Gly Gly Thr Gly
        450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
                485                 490                 495

Arg Arg Gln Gln Glu Met Glu Ala Ala Asp Thr Glu Pro Phe Ala Val
                500                 505                 510

Trp Leu Glu Lys His Ala
            515

<210> SEQ ID NO 10
<211> LENGTH: 471
<212> TYPE: PRT
<213> ORGANISM: E. coli

<400> SEQUENCE: 10

Met Glu Asn Phe Lys His Leu Pro Glu Pro Phe Arg Ile Arg Val Ile
1               5                   10                  15

Glu Pro Val Lys Arg Thr Thr Arg Ala Tyr Arg Glu Gly Ala Ile Ile
                20                  25                  30

Lys Ser Gly Met Asn Pro Phe Leu Leu Asp Ser Glu Asp Val Phe Ile
            35                  40                  45

Asp Leu Leu Thr Asp Ser Gly Thr Gly Ala Val Thr Gln Ser Met Gln
        50                  55                  60

Ala Ala Met Met Arg Gly Asp Glu Ala Tyr Ser Gly Ser Arg Ser Tyr
65                  70                  75                  80

Tyr Ala Leu Ala Glu Ser Val Lys Asn Ile Phe Gly Tyr Gln Tyr Thr
                85                  90                  95

Ile Pro Thr His Gln Gly Arg Gly Ala Glu Gln Ile Tyr Ile Pro Val
            100                 105                 110

Leu Ile Lys Lys Arg Glu Gln Glu Lys Gly Leu Asp Arg Ser Lys Met
        115                 120                 125

Val Ala Phe Ser Asn Tyr Phe Phe Asp Thr Thr Gln Gly His Ser Gln
    130                 135                 140

Ile Asn Gly Cys Thr Val Arg Asn Val Tyr Ile Lys Glu Ala Phe Asp
145                 150                 155                 160

Thr Gly Val Arg Tyr Asp Phe Lys Gly Asn Phe Asp Leu Glu Gly Leu
                165                 170                 175

-continued

Glu Arg Gly Ile Glu Val Gly Pro Asn Asn Val Pro Tyr Ile Val
            180                 185                 190

Ala Thr Ile Thr Ser Asn Ser Ala Gly Gly Gln Pro Val Ser Leu Ala
            195                 200                 205

Asn Leu Lys Ala Met Tyr Ser Ile Ala Lys Tyr Asp Ile Pro Val
            210                 215                 220

Val Met Asp Ser Ala Arg Phe Ala Glu Asn Ala Tyr Phe Ile Lys Gln
225                 230                 235                 240

Arg Glu Ala Glu Tyr Lys Asp Trp Thr Ile Glu Gln Ile Thr Arg Glu
                245                 250                 255

Thr Tyr Lys Tyr Ala Asp Met Leu Ala Met Ser Ala Lys Lys Asp Ala
                260                 265                 270

Met Val Pro Met Gly Gly Leu Leu Cys Met Lys Asp Asp Ser Phe Phe
            275                 280                 285

Asp Val Tyr Thr Glu Cys Arg Thr Leu Cys Val Val Gln Glu Gly Phe
            290                 295                 300

Pro Thr Tyr Gly Gly Leu Glu Gly Gly Ala Met Glu Arg Leu Ala Val
305                 310                 315                 320

Gly Leu Tyr Asp Gly Met Asn Leu Asp Trp Leu Ala Tyr Arg Ile Ala
                325                 330                 335

Gln Val Gln Tyr Leu Val Asp Gly Leu Glu Glu Ile Gly Val Val Cys
                340                 345                 350

Gln Gln Ala Gly Gly His Ala Ala Phe Val Asp Ala Gly Lys Leu Leu
            355                 360                 365

Pro His Ile Pro Ala Asp Gln Phe Pro Ala Gln Ala Leu Ala Cys Glu
            370                 375                 380

Leu Tyr Lys Val Ala Gly Ile Arg Ala Val Glu Ile Gly Ser Phe Leu
385                 390                 395                 400

Leu Gly Arg Asp Pro Lys Thr Gly Lys Gln Leu Pro Cys Pro Ala Glu
                405                 410                 415

Leu Leu Arg Leu Thr Ile Pro Arg Ala Thr Tyr Thr Gln Thr His Met
                420                 425                 430

Asp Phe Ile Ile Glu Ala Phe Lys His Val Lys Glu Asn Ala Ala Asn
            435                 440                 445

Ile Lys Gly Leu Thr Phe Thr Tyr Glu Pro Lys Val Leu Arg His Phe
            450                 455                 460

Thr Ala Lys Leu Lys Glu Val
465                 470

<210> SEQ ID NO 11
<211> LENGTH: 1061
<212> TYPE: PRT
<213> ORGANISM: E. coli

<400> SEQUENCE: 11

Met Lys Arg Met Leu Ile Asn Ala Thr Gln Gln Glu Glu Leu Arg Val
1               5                   10                  15

Ala Leu Val Asp Gly Gln Arg Leu Tyr Asp Leu Asp Ile Glu Ser Pro
            20                  25                  30

Gly His Glu Gln Lys Lys Ala Asn Ile Tyr Lys Gly Lys Ile Thr Arg
        35                  40                  45

Ile Glu Pro Ser Leu Glu Ala Ala Phe Val Asp Tyr Gly Ala Glu Arg
    50                  55                  60

His Gly Phe Leu Pro Leu Lys Glu Ile Ala Arg Glu Tyr Phe Pro Ala

```
                65                  70                  75                  80
        Asn Tyr Ser Ala His Gly Arg Pro Asn Ile Lys Asp Val Leu Arg Glu
                        85                  90                  95

Gly Gln Glu Val Ile Val Gln Ile Asp Lys Glu Arg Gly Asn Lys
                        100                 105                 110

Gly Ala Ala Leu Thr Thr Phe Ile Ser Leu Ala Gly Ser Tyr Leu Val
                        115                 120                 125

Leu Met Pro Asn Asn Pro Arg Ala Gly Gly Ile Ser Arg Arg Ile Glu
                130                 135                 140

Gly Asp Asp Arg Thr Glu Leu Lys Glu Ala Leu Ala Ser Leu Glu Leu
        145                 150                 155                 160

Pro Glu Gly Met Gly Leu Ile Val Arg Thr Ala Gly Val Gly Lys Ser
                        165                 170                 175

Ala Glu Ala Leu Gln Trp Asp Leu Ser Phe Arg Leu Lys His Trp Glu
                        180                 185                 190

Ala Ile Lys Lys Ala Ala Glu Ser Arg Pro Ala Pro Phe Leu Ile His
                        195                 200                 205

Gln Glu Ser Asn Val Ile Val Arg Ala Phe Arg Asp Tyr Leu Arg Gln
                210                 215                 220

Asp Ile Gly Glu Ile Leu Ile Asp Asn Pro Lys Val Leu Glu Leu Ala
        225                 230                 235                 240

Arg Gln His Ile Ala Ala Leu Gly Arg Pro Asp Phe Ser Ser Lys Ile
                        245                 250                 255

Lys Leu Tyr Thr Gly Glu Ile Pro Leu Phe Ser His Tyr Gln Ile Glu
                        260                 265                 270

Ser Gln Ile Glu Ser Ala Phe Gln Arg Glu Val Arg Leu Pro Ser Gly
                        275                 280                 285

Gly Ser Ile Val Ile Asp Ser Thr Glu Ala Leu Thr Ala Ile Asp Ile
                        290                 295                 300

Asn Ser Ala Arg Ala Thr Arg Gly Gly Asp Ile Glu Glu Thr Ala Phe
        305                 310                 315                 320

Asn Thr Asn Leu Glu Ala Ala Asp Glu Ile Ala Arg Gln Leu Arg Leu
                        325                 330                 335

Arg Asp Leu Gly Gly Leu Ile Val Ile Asp Phe Ile Asp Met Thr Pro
                        340                 345                 350

Val Arg His Gln Arg Ala Val Glu Asn Arg Leu Arg Glu Ala Val Arg
                        355                 360                 365

Gln Asp Arg Ala Arg Ile Gln Ile Ser His Ile Ser Arg Phe Gly Leu
                370                 375                 380

Leu Glu Met Ser Arg Gln Arg Leu Ser Pro Ser Leu Gly Glu Ser Ser
        385                 390                 395                 400

His His Val Cys Pro Arg Cys Ser Gly Thr Gly Thr Val Arg Asp Asn
                        405                 410                 415

Glu Ser Leu Ser Leu Ser Ile Leu Arg Leu Ile Glu Glu Ala Leu
                        420                 425                 430

Lys Glu Asn Thr Gln Glu Val His Ala Ile Val Pro Val Pro Ile Ala
                        435                 440                 445

Ser Tyr Leu Leu Asn Glu Lys Arg Ser Ala Val Asn Ala Ile Glu Thr
                450                 455                 460

Arg Gln Asp Gly Val Arg Cys Val Ile Val Pro Asn Asp Gln Met Glu
        465                 470                 475                 480

Thr Pro His Tyr His Val Leu Arg Val Arg Lys Gly Glu Glu Thr Pro
                        485                 490                 495
```

```
Thr Leu Ser Tyr Met Leu Pro Lys Leu His Glu Ala Met Ala Leu
            500                 505                 510

Pro Ser Glu Glu Phe Ala Glu Arg Lys Arg Pro Glu Gln Pro Ala
        515                 520                 525

Leu Ala Thr Phe Ala Met Pro Asp Val Pro Ala Pro Thr Pro Ala
    530                 535                 540

Glu Pro Ala Ala Pro Val Val Ala Pro Ala Pro Lys Ala Ala Pro Ala
545                 550                 555                 560

Thr Pro Ala Ala Pro Ala Gln Pro Gly Leu Leu Ser Arg Phe Phe Gly
                565                 570                 575

Ala Leu Lys Ala Leu Phe Ser Gly Gly Glu Thr Lys Pro Thr Glu
            580                 585                 590

Gln Pro Ala Pro Lys Ala Glu Ala Lys Pro Glu Arg Gln Gln Asp Arg
        595                 600                 605

Arg Lys Pro Arg Gln Asn Asn Arg Arg Asp Arg Asn Glu Arg Arg Asp
    610                 615                 620

Thr Arg Ser Glu Arg Thr Glu Gly Ser Asp Asn Arg Glu Glu Asn Arg
625                 630                 635                 640

Arg Asn Arg Arg Gln Ala Gln Gln Gln Thr Ala Glu Thr Arg Glu Ser
                645                 650                 655

Arg Gln Gln Ala Glu Val Thr Glu Lys Ala Arg Thr Ala Asp Glu Gln
            660                 665                 670

Gln Ala Pro Arg Arg Glu Arg Ser Arg Arg Asn Asp Asp Lys Arg
        675                 680                 685

Gln Ala Gln Gln Glu Ala Lys Ala Leu Asn Val Glu Gln Ser Val
    690                 695                 700

Gln Glu Thr Glu Gln Glu Glu Arg Val Arg Pro Val Gln Pro Arg Arg
705                 710                 715                 720

Lys Gln Arg Gln Leu Asn Gln Lys Val Arg Tyr Glu Gln Ser Val Ala
                725                 730                 735

Glu Glu Ala Val Val Ala Pro Val Val Glu Glu Thr Val Ala Ala Glu
            740                 745                 750

Pro Ile Val Gln Glu Ala Pro Ala Pro Arg Thr Glu Leu Val Lys Val
        755                 760                 765

Pro Leu Pro Val Val Ala Gln Thr Ala Pro Glu Gln Gln Glu Glu Asn
    770                 775                 780

Asn Ala Asp Asn Arg Asp Asn Gly Gly Met Pro Arg Arg Ser Arg Arg
785                 790                 795                 800

Ser Pro Arg His Leu Arg Val Ser Gly Gln Arg Arg Arg Tyr Arg
                805                 810                 815

Asp Glu Arg Tyr Pro Thr Gln Ser Pro Met Pro Leu Thr Val Ala Cys
            820                 825                 830

Ala Ser Pro Glu Leu Ala Ser Gly Lys Val Trp Ile Arg Tyr Pro Ile
        835                 840                 845

Val Arg Pro Gln Asp Val Gln Val Glu Glu Arg Glu Gln Glu Glu
    850                 855                 860

Val His Val Gln Pro Met Val Thr Glu Val Pro Val Ala Ala Ile
865                 870                 875                 880

Glu Pro Val Val Ser Ala Pro Val Val Glu Glu Val Ala Gly Val Val
                885                 890                 895

Glu Ala Pro Val Gln Val Ala Glu Pro Gln Pro Glu Val Glu Thr
            900                 905                 910
```

```
Thr His Pro Glu Val Ile Ala Ala Val Thr Gln Pro Val
            915                 920                 925

Ile Thr Glu Ser Asp Val Ala Val Ala Gln Glu Val Ala Glu Gln Ala
930                 935                 940

Glu Pro Val Val Glu Pro Gln Glu Thr Ala Asp Ile Glu Val
945                 950                 955                 960

Val Glu Thr Ala Glu Val Val Ala Glu Pro Val Val Ala Gln
            965                 970                 975

Pro Ala Ala Pro Val Val Ala Glu Val Ala Ala Glu Val Thr Val
                980                 985                 990

Ala Ala Val Glu Pro Glu Val Thr Val Glu His Asn His Ala Thr Ala
            995                 1000                1005

Pro Met Thr Arg Ala Pro Ala Pro Glu Tyr Val Pro Glu Ala Pro
        1010                1015                1020

Arg His Ser Asp Trp Gln Arg Pro Thr Phe Ala Phe Glu Gly Lys
        1025                1030                1035

Gly Ala Ala Gly Gly His Thr Ala Thr His Ala Ser Ala Ala
        1040                1045                1050

Pro Ala Arg Pro Gln Pro Val Glu
        1055                1060

<210> SEQ ID NO 12
<211> LENGTH: 447
<212> TYPE: PRT
<213> ORGANISM: E. coli

<400> SEQUENCE: 12

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220
```

```
Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
            245                 250                 255

Arg Val Ile Thr Ala Ser Asp Ser Ser Gly Thr Val Val Asp Glu Ser
        260                 265                 270

Gly Phe Thr Lys Glu Lys Leu Ala Arg Leu Ile Glu Ile Lys Ala Ser
    275                 280                 285

Arg Asp Gly Arg Val Ala Asp Tyr Ala Lys Glu Phe Gly Leu Val Tyr
290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
            325                 330                 335

Ala Asn Gly Val Lys Ala Val Ala Glu Gly Ala Asn Met Pro Thr Thr
        340                 345                 350

Ile Glu Ala Thr Glu Leu Phe Gln Gln Ala Gly Val Leu Phe Ala Pro
    355                 360                 365

Gly Lys Ala Ala Asn Ala Gly Gly Val Ala Thr Ser Gly Leu Glu Met
370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
            405                 410                 415

Gly Gly Glu Gly Glu Gln Thr Asn Tyr Val Gln Gly Ala Asn Ile Ala
        420                 425                 430

Gly Phe Val Lys Val Ala Asp Ala Met Leu Ala Gln Gly Val Ile
    435                 440                 445

<210> SEQ ID NO 13
<211> LENGTH: 454
<212> TYPE: PRT
<213> ORGANISM: E. coli

<400> SEQUENCE: 13

Met Ile Ser Leu Phe Asp Met Phe Lys Val Gly Ile Gly Pro Ser Ser
1               5                   10                  15

Ser His Thr Val Gly Pro Met Lys Ala Gly Lys Gln Phe Val Asp Asp
            20                  25                  30

Leu Val Glu Lys Gly Leu Leu Asp Ser Val Thr Arg Val Ala Val Asp
        35                  40                  45

Val Tyr Gly Ser Leu Ser Leu Thr Gly Lys Gly His His Thr Asp Ile
    50                  55                  60

Ala Ile Ile Met Gly Leu Ala Gly Asn Glu Pro Ala Thr Val Asp Ile
65                  70                  75                  80

Asp Ser Ile Pro Gly Phe Ile Arg Asp Val Glu Glu Arg Glu Arg Leu
            85                  90                  95

Leu Leu Ala Gln Gly Arg His Glu Val Asp Phe Pro Arg Asp Asn Gly
        100                 105                 110

Met Arg Phe His Asn Gly Asn Leu Pro Leu His Glu Asn Gly Met Gln
    115                 120                 125

Ile His Ala Tyr Asn Gly Asp Glu Val Val Tyr Ser Lys Thr Tyr Tyr
130                 135                 140

Ser Ile Gly Gly Gly Phe Ile Val Asp Glu Glu His Phe Gly Gln Asp
```

```
                145                 150                 155                 160
        Ala Ala Asn Glu Val Ser Val Pro Tyr Pro Phe Lys Ser Ala Thr Glu
                            165                 170                 175

Leu Leu Ala Tyr Cys Asn Glu Thr Gly Tyr Ser Leu Ser Gly Leu Ala
                            180                 185                 190

Met Gln Asn Glu Leu Ala Leu His Ser Lys Lys Glu Ile Asp Glu Tyr
                            195                 200                 205

Phe Ala His Val Trp Gln Thr Met Gln Ala Cys Ile Asp Arg Gly Met
                    210                 215                 220

Asn Thr Glu Gly Val Leu Pro Gly Pro Leu Arg Val Pro Arg Arg Ala
        225                 230                 235                 240

Ser Ala Leu Arg Arg Met Leu Val Ser Ser Asp Lys Leu Ser Asn Asp
                            245                 250                 255

Pro Met Asn Val Ile Asp Trp Val Asn Met Phe Ala Leu Ala Val Asn
                            260                 265                 270

Glu Glu Asn Ala Ala Gly Gly Arg Val Val Thr Ala Pro Thr Asn Gly
                            275                 280                 285

Ala Cys Gly Ile Val Pro Ala Val Leu Ala Tyr Tyr Asp His Phe Ile
                    290                 295                 300

Glu Ser Val Ser Pro Asp Ile Tyr Thr Arg Tyr Phe Met Ala Ala Gly
        305                 310                 315                 320

Ala Ile Gly Ala Leu Tyr Lys Met Asn Ala Ser Ile Ser Gly Ala Glu
                            325                 330                 335

Val Gly Cys Gln Gly Glu Val Gly Val Ala Cys Ser Met Ala Ala Ala
                            340                 345                 350

Gly Leu Ala Glu Leu Leu Gly Gly Ser Pro Glu Gln Val Cys Val Ala
                            355                 360                 365

Ala Glu Ile Gly Met Glu His Asn Leu Gly Leu Thr Cys Asp Pro Val
                    370                 375                 380

Ala Gly Gln Val Gln Val Pro Cys Ile Glu Arg Asn Ala Ile Ala Ser
        385                 390                 395                 400

Val Lys Ala Ile Asn Ala Ala Arg Met Ala Leu Arg Arg Thr Ser Ala
                            405                 410                 415

Pro Arg Val Ser Leu Asp Lys Val Ile Glu Thr Met Tyr Glu Thr Gly
                            420                 425                 430

Lys Asp Met Asn Ala Lys Tyr Arg Glu Thr Ser Arg Gly Gly Leu Ala
                            435                 440                 445

Ile Lys Val Gln Cys Asp
                    450

<210> SEQ ID NO 14
<211> LENGTH: 455
<212> TYPE: PRT
<213> ORGANISM: E. coli

<400> SEQUENCE: 14

Met Ile Ser Val Phe Asp Ile Phe Lys Ile Gly Ile Gly Pro Ser Ser
        1               5                   10                  15

Ser His Thr Val Gly Pro Met Lys Ala Gly Lys Gln Phe Thr Asp Asp
                        20                  25                  30

Leu Ile Ala Arg Asn Leu Leu Lys Asp Val Thr Arg Val Val Val Asp
                    35                  40                  45

Val Tyr Gly Ser Leu Ser Leu Thr Gly Lys Gly His His Thr Asp Ile
            50                  55                  60
```

```
Ala Ile Ile Met Gly Leu Ala Gly Asn Leu Pro Asp Thr Val Asp Ile
 65                  70                  75                  80

Asp Ser Ile Pro Ser Phe Ile Gln Asp Val Asn Thr His Gly Arg Leu
                 85                  90                  95

Met Leu Ala Asn Gly Gln His Glu Val Glu Phe Pro Val Asp Gln Cys
            100                 105                 110

Met Asn Phe His Ala Asp Asn Leu Ser Leu His Glu Asn Gly Met Arg
        115                 120                 125

Ile Thr Ala Leu Ala Gly Asp Lys Val Val Tyr Ser Gln Thr Tyr Tyr
    130                 135                 140

Ser Ile Gly Gly Gly Phe Ile Val Asp Glu Glu His Phe Gly Gln Gln
145                 150                 155                 160

Asp Ser Ala Pro Val Glu Val Pro Tyr Pro Tyr Ser Ser Ala Ala Asp
                165                 170                 175

Leu Gln Lys His Cys Gln Glu Thr Gly Leu Ser Leu Ser Gly Leu Met
            180                 185                 190

Met Lys Asn Glu Leu Ala Leu His Ser Lys Glu Glu Leu Glu Gln His
        195                 200                 205

Leu Ala Asn Val Trp Glu Val Met Arg Gly Gly Ile Glu Arg Gly Ile
    210                 215                 220

Ser Thr Glu Gly Val Leu Pro Gly Lys Leu Arg Val Pro Arg Arg Ala
225                 230                 235                 240

Ala Ala Leu Arg Arg Met Leu Val Ser Gln Asp Lys Thr Thr Thr Asp
                245                 250                 255

Pro Met Ala Val Val Asp Trp Ile Asn Met Phe Ala Leu Ala Val Asn
            260                 265                 270

Glu Glu Asn Ala Ala Gly Gly Arg Val Val Thr Ala Pro Thr Asn Gly
        275                 280                 285

Ala Cys Gly Ile Ile Pro Ala Val Leu Ala Tyr Tyr Asp Lys Phe Ile
    290                 295                 300

Arg Glu Val Asn Ala Asn Ser Leu Ala Arg Tyr Leu Leu Val Ala Ser
305                 310                 315                 320

Ala Ile Gly Ser Leu Tyr Lys Met Asn Ala Ser Ile Ser Gly Ala Glu
                325                 330                 335

Val Gly Cys Gln Gly Glu Val Gly Val Ala Cys Ser Met Ala Ala Ala
            340                 345                 350

Gly Leu Ala Glu Leu Leu Gly Ala Ser Pro Ala Gln Val Cys Ile Ala
        355                 360                 365

Ala Glu Ile Ala Met Glu His Asn Leu Gly Leu Thr Cys Asp Pro Val
    370                 375                 380

Ala Gly Gln Val Gln Val Pro Cys Ile Glu Arg Asn Ala Ile Ala Ala
385                 390                 395                 400

Val Lys Ala Val Asn Ala Ala Arg Met Ala Leu Arg Arg Thr Ser Glu
                405                 410                 415

Pro Arg Val Cys Leu Asp Lys Val Ile Glu Thr Met Tyr Glu Thr Gly
            420                 425                 430

Lys Asp Met Asn Ala Lys Tyr Arg Glu Thr Ser Arg Gly Gly Leu Ala
        435                 440                 445

Met Lys Ile Val Ala Cys Asp
    450                 455

<210> SEQ ID NO 15
<211> LENGTH: 658
<212> TYPE: PRT
```

<213> ORGANISM: E. coli

<400> SEQUENCE: 15

Met Ser Asp Asp Met Ser Met Gly Leu Pro Ser Ser Ala Gly Glu His
1               5                   10                  15

Gly Val Leu Arg Ser Met Gln Glu Val Ala Met Ser Ser Gln Glu Ala
            20                  25                  30

Ser Lys Met Leu Arg Thr Tyr Asn Ile Ala Trp Trp Gly Asn Asn Tyr
        35                  40                  45

Tyr Asp Val Asn Glu Leu Gly His Ile Ser Val Cys Pro Asp Pro Asp
50                  55                  60

Val Pro Glu Ala Arg Val Asp Leu Ala Gln Leu Val Lys Thr Arg Glu
65                  70                  75                  80

Ala Gln Gly Gln Arg Leu Pro Ala Leu Phe Cys Phe Pro Gln Ile Leu
                85                  90                  95

Gln His Arg Leu Arg Ser Ile Asn Ala Ala Phe Lys Arg Ala Arg Glu
            100                 105                 110

Ser Tyr Gly Tyr Asn Gly Asp Tyr Phe Leu Val Tyr Pro Ile Lys Val
        115                 120                 125

Asn Gln His Arg Arg Val Ile Glu Ser Leu Ile His Ser Gly Glu Pro
130                 135                 140

Leu Gly Leu Glu Ala Gly Ser Lys Ala Glu Leu Met Ala Val Leu Ala
145                 150                 155                 160

His Ala Gly Met Thr Arg Ser Val Ile Val Cys Asn Gly Tyr Lys Asp
                165                 170                 175

Arg Glu Tyr Ile Arg Leu Ala Leu Ile Gly Glu Lys Met Gly His Lys
            180                 185                 190

Val Tyr Leu Val Ile Glu Lys Met Ser Glu Ile Ala Ile Val Leu Asp
        195                 200                 205

Glu Ala Glu Arg Leu Asn Val Val Pro Arg Leu Gly Val Arg Ala Arg
210                 215                 220

Leu Ala Ser Gln Gly Ser Gly Lys Trp Gln Ser Ser Gly Gly Glu Lys
225                 230                 235                 240

Ser Lys Phe Gly Leu Ala Ala Thr Gln Val Leu Gln Leu Val Glu Thr
                245                 250                 255

Leu Arg Glu Ala Gly Arg Leu Asp Ser Leu Gln Leu Leu His Phe His
            260                 265                 270

Leu Gly Ser Gln Met Ala Asn Ile Arg Asp Ile Ala Thr Gly Val Arg
        275                 280                 285

Glu Ser Ala Arg Phe Tyr Val Glu Leu His Lys Leu Gly Val Asn Ile
290                 295                 300

Gln Cys Phe Asp Val Gly Gly Gly Leu Gly Val Asp Tyr Glu Gly Thr
305                 310                 315                 320

Arg Ser Gln Ser Asp Cys Ser Val Asn Tyr Gly Leu Asn Glu Tyr Ala
                325                 330                 335

Asn Asn Ile Ile Trp Ala Ile Gly Asp Ala Cys Glu Glu Asn Gly Leu
            340                 345                 350

Pro His Pro Thr Val Ile Thr Glu Ser Gly Arg Ala Val Thr Ala His
        355                 360                 365

His Thr Val Leu Val Ser Asn Ile Ile Gly Val Glu Arg Asn Glu Tyr
370                 375                 380

Thr Val Pro Thr Ala Pro Ala Glu Asp Ala Pro Arg Ala Leu Gln Ser
385                 390                 395                 400

```
Met Trp Glu Thr Trp Gln Glu Met His Glu Pro Gly Thr Arg Arg Ser
                405                 410                 415

Leu Arg Glu Trp Leu His Asp Ser Gln Met Asp Leu His Asp Ile His
            420                 425                 430

Ile Gly Tyr Ser Ser Gly Ile Phe Ser Leu Gln Glu Arg Ala Trp Ala
        435                 440                 445

Glu Gln Leu Tyr Leu Ser Met Cys His Glu Val Gln Lys Gln Leu Asp
    450                 455                 460

Pro Gln Asn Arg Ala His Arg Pro Ile Ile Asp Glu Leu Gln Glu Arg
465                 470                 475                 480

Met Ala Asp Lys Met Tyr Val Asn Phe Ser Leu Phe Gln Ser Met Pro
                485                 490                 495

Asp Ala Trp Gly Ile Asp Gln Leu Phe Pro Val Leu Pro Leu Glu Gly
            500                 505                 510

Leu Asp Gln Val Pro Glu Arg Arg Ala Val Leu Leu Asp Ile Thr Cys
        515                 520                 525

Asp Ser Asp Gly Ala Ile Asp His Tyr Ile Asp Gly Asp Gly Ile Ala
    530                 535                 540

Thr Thr Met Pro Met Pro Glu Tyr Asp Pro Glu Asn Pro Pro Met Leu
545                 550                 555                 560

Gly Phe Phe Met Val Gly Ala Tyr Gln Glu Ile Leu Gly Asn Met His
                565                 570                 575

Asn Leu Phe Gly Asp Thr Glu Ala Val Asp Val Phe Val Phe Pro Asp
            580                 585                 590

Gly Ser Val Glu Val Glu Leu Ser Asp Glu Gly Asp Thr Val Ala Asp
        595                 600                 605

Met Leu Gln Tyr Val Gln Leu Asp Pro Lys Thr Leu Leu Thr Gln Phe
    610                 615                 620

Arg Asp Gln Val Lys Lys Thr Asp Leu Asp Ala Glu Leu Gln Gln Gln
625                 630                 635                 640

Phe Leu Glu Glu Phe Glu Ala Gly Leu Tyr Gly Tyr Thr Tyr Leu Glu
                645                 650                 655

Asp Glu

<210> SEQ ID NO 16
<211> LENGTH: 417
<212> TYPE: PRT
<213> ORGANISM: E. coli

<400> SEQUENCE: 16

Met Ser Phe Cys Trp Asn Glu Ile Asn Ser Gly Ile Lys Ser Leu Ile
1               5                   10                  15

Leu Ile Leu Cys Ile Phe Ser Leu Met Thr Leu Ser Leu Trp Asp Asp
            20                  25                  30

Val Ala Thr Lys Phe Leu His Ala Ala Gly Ile Ile Ser Ala Leu Tyr
        35                  40                  45

Phe Leu Ala Thr Pro Lys Lys Thr Ile Thr Asn Asn Pro Thr Leu Leu
    50                  55                  60

Ile Phe Ile Ser Leu Cys Leu Gly Ile Val Asn Ile Ile Trp Tyr
65                  70                  75                  80

Ser His Tyr Lys Val Ser Gly Ser Val Tyr Thr Asn Ala Tyr Arg Gly
                85                  90                  95

Pro Met Glu Thr Gly Lys Ile Ala Leu Cys Ser Ala Phe Ile Phe Leu
            100                 105                 110
```

```
Val Leu Phe Ala Lys Asn Glu Met Arg Thr Lys Ile Lys Phe Gly Lys
            115                 120                 125

Leu Ile Leu Phe Ala Ser Leu Ala Thr Gln Leu Leu Phe Phe Ala His
        130                 135                 140

Ala Met Trp Gln His Phe Tyr Leu Asn Val Asp Arg Val Ala Leu Ser
145                 150                 155                 160

Ala Ser His Ala Thr Thr Ala Gly Tyr Ile Ile Leu Phe Pro Ser Leu
                165                 170                 175

Leu Ala Ser Ile Leu Ile Leu Lys Ser Asp Phe Arg His Lys Thr Thr
            180                 185                 190

Leu Tyr Thr Ile Asn Phe Met Leu Ser Leu Cys Ala Val Ile Val Thr
        195                 200                 205

Glu Thr Arg Ala Ala Ile Leu Val Phe Pro Phe Phe Ala Leu Ile Leu
    210                 215                 220

Ile Val Met Asp Ser Tyr Ile Asn Lys Arg Ile Asn Tyr Lys Leu Tyr
225                 230                 235                 240

Cys Phe Ile Thr Ile Ala Leu Leu Ala Gly Val Phe Ser Phe Lys Asp
                245                 250                 255

Thr Leu Leu Met Arg Met Asn Asp Leu Asn Asn Asp Leu Val Asn Tyr
            260                 265                 270

Ser His Asp Asn Thr Arg Thr Ser Val Gly Ala Arg Leu Ala Met Tyr
        275                 280                 285

Glu Val Gly Leu Lys Thr Tyr Ser Pro Ile Gly Gln Ser Leu Glu Lys
    290                 295                 300

Arg Ala Glu Lys Ile His Glu Leu Glu Glu Lys Glu Pro Arg Leu Ser
305                 310                 315                 320

Gly Ala Leu Pro Tyr Val Asp Ser His Leu His Asn Asp Leu Ile Asp
                325                 330                 335

Thr Leu Ser Thr Arg Gly Ile Pro Gly Val Val Leu Thr Ile Leu Ala
            340                 345                 350

Phe Ser Ala Ile Leu Ile Tyr Ala Leu Arg Thr Ala Lys Glu Pro Tyr
        355                 360                 365

Ile Leu Ile Leu Leu Phe Ser Leu Leu Val Val Gly Leu Ser Asp Val
    370                 375                 380

Ile Leu Phe Ser Lys Pro Val Pro Thr Ala Val Phe Ile Thr Ile Ile
385                 390                 395                 400

Leu Leu Cys Ala Tyr Phe Lys Ala Gln Ser Asp Gln Cys Leu Leu Glu
                405                 410                 415

Lys

<210> SEQ ID NO 17
<211> LENGTH: 1653
<212> TYPE: DNA
<213> ORGANISM: Artificial
<220> FEATURE:
<223> OTHER INFORMATION: Luciferase coding sequence adapted for
      expression in Clostridium acetobutylicum

<400> SEQUENCE: 17
atggaggatg caaagaatat taagaaaggt ccagctcctt tctacccttt agaagacgga    60
actgctggtg agcaattaca caaggcaatg aagaggtatg cattagtacc aggaactata   120
gcttttactg atgctcatat tgaagtaaat ataacatatg cagaatactt tgagatgtct   180
gtgaggcttg cagaagcaat gaaaagatat ggattaaata ctaaccacag gatagtggtt   240
tgttctgaaa acagcttaca attcttcatg ccagttcttg gagcattatt cattggagtt   300
```

-continued

```
gctgtggctc cagcaaatga catttacaac gagagggagt tgttaaattc aatgaatatt      360
agtcaaccta ctgtagtgtt cgtttctaag aagggacttc agaaaattct aaacgtgcaa      420
aaaaagctac caattattca aaagataata attatggact caaaaactga ttaccaagga      480
ttccagagca tgtatacttt tgttacatct catctaccac caggttttaa tgagtatgat      540
ttcgtgccag aaagctttga cagagataag acaatagctt tgattatgaa cagctcagga      600
tctacaggac tacctaaggg tgtggctcta cctcatagga ctgcttgcgt taggtttagt      660
catgcaaggg accctatatt tggaaatcaa attattcctg atactgcaat actatcagtt      720
gtaccatttc atcacggatt cggtatgttc acaacattgg atatcttat  atgcggtttt      780 agagtggtac ttatgtatag gttcgaggaa gaactttttt taaggagtct acaagactac      840
aaaatacaat cagcattgtt agtgccaaca ttatttagtt ttttcgctaa agcacactt      900 atagataaat acgacttgtc taacctacac gaaatagcaa gcggtggagc tcctttatct      960
aaagaggtag gagaagctgt tgcaaaaaga ttccacttac ctggtataag acagggttat     1020
ggattgacag aaacaacatc agcaatttg  attactccag agggagatga caagccaggt     1080
gctgtaggaa aggtggtacc attctttgaa gctaaagtag tagacttgga cacaggaaaa     1140
actctaggtg tgaatcagag aggagaactt tgcgtaaggg gaccaatgat aatgtcaggt     1200
tatgtaaata atccagaggc aacaaatgca cttatagata aagatggttg gttgcacagc     1260
ggagatatag cttactggga tgaggacgaa cattttttta ttgtggacag gcttaaaagt     1320
ttgattaaat acaaaggtta ccaggtggca ccagctgagc ttgaatctat attgcttcaa     1380
cacccaaata ttttttgatgc tggtgtagca ggtcttcctg atgatgatgc aggagagctt     1440
ccagctgctg tagtagtatt agagcacgga aagacaatga cagaaaagga aatagtggac     1500
tacgttgcat ctcaggttac aactgcaaag aagctaaggg gaggtgttgt ttttgtagac     1560
gaagttccta aaggattgac aggaaagttg gacgctagga agattagaga gattctaata     1620
aaagctaaga agggtggtaa aagtaagtta tag                                  1653
```

<210> SEQ ID NO 18
<211> LENGTH: 3416
<212> TYPE: DNA
<213> ORGANISM: Artificial
<220> FEATURE:
<223> OTHER INFORMATION: Nucleotide sequence of expression vector pJL1 + Luciferase codon sequence adapted for expression in Clostridium acetobutylicum

<400> SEQUENCE: 18

```
agatcaaagg atcttcttga gatccttttt ttctgcgcgt aatctgctgc ttgcaaacaa       60
aaaaaccacc gctaccagcg gtggtttgtt tgccggatca agagctacca actctttttc      120
cgaaggtaac tggcttcagc agagcgcaga taccaaatac tgttcttcta gtgtagccgt      180
agttaggcca ccacttcaag aactctgtag caccgcctac atacctcgct ctgctaatcc      240
tgttaccagt ggctgctgcc agtggcgata agtcgtgtct taccgggttg gactcaagac      300
gatagttacc ggataaggcg cagcggtcgg gctgaacggg gggttcgtgc acacagccca      360
gcttggagcg aacgacctac accgaactga gatacctaca gcgtgagcta tgagaaagcg      420
ccacgcttcc cgaagggaga aaggcggaca ggtatccggt aagcggcagg gtcggaacag      480
gagagcgcac gagggagctt ccaggggaa acgcctggta tctttatagt cctgtcgggt      540
ttcgccacct ctgacttgag cgtcgatttt tgtgatgctc gtcaggggg  cggagcctat      600
```

```
ggaaaaacgc cagcaacgcg atcccgcgaa attaatacga ctcactatag ggagaccaca    660
acggtttccc tctagaaata attttgttta actttaagaa ggagatatac atatggagga    720
tgcaaagaat attaagaaag gtccagctcc tttctaccct ttagaagacg gaactgctgg    780
tgagcaatta cacaaggcaa tgaagaggta tgcattagta ccaggaacta tagcttttac    840
tgatgctcat attgaagtaa atataacata tgcagaatac tttgagatgt ctgtgaggct    900
tgcagaagca atgaaaagat atggattaaa tactaaccac aggatagtgg tttgttctga    960
aaacagctta caattcttca tgccagttct tggagcatta ttcattggag ttgctgtggc   1020
tccagcaaat gacatttaca acgagaggga gttgttaaat tcaatgaata ttagtcaacc   1080
tactgtagtg ttcgtttcta agaagggact tcagaaaatt ctaaacgtgc aaaaaaagct   1140
accaattatt caaagataa taattatgga ctcaaaaact gattaccaag gattccagag    1200
catgtatact tttgttacat ctcatctacc accaggtttt aatgagtatg atttcgtgcc   1260
agaaagcttt gacagagata agacaatagc tttgattatg aacagctcag gatctacagg   1320
actacctaag ggtgtggctc tacctcatag gactgcttgc gttaggttta gtcatgcaag   1380
ggaccctata tttggaaatc aaattattcc tgatactgca atactatcag ttgtaccatt   1440
tcatcacgga ttcggtatgt tcacaacatt gggatatctt atatgcggtt ttagagtggt   1500
acttatgtat aggttcgagg aagaactttt tttaaggagt ctacaagact acaaaataca   1560
atcagcattg ttagtgccaa cattatttag ttttttcgct aaaagcacac ttatagataa   1620
atacgacttg tctaacctac acgaaatagc aagcggtgga gctcctttat ctaaagaggt   1680
aggagaagct gttgcaaaaa gattccactt acctggtata agacagggtt atggattgac   1740
agaaacaaca tcagcaattt tgattactcc agagggagat gacaagccag gtgctgtagg   1800
aaaggtggta ccattctttg aagctaaagt agtagacttg gacacaggaa aaactctagg   1860
tgtgaatcag agaggagaac tttgcgtaag gggaccaatg ataatgtcag gttatgtaaa   1920
taatccagag gcaacaaatg cacttataga taaagatggt tggttgcaca gcggagatat   1980
agcttactgg gatgaggacg aacatttttt tattgtggac aggcttaaaa gtttgattaa   2040
atacaaaggt taccaggtgg caccagctga gcttgaatct atattgcttc aacacccaaa   2100
tatttttgat gctggtgtag caggtcttcc tgatgatgat gcaggagagc ttccagctgc   2160
tgtagtagta ttagagcacg gaaagacaat gacagaaaag gaaatagtgg actacgttgc   2220
atctcaggtt acaactgcaa agaagctaag gggaggtgtt gttttttgtag acgaagttcc   2280 taaaggattg acaggaaagt tggacgctag gaagattaga gagattctaa taaaagctaa   2340
gaagggtggt aaaagtaagt tataggtcga ccggctgcta acaaagcccg aaggaagct   2400 gagttggctg ctgccaccgc tgagcaataa ctagcataac cccttgggc ctctaaacgg   2460 gtcttgaggg gttttttgct gaaagccaat tctgattaga aaaactcatc gagcatcaaa   2520
tgaaactgca atttattcat atcaggatta tcaataccat attttttgaaa agccgtttc   2580 tgtaatgaag gagaaaactc accgaggcag ttccatagga tggcaagatc ctggtatcgg   2640
tctgcgattc cgactcgtcc aacatcaata caacctatta atttcccctc gtcaaaaata   2700
aggttatcaa gtgagaaatc accatgagtg acgactgaat ccggtgagaa tggcaaaagc   2760
ttatgcattt ctttccagac ttgttcaaca ggccagccat tacgctcgtc atcaaaatca   2820
ctcgcatcaa ccaaaccgtt attcattcgt gattgcgcct gagcgagacg aaatacgcga   2880
tcgctgttaa aaggacaatt acaaacagga tcgaatgca accggcgcag gaacactgcc   2940
agcgcatcaa caatatttc acctgaatca ggatattctt ctaatacctg gaatgctgtt   3000
```

| | |
|---|---|
| ttcccgggga tcgcagtggt gagtaaccat gcatcatcag gagtacggat aaaatgcttg | 3060 |
| atggtcggaa gaggcataaa ttccgtcagc cagtttagtc tgaccatctc atctgtaaca | 3120 |
| tcattggcaa cgctaccttt gccatgtttc agaaacaact ctggcgcatc gggcttccca | 3180 |
| tacaatcgat agattgtcgc acctgattgc ccgacattat cgcgagccca tttatacccca | 3240 |
| tataaatcag catccatgtt ggaatttaat cgcggcttcg agcaagacgt ttcccgttga | 3300 |
| atatggctca taacacccct tgtattactg tttatgtaag cagacagttt tattgttcat | 3360 |
| gatgatatat ttttatcttg tgcaatgtaa catcagagat tttgagacac aacgtg | 3416 |

<210> SEQ ID NO 19
<211> LENGTH: 1653
<212> TYPE: DNA
<213> ORGANISM: Artificial
<220> FEATURE:
<223> OTHER INFORMATION: Luciferase codon sequence adapted for
      expression in Clostridium autoethanogenum

<400> SEQUENCE: 19

| | |
|---|---|
| atggaagatg caaaaaatat aaagaaagga ccagcaccat tctatccact tgaagacgga | 60 |
| acagcaggag aacagctaca taagcaatg aaaagatatg cacttgtacc gggaacaata | 120 |
| gcttttactg atgctcacat agaagtaaac ataacctatg cggaatattt tgaaatgtca | 180 |
| gtaagattgg cagaggcaat gaaaagatat ggattaaata caaatcatag aatagtagtg | 240 |
| tgtagtgaaa acagcttgca gttttttatg cctgtacttg gtgctttatt cataggtgta | 300 |
| gcagtagcac cagctaatga tatttataat gaacgtgagc ttttaaattc tatgaatata | 360 |
| agtcagccaa ctgtagtatt tgtttcaaag aaaggttttg caagagtttt gaatgttcaa | 420 |
| aagaaattgc ctataattca aaaaataata attatggatt ctaagacaga ttatcaggga | 480 |
| ttccagtcta tgtatacatt cgtaacatct catcttcccc cgggatttaa tgaatatgac | 540 |
| ttcgtacctg aatccttga tagagataag acaatagctt taatcatgaa tagttcagga | 600 |
| agcacaggac ttcctaaagg tgtggcactt ccacatagaa ctgcttgtgt tagattctct | 660 |
| catgctagag atccaatttt tggaaatcaa ataattccag atacagcaat actaagtgta | 720 |
| gtaccattcc atcatggatt tgggatgttt acaactcttg gatatttaat ttgtggtttt | 780 |
| agagttgtat taatgtatag atttgaggaa gaactcttcc ttcgttcact acaagactat | 840 |
| aagatacaat ctgctttact tgtaccaact ttattttcat tttttgctaa gagtactctt | 900 |
| atagataaat atgatttaag caacctgcat gaaaatagcat caggcggcgc tccactatct | 960 |
| aaggaagttg gagaagctgt tgctaaaaga ttccacttac caggaatcag gcagggatat | 1020 |
| ggacttacag aaaacaacttc agcaattctt attacacctg aaggagatga caagcctgga | 1080 |
| gcagtaggta agtggtacc attctttgaa gctaaagtag tagatttaga tacaggaaaa | 1140 |
| acattgggag ttaaccagag aggagagctg tgtgtaagag gacctatgat aatgagtgga | 1200 |
| tatgtaaata tccagaaagc cactaatgca ttaatagata aggatggatg gctgcattct | 1260 |
| ggtgatatag catattggga tgaagatgaa catttttttta ttgtagatag actaaaatcc | 1320 |
| ctaataaaat ataagggata ccaggtagct ccagcagaat tagaatcaat acttctgcag | 1380 |
| catccaaaca tatttgatgc aggagtagct ggattaccag atgatgatgc aggagaactt | 1440 |
| cctgctgcag tagttgtttt agagcatggc aaaactatga ctgaaaaaga gatagttgac | 1500 |
| tatgttgcaa gtcaggttac tacagcaaag aaattgagag cggcgtagt attcgtagat | 1560 |
| gaggttccaa aaggtcttac aggaaaattg gatgcaagaa aaatacgtga aatacttata | 1620 | aaggcaaaga agggcggcaa atcaaaatta taa 1653

<210> SEQ ID NO 20
<211> LENGTH: 1653
<212> TYPE: DNA
<213> ORGANISM: Artificial
<220> FEATURE:
<223> OTHER INFORMATION: Luciferase coding sequence adapted for
      expression in E. coli

<400> SEQUENCE: 20

```
atggaagacg ccaaaaacat aaagaaaggc ccggctccat tctatccgct agaggatgga    60
accgctggag agcaactgca taaggctatg aagagatacg ccctggttcc tggaacaatt   120
gcttttacag atgcacatat cgaggtgaac atcacgtacg cggaatactt cgaaatgtcc   180
gttcggttgg cagaagctat gaaacgatat gggctgaata caaatcacag aatcgtcgta   240
tgcagtgaaa actctcttca attctttatg ccggtgttgg cgcgttatt tatcggagtt    300
gcagttgcgc ccgcgaacga catttataat gaacgtgaat tgctcaacag tatgaacatt   360
tcgcagccta ccgtagtgtt tgtttccaaa aaggggttgc aaaaaatttt gaacgtgcaa   420
aaaaaattac caataatcca gaaaattatt atcatggatt ctaaaacgga ttaccaggga   480
tttcagtcga tgtacacgtt cgtcacatct catctacctc ccggttttaa tgaatacgat   540
tttgtaccag agtcctttga tcgtgacaaa acaattgcac tgataatgaa ctcctctgga   600
tctactgggt tacctaaggg tgtggcccct ccgcatagaa ctgcctgcgt cagattctcg   660
catgccagag atcctatttt tggcaatcaa atcattccgg atactgcgat tttaagtgtt   720
gttccattcc atcacggttt tggaatgttt actacactcg gatatttgat atgtggattt   780
cgagtcgtct taatgtatag atttgaagaa gagctgtttt tacgatccct tcaggattac   840
aaaattcaaa gtgcgttgct agtaccaacc ctattttcat tcttcgccaa agcactctg    900
attgacaaat acgatttatc taatttacac gaaattgctt ctggggggcgc acctctttcg   960
aaagaagtcg gggaagcggt tgcaaaacgc ttccatcttc cagggatacg acaaggatat  1020
gggctcactg agactacatc agctattctg attacacccg agggggatga taaaccgggc  1080
gcggtcggta agttgttcc atttttgaa gcgaaggttg tggatctgga taccgggaaa   1140
acgctgggcg ttaatcagag aggcgaatta tgtgtcagag gacctatgat tatgtccggt  1200
tatgtaaaca atccggaagc gaccaacgcc ttgattgaca aggatggatg gctacattct  1260
ggagacatag cttactggga cgaagacgaa cacttcttca tagttgaccg cttgaagtct  1320
ttaattaaat acaaaggata ccaggtggcc cccgctgaat tggagtcgat attgttacaa  1380
caccccaaca tcttcgacgc gggcgtggca ggtcttcccg acgatgacgc cggtgaactt  1440
cccgccgccg ttgttgtttt ggagcacgga aagacgatga cggaaaaaga tcgtggat    1500
tacgtcgcca gtcaagtaac aaccgcgaaa aagttgcgcg gaggagttgt gtttgtggac  1560
gaagtaccga aaggtcttac cggaaaactc gacgcaagaa aaatcagaga gatcctcata  1620
aaggccaaga agggcggaaa gtccaaattg taa                              1653
```

<210> SEQ ID NO 21
<211> LENGTH: 22
<212> TYPE: DNA
<213> ORGANISM: Artificial Sequence
<220> FEATURE:
<223> OTHER INFORMATION: Primer- pJL1 linear F

<400> SEQUENCE: 21
ctgagatacc tacagcgtga gc                                          22

<210> SEQ ID NO 22
<211> LENGTH: 26
<212> TYPE: DNA
<213> ORGANISM: Artificial Sequence
<220> FEATURE:
<223> OTHER INFORMATION: Primer- pJL1 linear R

<400> SEQUENCE: 22
cgtcactcat ggtgatttct cacttg                                      26

<210> SEQ ID NO 23
<211> LENGTH: 27
<212> TYPE: DNA
<213> ORGANISM: Artificial Sequence
<220> FEATURE:
<223> OTHER INFORMATION: Primer- PS_pJL1 linear F

<400> SEQUENCE: 23
ccgaactgag atacctacag cgtgagc                                     27

<210> SEQ ID NO 24
<211> LENGTH: 31
<212> TYPE: DNA
<213> ORGANISM: Artificial Sequence
<220> FEATURE:
<223> OTHER INFORMATION: Primer- PS_pJL1 linear R

<400> SEQUENCE: 24
tcagtcgtca ctcatggtga tttctcactt g                                31

<210> SEQ ID NO 25
<211> LENGTH: 488
<212> TYPE: DNA
<213> ORGANISM: Clostridium autoethanogenum
<220> FEATURE:
<221> NAME/KEY: misc_feature
<222> LOCATION: (1)..(488)
<223> OTHER INFORMATION: phosphotransacetylase-actetate kinase operon
      (pPta-Ack; CAETHG_RS16490) promoter

<400> SEQUENCE: 25
ggccgcaata tgatatttat gtccattgtg aaagggatta tattcaacta ttattccagt    60
tacgttcata gaaattttcc tttctaaaat attttattcc atgtcaagaa ctctgtttat   120
ttcattaaag aactataagt acaaagtata aggcatttga aaaataggc tagtatattg    180 attgattatt tattttaaaa tgcctaagtg aaatatatac atattataac aataaaataa   240
gtattagtgt aggattttta aatagagtat ctattttcag attaaatttt tgattatttg   300
atttacatta tataatattg agtaaagtat tgactagcaa aatttttga tactttaatt    360 tgtgaaattt cttatcaaaa gttatatttt tgaataattt ttattgaaaa atacaactaa   420
aaaggattat agtataagtg tgtgtaattt tgtgttaaat ttaaagggag gaaatgaaca   480
tgaaacat                                                           488

<210> SEQ ID NO 26
<211> LENGTH: 475
<212> TYPE: DNA
<213> ORGANISM: Clostridium autoethanogenum
<220> FEATURE:
<221> NAME/KEY: misc_feature
<222> LOCATION: (1)..(475)
<223> OTHER INFORMATION: pyruvate:formate oxidoreductase (pPFOR;

CAETHG_RS14890) promoter

<400> SEQUENCE: 26

```
gcaaaatagt tgataataat gcagagttat aaacaaaggt gaaaagcatt acttgtattc    60
tttttatat attattataa attaaaatga agctgtatta gaaaaaatac acacctgtaa   120
tataaaattt taaattaatt tttaattttt tcaaaatgta ttttacatgt ttagaatttt   180
gatgtatatt aaaatagtag aatacataag atacttaatt taattaaaga tagttaagta   240
cttttcaatg tgctttttta gatgtttaat acaaatcttt aattgtaaaa gaaatgctgt   300
actatttact gtactagtga cgggattaaa ctgtattaat tataaataaa aaataagtac   360
agttgtttaa aattatattt tgtattaaat ctaatagtac gatgtaagtt atttttatact  420
attgctagtt taataaaaag atttaattat atacttgaaa aggagaggaa tccat        475
```

<210> SEQ ID NO 27
<211> LENGTH: 558
<212> TYPE: DNA
<213> ORGANISM: Clostridium autoethanogenum
<220> FEATURE:
<221> NAME/KEY: misc_feature
<222> LOCATION: (1)..(558)
<223> OTHER INFORMATION: Wood-Ljungdahl cluster (pWL; CAETHG_RS07860)
    promoter

<400> SEQUENCE: 27

```
agatagtcat aatagttcca gaatagttca atttagaaat tagactaaac ttcaaaatgt   60
ttgttaaata taccaaac tagtatagat attttttaaa tactggactt aaacagtagt    120
aatttgccta aaaaattttt tcaatttttt ttaaaaaatc cttttcaagt tgtacattgt   180
tatggtaata tgtaattgaa gaagttatgt agtaatattg taaacgtttc ttgattttt    240
tacatccatg tagtgcttaa aaaaccaaaa tatgtcacat gcaattgtat atttcaaata   300
acaatattta ttttctcgtt aaattcacaa ataatttatt aataatatca ataaccaaga   360
ttatacttaa atggatgttt atttttttaac acttttatag taaatatatt tattttatgt   420
agtaaaaagg ttataattat aattgtattt attacaatta attaaaataa aaaatagggt   480
tttaggtaaa attaagttat tttaagaagt aattacaata aaaattgaag ttatttcttt   540
aaggagggaa ttattcat                                                 558
```

<210> SEQ ID NO 28
<211> LENGTH: 239
<212> TYPE: PRT
<213> ORGANISM: Clostridium autoethanogenum
<220> FEATURE:
<221> NAME/KEY: MISC_FEATURE
<222> LOCATION: (1)..(239)
<223> OTHER INFORMATION: Metabolic gene: Acetolactate decarboxylase
    (CAETHG_RS14410)

<400> SEQUENCE: 28

```
Met Asp Asp Glu Val Lys Val Pro Asn His Ile Tyr Gln Met Ser Thr
1               5                   10                  15

Ile Asn Ala Leu Val Ser Gly Leu Tyr Asp Gly Cys Val Ser Leu Ser
            20                  25                  30

Lys Leu Leu Lys Lys Gly Asn Phe Gly Ile Gly Thr Phe Lys Gly Leu
        35                  40                  45

Asp Gly Glu Leu Thr Leu Leu Asn Gly Thr Phe Tyr Arg Thr Lys Pro
    50                  55                  60

Asp Gly Ser Val Tyr Val Cys Ser Lys Asn Val Ser Val Pro Phe Ala
```

```
                65                  70                  75                  80
        Val Val Thr Glu Leu Glu Asn Tyr Asn Thr Tyr Asn Ile Gln Asn Arg
                            85                  90                  95

Thr Ser Tyr Glu Asp Ile Arg Lys Glu Leu Asp Ser Phe Ile Glu Ser
                            100                 105                 110

Lys Asn Ile Phe Tyr Ala Phe Tyr Met Glu Gly Lys Phe Asn Tyr Val
                            115                 120                 125

Lys Thr Arg Thr Val Val Lys Gln Asn Met Pro Tyr Lys Pro Met Ala
                            130                 135                 140

Glu Val Val Lys Asp Gln Pro Met Phe Glu Tyr Asn Gly Val Asp Gly
        145                 150                 155                 160

Tyr Val Val Gly Phe Arg Cys Pro Asp Tyr Val Glu Gly Leu Asn Val
                            165                 170                 175

Pro Gly Tyr His Phe His Phe Ile Asn Lys Asp Lys Lys Phe Gly Gly
                            180                 185                 190

His Ile Ser Glu Phe Ser Ile Glu Asn Ala Lys Val Tyr Val Gln Asn
                            195                 200                 205

Cys Ser Cys Phe Arg Met Glu Leu Pro Lys Asn Glu Ser Phe Tyr Asn
                            210                 215                 220

Met Glu Val Gln Asp Arg Asn Asp Glu Ile Thr Ser Val Glu Lys
        225                 230                 235

<210> SEQ ID NO 29
<211> LENGTH: 556
<212> TYPE: PRT
<213> ORGANISM: Clostridium autoethanogenum
<220> FEATURE:
<221> NAME/KEY: MISC_FEATURE
<222> LOCATION: (1)..(556)
<223> OTHER INFORMATION: Metabolic gene: Acetolactate synthase
      (CAETHG_RS08420)

<400> SEQUENCE: 29

Met Asn Arg Asp Ile Lys Lys Glu Val Gln Leu Asn Thr Ala Gln Met
1               5                   10                  15

Leu Val Lys Cys Leu Glu Ala Glu Gly Val Lys Tyr Ile Phe Gly Ile
            20                  25                  30

Pro Gly Glu Glu Asn Leu Glu Ile Met Asn Ala Ile Ser Asp Ser Thr
        35                  40                  45

Ile Glu Phe Ile Thr Thr Arg His Glu Gln Gly Ala Ala Phe Met Ala
    50                  55                  60

Asp Val Tyr Gly Arg Leu Thr Gly Lys Ala Gly Val Cys Leu Ser Thr
65                  70                  75                  80

Leu Gly Pro Gly Ala Thr Asn Leu Val Thr Gly Val Ala Asp Ala Asp
            85                  90                  95

Ser Asp Gly Ala Pro Val Val Ala Ile Thr Gly Gln Val Gly Thr Glu
        100                 105                 110

Arg Met His Ile Thr Ser His Gln Phe Leu Asp Leu Cys Lys Met Phe
    115                 120                 125

Glu Pro Ile Thr Lys Arg Ser Lys Gln Ile Val Arg Pro Asp Thr Val
130                 135                 140

Ser Glu Ile Ile Arg Leu Val Phe Lys Tyr Ala Glu Ser Glu Lys Pro
145                 150                 155                 160

Gly Ala Cys His Ile Asp Leu Pro Val Asn Ile Ala Lys Met Pro Val
            165                 170                 175

Gly Ala Leu Glu Lys Pro Leu Glu Lys Lys Ile Pro Pro Lys Glu His
```

```
            180                 185                 190
Ala Asp Leu Ser Thr Ile Glu Glu Ala Ala Ser Glu Ile Phe Lys Ala
            195                 200                 205

Lys Asn Pro Ile Ile Leu Ala Gly Ser Gly Ala Ile Arg Gly Asn Ser
            210                 215                 220

Ser Lys Ala Val Thr Glu Phe Ala Thr Lys Leu Lys Ile Pro Val Ile
225                 230                 235                 240

Asn Thr Met Met Ala Lys Gly Ile Ile Pro Met Asp Asn Lys Tyr Ser
            245                 250                 255

Met Trp Thr Ile Gly Ile Pro Gln Lys Asp Tyr Val Asn Lys Ile Ile
            260                 265                 270

Glu Glu Ala Asp Leu Val Ile Thr Ile Gly Tyr Asp Ile Val Glu Tyr
            275                 280                 285

Ala Pro Ser Lys Trp Asn Ile Asn Gly Asp Ile Lys Ile Val His Ile
            290                 295                 300

Asp Ala Arg Pro Ser His Ile Asn Lys Leu Tyr Gln Pro Ile Val Glu
305                 310                 315                 320

Val Val Gly Asp Ile Ser Asp Ala Leu Tyr Asn Ile Leu Arg Arg Thr
            325                 330                 335

Ser Ser Lys Asp Glu Pro Val Lys Ala Leu Glu Ile Lys Ser Glu Met
            340                 345                 350

Leu Ala Glu His Glu Ser Tyr Ala Asn Asp Asn Ala Phe Pro Met Lys
            355                 360                 365

Pro Gln Arg Ile Leu Asn Asp Val Arg Lys Val Met Gly Pro His Asp
            370                 375                 380

Ile Val Ile Ser Asp Val Gly Ala His Lys Met Trp Ile Ala Arg His
385                 390                 395                 400

Tyr Asn Cys Tyr Glu Pro Asn Thr Cys Ile Ile Ser Asn Gly Phe Ala
            405                 410                 415

Thr Met Gly Ile Gly Val Pro Gly Ala Ile Ala Ala Lys Leu Ile Asn
            420                 425                 430

Pro Asp Lys Lys Val Leu Ala Ile Val Gly Asp Gly Gly Phe Met Met
            435                 440                 445

Asn Asn Gln Glu Leu Glu Thr Ala Leu Arg Ile Lys Thr Pro Ile Val
            450                 455                 460

Val Leu Ile Phe Asn Asp Ser Asn Tyr Gly Leu Ile Lys Trp Lys Gln
465                 470                 475                 480

Glu Glu His Tyr Gly Lys Ser Cys Tyr Val Asp Phe Thr Asn Pro Asp
            485                 490                 495

Phe Val Lys Leu Ala Glu Ser Met Tyr Ala Lys Gly Tyr Arg Val Glu
            500                 505                 510

Lys Ala Glu Asp Leu Ile Pro Thr Leu Glu Glu Ala Phe Lys Gln Asn
            515                 520                 525

Val Pro Ala Val Ile Asp Cys Gln Val Asp Tyr Gly Glu Asn Ile Lys
            530                 535                 540

Leu Thr Lys His Leu Lys Glu Val Tyr Glu Asn Met
545                 550                 555

<210> SEQ ID NO 30
<211> LENGTH: 351
<212> TYPE: PRT
<213> ORGANISM: Clostridium autoethanogenum
<220> FEATURE:
<221> NAME/KEY: MISC_FEATURE
<222> LOCATION: (1)..(351)
```

<223> OTHER INFORMATION: Metabolic gene: Primary:secondary alcohol
      dehydrogenase (CAETHG_RS02620)

<400> SEQUENCE: 30

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
                20                  25                  30

Ala Val Ser Pro Cys Thr Ser Asp Ile His Thr Val Phe Glu Gly Ala
            35                  40                  45

Leu Gly Asn Arg Glu Asn Met Ile Leu Gly His Glu Ala Val Gly Glu
        50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350
```